(12) United States Patent
Fujimaki et al.

(10) Patent No.: US 11,112,359 B2
(45) Date of Patent: Sep. 7, 2021

(54) TARGET SUBSTANCE DETECTION CHIP, TARGET SUBSTANCE DETECTION DEVICE, AND TARGET SUBSTANCE DETECTION METHOD

(71) Applicants: NATIONAL INSTITUTE OF ADVANCED INDUSTRIAL SCIENCE AND TECHNOLOGY, Tokyo (JP); TOPPAN PRINTING CO., LTD., Tokyo (JP)

(72) Inventors: Makoto Fujimaki, Ibaraki (JP); Hiroki Ashiba, Ibaraki (JP); Masato Yasuura, Ibaraki (JP); Shu Tanabe, Tokyo (JP); Susumu Takahashi, Tokyo (JP)

(73) Assignees: NATIONAL INSTITUTE OF ADVANCED INDUSTRIAL SCIENCE AND TECHNOLOGY, Tokyo (JP); TOPPAN PRINTING CO., LTD., Tokyo (JP)

( * ) Notice: Subject to any disclaimer, the term of this patent is extended or adjusted under 35 U.S.C. 154(b) by 43 days.

(21) Appl. No.: 16/604,877

(22) PCT Filed: Apr. 11, 2018

(86) PCT No.: PCT/JP2018/015170
§ 371 (c)(1),
(2) Date: Oct. 11, 2019

(87) PCT Pub. No.: WO2018/190358
PCT Pub. Date: Oct. 18, 2018

(65) Prior Publication Data
US 2020/0158637 A1 May 21, 2020

(30) Foreign Application Priority Data

Apr. 14, 2017 (JP) .............................. JP2017-080282
Apr. 14, 2017 (JP) .............................. JP2017-080283
Jul. 13, 2017 (JP) .............................. JP2017-136826

(51) Int. Cl.
*G01N 21/64* (2006.01)
*G01N 21/03* (2006.01)
(Continued)

(52) U.S. Cl.
CPC ............. *G01N 21/64* (2013.01); *G01N 21/03* (2013.01); *G01N 21/553* (2013.01); *G01N 33/543* (2013.01)

(58) Field of Classification Search
CPC ...... G01N 21/64; G01N 21/03; G01N 21/553; G01N 33/543; G01N 21/648
See application file for complete search history.

(56) References Cited

U.S. PATENT DOCUMENTS 6,110,749 A * 8/2000 Obremski .......... G01N 21/6452
356/244
2010/0159576 A1 6/2010 Song et al.
2014/0118745 A1 5/2014 Neijzen et al.

FOREIGN PATENT DOCUMENTS

JP H04-084738 A 3/1992
JP H04-178539 A 6/1992
(Continued)

OTHER PUBLICATIONS

Masato Yasuura et al., "Development of Waveguide-mode Image Sensor for Trace Detection", The papers of technical meeting on "chemical sensor", Jun. 29, 2016, pp. 49-52, Jun. 29-30, 2016, The Institute of Electrical Engineers of Japan, Japan.
(Continued)

*Primary Examiner* — Kiho Kim
(74) *Attorney, Agent, or Firm* — Michael Best & Friedrich LLP

(57) ABSTRACT

A target substance detection device detecting a target substance using magnetic particles includes a detection chip, a
(Continued)

light irradiation unit, and a magnetic field application unit, wherein the detection chip includes a light transmissive member having a sensing surface arranged on a surface constituting a top surface relative to a bottom surface, an inclined surface, and a main body portion capable of receiving light and guiding the light through the interior, the light transmissive member having a light directing structure in which the light applied from the top surface side and passed through the inclined surface is directed via the main body portion to the sensing surface under the condition of total reflection, the light irradiation unit is operable to irradiate the sensing surface with light under the condition of total reflection via the light directing structure, and the magnetic field application unit.

9 Claims, 20 Drawing Sheets

(51) Int. Cl.
  *G01N 21/552* (2014.01)
  *G01N 33/543* (2006.01)

(56) References Cited

FOREIGN PATENT DOCUMENTS

| JP | 2002-236258 A | 8/2002 |
|---|---|---|
| JP | 2005-077338 A | 3/2005 |
| JP | 2005-195477 A | 7/2005 |
| JP | 2007-248253 A | 9/2007 |
| JP | 2007-271597 A | 10/2007 |
| JP | 2008-249361 A | 10/2008 |
| JP | 2010-071682 A | 4/2010 |
| JP | 2010-512534 A | 4/2010 |
| JP | 2011-107032 A | 6/2011 |
| JP | 5301894 B2 | 9/2013 |
| JP | 5920692 B2 | 5/2016 |
| WO | 2007102585 A1 | 9/2007 |
| WO | WO-2015/030833 A1 | 3/2015 |
| WO | WO-2015/194663 A1 | 12/2015 |

OTHER PUBLICATIONS

Masato Yasuura et al., "Detection of Extremely Low Concentrations of Biological Substances Using Near-Field Illumination", Scientific Reports, Dec. 19, 2016, No. 6, Article No. 39241 (2016), DOI: 10.1038/srep39241, Springer Nature Limited.

Makoto Fujimaki et al., "Parallel-incidence-type waveguide-mode sensor with spectral-readout setup", Optics Express, Apr. 20, 2015, pp. 10925-10937, vol. 23, No. 9, DOI:10.1364/OE.23.010925, Optical Society of America.

Ken-Ichi Nomura et al., "Fluorescence enhancement by a $SiO_2$-based monolithic waveguide structure for biomolecular detection", Journal of Applied Physics, Apr. 10, 2013, 143103-1-143103-6, vol. 113, Issue 14, DOI: 10.1063/1.4800826, AIP Publishing LLC.

R.P. Podgorsek et al., "Monitoring the diffusion of vapour molecules in polymer films using SP-leaky-mode spectroscopy", Aug. 31, 1998, pp. 146-151, vol. 51, Issues 1-3. DOI: 10.1016/S0925-4005(98)00172-5, Elsevier B.V.

International Search Report issued in Application No. PCT/JP2018/015170, dated Jul. 3, 2018.

Search Report issued in European Application No. 18784840.3, dated Nov. 26, 2020.

Notice of Reasons for Refusal issued in Japanese Application No. 2017-080282, dated Nov. 10, 2020.

* cited by examiner

TARGET SUBSTANCE DETECTION CHIP, TARGET SUBSTANCE DETECTION DEVICE, AND TARGET SUBSTANCE DETECTION METHOD

TECHNICAL FIELD

The present invention relates to a target substance detection chip, a target substance detection device, and a target substance detection method capable of optically detecting a target substance existing in a liquid by utilizing an evanescent field or an enhanced electric field generated with total reflection of light.

BACKGROUND ART

Recently, methods for detecting and determining the quantity of micro substances existing in a solution, particularly of bio-related substances such as DNAs, RNAs, proteins, viruses, and bacteria, have been developed. As one of such methods, for example, a method utilizing an evanescent field generated by total reflection is known.

Examples of the method utilizing the evanescent field generated by total reflection include total reflection fluorescence microscopy. The total reflection fluorescence microscopy technique causes incident light to totally reflect at the interface between a sample liquid and a cover glass or a slide glass, and utilizes a resultant evanescent field as excitation light to observe fluorescence in the presence of less background light as noise (see Patent Document 1). This technique can realize super-resolution, enabling single molecule observation.

As the method utilizing the total reflection, there has been proposed a method that uses a magnetic particle bound to a target substance, applies a magnetic field with a magnet disposed beneath a detection chip to draw a conjugate of the target substance and the magnetic particle toward a localized area on the surface of the detection chip, and irradiates the localized area with the excitation light to detect the target substance (see Patent Document 2). With this proposal, the magnetic field applied promotes adsorption or approach of the target substance to the surface of the detection chip, enabling measurement in a short time.

With this proposal, however, the optical prism present beneath the detection chip makes it difficult to sufficiently decrease the distance between the localized area and the magnet, so the magnetic field applied by the magnet will attenuate in intensity before reaching the surface of the detection chip, causing a problem that the target substance cannot be sufficiently drawn toward the localized area.

Further, an attempt to apply a powerful magnetic field so as to solve this problem will lead to an increased scale of the device as well as an increased manufacturing cost.

As the fluorescence detection method using the magnetic particles, there has been proposed a method of observing and comparing the states before and after application of a magnetic field by a magnetic field application unit (for example, a magnet), to perform the detection by eliminating noise signals from among the optical signals obtained before the application of the magnetic field (see Non-Patent Documents 1, 2). According to this proposal, while the target substance with the magnetic particle bound thereto will move with the magnetic field applied, noise caused by scratches on the surface of the detection chip or the like will not move with the applied magnetic field, so the detection focusing on the moving optical signals can eliminate the noise signals.

However, this method of observing and comparing the states before and after the application of a magnetic field also uses the optical prism, so attenuation in intensity of the magnetic field will make it difficult to move the target substance. Further, an attempt to increase the intensity of the magnetic field will lead to an increased scale of the device as well as an increased manufacturing cost.

As the methods for detecting and determining the quantity of micro substances existing in a solution, particularly of bio-related substances such as DNAs, RNAs, proteins, viruses, and bacteria, for example, a method utilizing surface plasmon resonance and a method utilizing excitation of a waveguide mode (also called an optical waveguide mode, wave-guiding mode, optical wave-guiding mode, etc.) are known.

As the method utilizing the surface plasmon resonance, surface plasmon-field resonance enhanced fluorescence spectroscopy is known.

This method uses an optical setup called Kretschmann configuration to cause the incident light to totally reflect at the interface between a thin gold film layer on a surface of glass in contact with a prism and a sample liquid to excite a surface plasmon resonance on the thin gold film, and form an enhanced electric field on the surface of the thin gold film. The method uses light intensified in the vicinity of the surface of the thin gold film by the surface plasmon resonance as excitation light to excite fluorescent molecules existent in the enhanced electric field to generate intense fluorescence, and performs observation of the fluorescence in the presence of less background light (see Patent Document 3).

The aforementioned method utilizing excitation of the waveguide mode uses a detection chip having a silicon layer (semiconductor layer) and a SiO2 layer stacked in this order on a silica glass substrate. The detection chip is disposed on a trapezoidal prism made of silica glass, and light is applied from the trapezoidal prism side under the condition of total reflection at the detection chip, to obtain an enhanced electric field (see Non-Patent Document 3). With this method, when the detection chip is irradiated with the light from the rear face side (the silica glass substrate side) in a specific angle of incidence while satisfying the condition of total reflection, light of a specific wavelength is coupled to the waveguide mode propagating in the detection chip, whereby the waveguide mode is excited. With the waveguide mode excited, the enhanced electric field is generated in the vicinity of the surface of the detection chip. The fluorescent molecules in the enhanced electric field are thus excited, enabling observation of the fluorescence in the presence of less background light (see Non-Patent Document 4). It should be noted that the aforesaid semiconductor layer may be formed with a metallic layer. The waveguide mode that is excited in a detection chip having the metallic layer as the semiconductor layer may be called a leaky mode, a leak mode, or the like (see Non-Patent Document 5).

Meanwhile, as the method utilizing the surface plasmon resonance, there has been proposed a method of using a magnetic particle bound to a target substance, applying a magnetic field to draw a conjugate of the target substance and the magnetic particle toward a localized area on the surface of the detection chip, and irradiating the localized area with the excitation light to detect the target substance. With this method, the magnetic field applied promotes adsorption or approach of the target substance to the surface of the detection chip, enabling measurement in a short time (see Patent Document 4).

An optical device using such magnetic particles will be described with reference to the drawings. FIG. 13 is a cross-sectional view illustrating an overview of the optical device.

As shown in FIG. 13, the optical device 200 has a detection chip 204, made up of a glass substrate 202 and a metallic film 203, disposed on an optical prism 201. The glass substrate 202 is of a box shape, and a sample liquid is introduced in the interior where the metallic film 203 is disposed. The device also includes a light irradiation unit 205, and a magnet 206 as a magnetic field application unit.

In the optical device 200, the rear face side of the detection chip 204 (the side in contact with the optical prism 201) is irradiated with light from the light irradiation unit 205 under the condition of total reflection, to cause an enhanced electric field to be generated on the localized area, which is the irradiated area in the metallic film 203, to thereby detect fluorescence from the target substance included in the sample liquid.

At this time, the target substance existent as a conjugate with the magnetic particle is drawn toward the localized area by the magnetic field applied from the magnet 206, so the target substance can be detected in a short time.

However, in the optical device 200, the presence of the optical prism 201 makes it difficult to position the metallic film 203, creating the localized area, and the magnet 206 sufficiently close to each other. With the intensity of the magnetic field applied by the magnet 206 attenuated, the target substance cannot be drawn toward the localized area sufficiently.

An attempt to apply a powerful magnetic field to solve the problem will lead to an increased scale of the device as well as an increased manufacturing cost.

Further, as the fluorescence detection method using the magnetic particles, there has been proposed a method of observing and comparing the states before and after application of a magnetic field by a magnetic field application unit (for example, a magnet), to perform the detection by eliminating noise signals from the optical signals obtained before the application of the magnetic field. According to this method, while the target substance with the magnetic particle bound thereto will move with the magnetic field applied, noise caused by scratches on the surface of the detection chip or the like will not move with the applied magnetic field, so the detection focusing on the moving optical signals can eliminate the noise signals (see Non-Patent Documents 1, 2). In the case of a target substance that does not emit light such as fluorescence, a fluorescent material or the like may be bound to label the target substance, and the light emitted therefrom may be detected.

In this method of observing and comparing the states before and after the application of magnetic field as well, the optical prism is used as in the optical device 200. With the attenuation of the intensity of the magnetic field, it becomes difficult to move the target substance. An attempt to increase the intensity of the magnetic field will lead to an increased scale of the device as well as an increased manufacturing cost.

In order to prevent an increase in size of the device due to the optical prism, there has also been proposed a method in which, instead of using the optical prism, an electric field enhancement layer is formed in a groove of V shape or the like for introducing the sample liquid in the detection chip, to make the detection chip by itself play a role as the optical prism (see Patent Document 4).

However, in this method as well, in order to perform the fluorescence detection using the magnetic particles, the light irradiation unit is disposed so as to apply light to the groove from the side of a surface (rear face) of the detection chip that is opposite to the surface (front face) constituting the sensing surface where the groove is formed. This leads to contention in terms of positioning with the magnet or the like that is disposed on the side of the rear face of the detection chip.

In this regard, when the magnet or the like disposed on the side of the rear face of the detection chip is placed distant from the path of the light applied from the light irradiation unit, the distance between the magnet or the like and the front face side of the detection chip on which the sample liquid is introduced increases correspondingly. For example, as shown in FIG. 14, when magnets 306a, 306b are disposed on the side of the rear face of the detection chip 304 away from the path of the light applied from the light irradiation unit 305, the distances between the magnets 306a, 306b and the front face side of the detection chip 304 where the metallic film 303 is formed increase. FIG. 14 illustrates the state where the distances between the front face side of the detection chip and the magnets or the like increase.

This causes attenuation in intensity of the magnetic field, making it difficult to draw or move the target substance. An attempt to solve this problem by increasing the intensity of the magnetic field will eventually result in an increased scale of the device as well as an increased manufacturing cost.

Further, the fluorescence observation method has a problem in detection accuracy, and a further improvement of the detection accuracy is desired.

Specifically, the optical signals detected in the fluorescence observation method include, besides fluorescence from the fluorescent molecules, noise signals caused by scattered light due to the dirt or scratches on the surface of the detection chip, autofluorescence from the components of the detection chip, light emitted from the contaminants included in the sample, and so on. Thus, in the fluorescence observation method, it is required to eliminate the noise signals that would degrade the detection accuracy.

In view of the foregoing, the present inventors have proposed a target substance detection method that eliminates such noise signals. In this method, a labeling substance such as a fluorescent labeling substance or light scattering substance and a magnetic particle are bound to a target substance, and states of the resultant conjugate before and after application of a magnetic field by a magnetic field application unit (for example, a magnet) are observed and compared, to perform the detection by eliminating the noise signals included in the optical signals obtained before the application of the magnetic field.

According to this method, the detection can be performed by eliminating the noise signals by making use of the fact that, while the target substance with the labeling substance and the magnetic particle bound thereto will move with the magnetic field applied, the noise signals caused by scratches on the surface of the detection chip or the like will not move with the applied magnetic field (see Non-Patent Documents 1, 2).

However, in this proposal as well, the conjugate may be non-specifically adsorbed to the surface of the detection chip and thus may not move before and after the application of the magnetic field. As the optical signal from the conjugate that does not move is regarded as the same as the noise signal, the detection accuracy may not be improved depending on the state of adsorption of the conjugates to the detection chip. On the other hand, if an attempt is made to apply a powerful magnetic field to ensure the movement of the conjugates so as to solve the above problem, the device will increase in scale, and the manufacturing cost will also increase.

PRIOR ART DOCUMENTS

Patent Documents

Patent Document 1: Japanese Patent Application Laid-Open No. 2002-236258
Patent Document 2: Japanese Patent No. 5301894
Patent Document 3: International Patent Publication No. WO 2015/194663
Patent Document 4: Japanese Patent No. 5920692

Non-Patent Documents

Non-Patent Document 1: Masato Yasuura and Makoto Fujimaki, "Development of Waveguide-mode Image Sensor for Trace Detection", the Institute of Electrical Engineers Society materials, the Sensors and Micromachines Society (Jun. 29 and 30, 2016), pp. 45-52, the Institute of Electrical Engineers of Japan (2016)
Non-Patent Document 2: M. Yasuura and M. Fujimaki, Sci. Rep. Vol. 6, pp. 39241-1-39241-7 (2016)
Non-Patent Document 3: M. Fujimaki et al. Optics Express, Vol. 23 (2015) pp. 10925-10937
Non-Patent Document 4: K. Nomura et al. J. Appl. Phys. Vol. 113, (2013) pp. 143103-1-143103-6
Non-Patent Document 5: R. P. Podgorsek, H. Franke, J. Woods, and S. Morrill, Sensor. Actuat. B51 pp. 146-151 (1998)

SUMMARY OF THE INVENTION

Problems to be Solved by the Invention

A first invention relates to the above-described problems in the conventional techniques and has an object to provide a target substance detection device that can be used in detecting a target substance using magnetic particles and that can be manufactured compactly and inexpensively, and a target substance detection method using the target substance detection device.

A second invention relates to the above-described problems in the conventional techniques and has an object to provide a target substance detection chip, a target substance detection device, and a target substance detection method that can be used in detecting a target substance using magnetic particles and that allow the target substance detection device to be manufactured compactly and inexpensively.

A third invention relates to the above-described problems in the conventional techniques and has an object to provide a target substance detection chip, a target substance detection device, and a target substance detection method that can be used in detecting a target substance using magnetic particles, that can improve detection accuracy of the target substance, and that allow the target substance detection device to be manufactured compactly and inexpensively.

Means for Solving the Problems

The first invention provides means for achieving the above object as follows:
<1> A target substance detection device comprising: a detection chip including an entirely approximately plate-shaped light transmissive member, the light transmissive member having a sensing surface arranged on a surface constituting a top surface relative to a bottom surface, an inclined surface which is one of an upwardly inclined surface inclined away from the sensing surface from the top surface toward the bottom surface side with respect to a thickness direction and a downwardly inclined surface inclined away from the sensing surface from the bottom surface toward the top surface side with respect to the thickness direction, and a main body portion capable of receiving light and guiding the light through an interior thereof, the light transmissive member having a light directing structure which is one of a first light directing structure in which the light applied from the top surface side and passed through the upwardly inclined surface is directed via the main body portion to the sensing surface under a condition of total reflection and a second light directing structure in which the light applied from the top surface side and reflected at the downwardly inclined surface is directed via the main body portion to the sensing surface under the condition of total reflection; a light irradiation unit disposed on the side of the top surface of the light transmissive member and operable to irradiate the sensing surface with the light under the condition of total reflection via the light directing structure; and a magnetic field application unit disposed on the side of the bottom surface of the light transmissive member.
<2> The target substance detection device according to <1> above, wherein the light transmissive member has at least one notch portion out of a top surface side notch portion formed in the top surface and having the upwardly inclined surface and a bottom surface side notch portion formed in the bottom surface and having the downwardly inclined surface.
<3> The target substance detection device according to <2> above, wherein the notch portion is filled with a low refractive material that is lower in refractive index than the main body portion.
<4> The target substance detection device according to <1> above, wherein the light transmissive member has a side surface constituting the inclined surface.
<5> The target substance detection device according to any of <1> to <4> above, wherein the light directing structure is operable to cause at least one of the light passed through the upwardly inclined surface in the first light directing structure and the light reflected at the downwardly inclined surface in the second light directing structure to be reflected at the bottom surface before being directed to the sensing surface under the condition of total reflection.
<6> The target substance detection device according to any of <1> to <5> above, wherein a shortest distance between a light incident position on the inclined surface and an irradiated position on the sensing surface is 1.0 mm to 50.0 mm.
<7> The target substance detection device according to any of <1> to <6> above, wherein the light transmissive member has a thickness of 0.1 mm to 10.0 mm.
<8> The target substance detection device according to any of <1> to <7> above, wherein the light transmissive member has a sample liquid storage groove formed in the top surface, the groove having at least a portion constituting the sensing surface.
<9> The target substance detection device according to <8> above, wherein the sample liquid storage groove has, as the sensing surface, an inclined sensing surface inclined away from the inclined surface from the top surface toward the bottom surface side with respect to the thickness direction of the light transmissive member.

<10> The target substance detection device according to any of <1> to <7> above, wherein the light transmissive member has a portion of the top surface constituting the sensing surface, and has a sidewall portion erected around the sensing surface to form a box-shaped body with the sensing surface as a bottom thereof.

<11> A target substance detection method using the target substance detection device according to any of <1> to <10> above, comprising: a light irradiation step of irradiating the sensing surface with light under a condition of total reflection from the side of the top surface of the light transmissive member via the light directing structure; and a magnetic field application step of applying a magnetic field from the side of the bottom surface of the light transmissive member.

The second invention provides means for achieving the above object as follows:

<12> A target substance detection chip comprising: an electric field enhancement layer in which an enhanced electric field is formed on a side of a front face when a rear face is irradiated with light under a condition of total reflection; and an entirely approximately plate-shaped light transmissive member having a support surface capable of supporting the electric field enhancement layer from the rear face side, an inclined surface which is one of an upwardly inclined surface inclined away from the support surface from a top surface, on which the support surface is formed, toward a side of a bottom surface with respect to a thickness direction and a downwardly inclined surface inclined away from the support surface from the bottom surface toward the top surface side with respect to the thickness direction, and a main body portion capable of receiving the light and guiding the light through an interior thereof, wherein the light transmissive member has a light directing structure which is one of a first light directing structure in which the light applied from the top surface side and passed through the upwardly inclined surface is directed via the main body portion to the rear face under the condition of total reflection and a second light directing structure in which the light applied from the top surface side and reflected at the downwardly inclined surface is directed via the main body portion to the rear face under the condition of total reflection.

<13> The target substance detection chip according to <12> above, wherein the light transmissive member has at least one notch portion out of a top surface side notch portion formed in the top surface and having the upwardly inclined surface and a bottom surface side notch portion formed in the bottom surface and having the downwardly inclined surface.

<14> The target substance detection chip according to <13> above, wherein the notch portion is filled with a low refractive material that is lower in refractive index than the main body portion.

<15> The target substance detection chip according to <12> above, wherein the light transmissive member has a side surface constituting the inclined surface.

<16> The target substance detection chip according to any of <12> to <15> above, wherein the light directing structure is operable to cause at least one of the light passed through the upwardly inclined surface in the first light directing structure and the light reflected at the downwardly inclined surface in the second light directing structure to be reflected at the bottom surface before being directed to the rear face under the condition of total reflection.

<17> The target substance detection chip according to any of <12> to <16> above, wherein a shortest distance between a light incident position on the inclined surface and an irradiated position on the electric field enhancement layer is 1.0 mm to 50.0 mm.

<18> The target substance detection chip according to any of <12> to <17> above, wherein the light transmissive member has a thickness of 0.1 mm to 10.0 mm.

<19> The target substance detection chip according to any of <12> to <18> above, wherein the light transmissive member has a sample liquid storage groove formed in the top surface, the groove having at least a portion constituting the support surface.

<20> The target substance detection chip according to <19> above, wherein the sample liquid storage groove has, as the support surface, an inclined support surface inclined away from the inclined surface from the top surface toward the bottom surface side with respect to the thickness direction of the light transmissive member.

<21> The target substance detection chip according to any of <12> to <18> above, wherein the light transmissive member has a portion of the top surface constituting the support surface, and has a sidewall portion erected around the support surface to form a box-shaped body with the support surface as a bottom thereof.

<22> A target substance detection device comprising: the target substance detection chip according to any of <12> to <21> above; a light irradiation unit disposed on the side of the top surface of the light transmissive member and operable to irradiate the rear face of the electric field enhancement layer with light under the condition of total reflection via the light directing structure; and a magnetic field application unit disposed on the side of the bottom surface of the light transmissive member.

<23> A target substance detection method comprising: a light irradiation step, performed on the target substance detection chip according to any of <12> to <21> above, of irradiating the rear face of the electric field enhancement layer with light under a condition of total reflection from the side of the top surface of the light transmissive member via the light directing structure; and a magnetic field application step of applying a magnetic field from the side of the bottom surface of the light transmissive member.

The third invention provides means for achieving the above object as follows:

<24> A target substance detection chip having an uneven structure constituted by a plurality of projections arranged periodically on a light transmissive substrate.

<25> The target substance detection chip according to <24> above, constituted by the light transmissive substrate having a smooth surface, and an uneven structure imparting layer stacked on the smooth surface of the light transmissive substrate and having an uneven surface as a surface opposite to a surface on the side of the light transmissive substrate, wherein the uneven surface forms the uneven structure.

<26> The target substance detection chip according to <24> or <25> above, wherein the light transmissive substrate has disposed thereon an electric field enhancement layer in which, in response to at least one surface irradiated with light under a condition of total reflection, an enhanced electric field is formed on another surface, and, with a surface on the side of the light transmissive substrate as a rear face, the enhanced electric field is enabled to be existent in a vicinity of a front face when the light is applied from the side of the rear face to the one surface of the electric field enhancement layer under the condition of total reflection.

<27> The target substance detection chip according to <26> above, constituted by the light transmissive substrate having a smooth surface, the electric field enhancement layer which is smooth and stacked on the smooth surface of the light transmissive substrate, and an uneven structure imparting layer stacked on the electric field enhancement layer, wherein an uneven surface of the uneven structure imparting layer forms the uneven structure.

<28> The target substance detection chip according to <26> above, constituted by the light transmissive substrate having a smooth surface, an uneven structure imparting layer stacked on the smooth surface of the light transmissive substrate and having a first uneven surface as a surface opposite to a surface on the side of the light transmissive substrate, and the electric field enhancement layer stacked on the first uneven surface of the uneven structure imparting layer and having a second uneven surface as a surface opposite to a surface on the side of the uneven structure imparting layer, the second uneven surface having a shape of an uneven pattern transferred from the first uneven surface, wherein the second uneven surface forms the uneven structure.

<29> The target substance detection chip according to <26> above, constituted by the light transmissive substrate having a first uneven surface, and the electric field enhancement layer stacked on the first uneven surface of the light transmissive substrate and having a second uneven surface as a surface opposite to a surface on the side of the light transmissive substrate, the second uneven surface having a shape of an uneven pattern transferred from the first uneven surface, wherein the second uneven surface forms the uneven structure.

<30> The target substance detection chip according to any of <24> to <29> above, wherein the projections are formed in two or more different shapes, and at least one of the shapes has one of a two-fold rotational symmetry and a linear symmetry.

<31> A target substance detection device comprising: the target substance detection chip according to any of <24> to <30> above; a light irradiation unit operable, with a surface of the target substance detection chip opposite to a surface on which the uneven structure is formed as a rear face, to apply light from the side of the rear face under the condition of total reflection; and a magnetic field application unit constituted by at least one of a first magnetic field application unit operable to apply a first magnetic field that moves a magnetic particle included in a sample liquid introduced onto a front face of the target substance detection chip in a direction parallel to or away from the front face, and a second magnetic field application unit disposed on the side of the rear face of the target substance detection chip and operable to apply a second magnetic field that draws the magnetic particle within the sample liquid introduced on the front face toward the front face.

<32> The target substance detection device according to <31> above, having the second magnetic field application unit, wherein the second magnetic field application unit is movable in a direction having a vector component parallel to an in-plane direction of the front face of the target substance detection chip in the state of applying the second magnetic field.

<33> A target substance detection method comprising: a light irradiation step of, with a surface of the target substance detection chip according to any of <24> to <30> above opposite to a surface on which the uneven structure is formed as a rear face, applying light from the side of the rear face under a condition of total reflection; and a conjugate moving step performed by at least one of a first conjugate moving step of moving a conjugate of a target substance and a magnetic particle included in a sample liquid introduced on a front face of the target substance detection chip in a direction parallel to or away from the front face by application of a first magnetic field, and a second conjugate moving step of drawing the conjugate within the sample liquid toward the front face by application of a second magnetic field from a magnetic field application unit disposed on the side of the rear face.

<34> The target substance detection method according to <33> above, including the second conjugate moving step, wherein the second conjugate moving step includes a step of moving the magnetic field application unit, in the state of applying the second magnetic field, in a direction having a vector component parallel to an in-plane direction of the front face of the target substance detection chip, to move the conjugate following the movement of the magnetic field application unit.

The Fourth Invention

<35> A target substance detection chip comprising: an entirely approximately plate-shaped light transmissive member having a support surface arranged on a surface constituting a top surface relative to a bottom surface, an inclined surface which is one of an upwardly inclined surface inclined away from the support surface from the top surface toward the bottom surface side with respect to a thickness direction and a downwardly inclined surface inclined away from the support surface from the bottom surface toward the top surface side with respect to the thickness direction, and a main body portion capable of receiving light and guiding the light through an interior thereof; and an uneven structure constituted by a plurality of projections arranged periodically on the support surface; wherein the light transmissive member has a light directing structure which is one of a first light directing structure in which the light applied from the side of the top surface and passed through the upwardly inclined surface is directed via the main body portion to the support surface under a condition of total reflection and a second light directing structure in which the light applied from the top surface side and reflected at the downwardly inclined surface is directed via the main body portion to the support surface under the condition of total reflection, the light transmissive member has a sensing surface on a portion thereof, and the sensing surface partially or entirely has the uneven structure.

<36> The target substance detection chip according to <35> above, wherein the support surface has disposed thereon an electric field enhancement layer in which, in response to the support surface irradiated with light under the condition of total reflection, an enhanced electric field is formed on a surface opposite to a surface on the support surface side.

<37> The target substance detection chip according to <35> above, wherein the support surface has formed thereon a region in which, in response to the support surface irradiated with light under the condition of total reflection, an evanescent field is generated on a surface opposite to a surface on the support surface side.

<38> A target substance detection device comprising: the target substance detection chip according to any of <35> to <37> above; a light irradiation unit disposed on the side of the top surface of the light transmissive member and operable to irradiate the support surface with the light under the condition of total reflection via the light directing structure;

and a magnetic field application unit disposed on the side of the bottom surface of the light transmissive member.

It should be noted that the first and second inventions have a common structure of the detection chip that permits closer positioning of the magnetic field application unit in order to suppress attenuation in intensity of the magnetic field applied by the magnetic field application unit.

Further, the first, second, and third inventions have a correspondence relation in that they use the detection chip suitable for detection of the target substance using the magnetic field application unit.

The fourth invention relates to modified examples of the first through third inventions, and has the object, structure, and advantageous effects in common with any of the first through third inventions.

Advantageous Effects of the Invention

The first invention is able to provide, in relation to the above-described problems in the conventional techniques, the target substance detection device that can be used in detecting a target substance using magnetic particles and that can be manufactured compactly and inexpensively, and the target substance detection method using that target substance detection device.

The second invention is able to provide, in relation to the above-described problems in the conventional techniques, the target substance detection chip, the target substance detection device, and the target substance detection method that can be used in detecting a target substance using magnetic particles and that allow the target substance detection device to be manufactured compactly and inexpensively.

The third invention is able to provide, in relation to the above-described problems in the conventional techniques, the target substance detection chip, the target substance detection device, and the target substance detection method that can be used in detecting a target substance using magnetic particles, that can improve detection accuracy of the target substance, and that allow the target substance detection device to be manufactured compactly and inexpensively.

BRIEF DESCRIPTION OF THE DRAWINGS

FIG. 27($b$) is a diagram (2) illustrating how an uneven structure suppresses adsorption of conjugates.

FIG. 31($b$) is a top plan view showing the exemplary formation of uneven structure.

FIG. 32($b$) is the top plan view as well as side views in the longitudinal and lateral directions.

FIG. 34($b$) shows the state on the front face after application of the magnetic field.

FIG. 36($b$) shows the state on the front face after application of the magnetic field.

FIG. 38($b$) shows the state on the front face after movement of the second magnetic field application unit.

MODE FOR CARRYING OUT THE INVENTION

Figure 1:
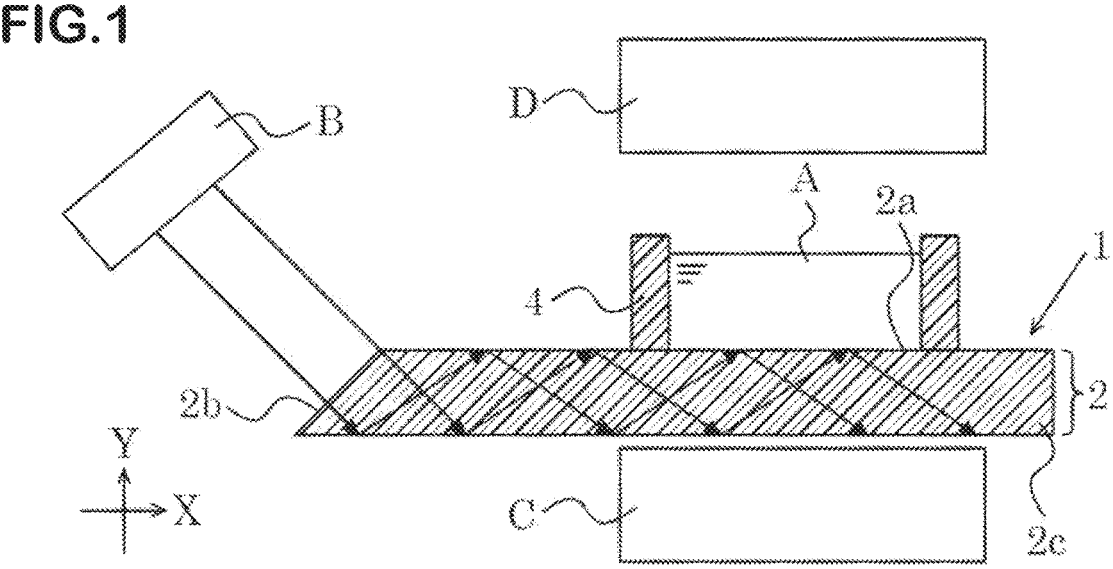
FIG. 1 illustrates an overview of a target substance detection device according to a first embodiment.

The first invention will be described in detail below.
(Target Substance Detection Device)
The target substance detection device of the first invention includes a detection chip, a light irradiation unit, and a magnetic field application unit, and further includes a light detection unit as needed.

<Detection Chip>

The detection chip includes a light transmissive member as follows.

—Light Transmissive Member—

The light transmissive member is of an approximately plate shape as a whole, and has: a sensing surface arranged on a surface constituting a top surface relative to a bottom surface; an inclined surface which is one of an upwardly inclined surface that is inclined away from the sensing surface from the top surface toward the bottom surface side with respect to a thickness direction and a downwardly inclined surface that is inclined away from the sensing surface from the bottom surface toward the top surface side with respect to the thickness direction; and a main body portion capable of receiving light and guiding the light through the interior.

Further, the light transmissive member is configured to have a light directing structure which is one of: a first light directing structure in which the light applied from the top surface side and passed through the upwardly inclined surface is directed, via the main body portion, to the sensing surface under the condition of total reflection, and a second light directing structure in which the light applied from the top surface side and reflected at the downwardly inclined surface is directed, via the main body portion, to the sensing surface under the condition of total reflection.

In the light transmissive member, the optically operating surfaces, i.e. the surface to which light is directed and the surface at which light is reflected, are preferably optically smooth.

The light transmissive member serves as an optical prism provided in the conventional detection chips, and also functions to form an evanescent field on the basis of total reflection of light at the sensing surface. The light transmissive member also has a role of guiding the light applied from the top surface side of the light transmissive member to the sensing surface, so as to allow a magnetic field application unit to be disposed beneath the position in the detection chip where the sensing surface is to be set.

In other words, the light transmissive member is characterized by having the light directing structure that directs the light applied from the top surface side to the sensing surface under the condition of total reflection.

The material for forming the light transmissive member is not particularly limited, and can be selected as appropriate according to the purpose. Preferable materials include: polystyrene, polycarbonate, cycloolefin, acrylic, and other plastic materials capable of high-volume production by injection molding, and silica glass and other glass materials capable of ensuring high transparency. Among them, polystyrene and cycloolefin are less in autofluorescence and can reduce noise. Polycarbonate realizes a high refractive index and enables downsizing. Acrylic has a high transparency and can suppress attenuation of light while guiding the light.

The thickness of the light transmissive member, although not particularly limited, is preferably from 0.1 mm to 10.0 mm from the standpoints of rigidness, light-guiding performance, and degree of attenuation of magnetism. If the thickness is less than 0.1 mm, cracking or deformation would likely occur, making the member difficult to handle. If the thickness is smaller than the beam diameter of incident light, light will be lost at the time of incidence, and noise light will also occur, so the thickness is preferably greater than the beam diameter. Further, as the magnetic field is applied from the bottom surface side, with the thickness exceeding 10.0 mm, the magnetic field may be attenuated, making it difficult to apply a suitable magnetic field onto the sensing surface. The thickness of 5.0 mm or less can considerably suppress the attenuation of the magnetic field.

In the light transmissive member, a sample liquid for which the presence or absence of the target substance is to be verified is introduced into the area where the sensing surface is formed. The configuration for holding the sample liquid introduced is not particularly limited, and the following configurations may be preferably applied.

Specifically, as one configuration, the light transmissive member may have a part of the top surface constituting the sensing surface, and a sidewall portion may be erected around the sensing surface so as to form a box-shaped body with the sensing surface at its bottom. In this configuration, the sample liquid is held in the box-shaped body. For example, the sidewall portion can be formed using a same material as and in a similar manner as the light transmissive member.

As another configuration, the light transmissive member may have a sample liquid storage groove formed in the top surface, the groove having at least a portion constituting the sensing surface. In this configuration, the sample liquid is held in the sample liquid storage groove. The sample liquid storage groove may be formed by molding at the time of forming a plate-like member constituting the light transmissive member, or may be formed by cutting after the forming of the plate-like member.

As yet another configuration, the sample liquid storage groove may be formed as a drilled groove that is drilled from a side surface of the light transmissive member on the side opposite to the side where the inclined surface is formed toward the inclined surface side. In this configuration, a surface of the sample liquid storage groove (drilled groove) that opposes the bottom surface in a closest position constitutes the sensing surface.

In order to prevent spillage of the sample liquid from within the sample liquid storage groove, a cover glass or other lid may be provided, as needed, at an opening of the sample liquid storage groove for sealing.

When the sample liquid storage groove is formed, the groove may have an arbitrary shape such as a recessed shape, a V shape, or a trapezoidal shape in cross sectional view, although semicircular and other shapes with no flat surface are excluded because the sensing surface cannot be formed.

Further, although the configuration of the sample liquid storage groove is not particularly limited, the groove may have, as the sensing surface, an inclined sensing surface which is inclined away from the inclined surface from the top surface toward the bottom surface side with respect to the thickness direction of the light transmissive member. Having such an inclined sensing surface as the sensing surface is advantageous in that the angle of incidence of the light with respect to the inclined surface, which is set to allow the light propagating in the main body portion to be directed to the sensing surface under the condition of total reflection, can be set in a wide range, thereby increasing the degree of freedom of setting.

The detection chip is configured on the assumption that the light is applied from the light irradiation unit disposed on the side of the top surface of the light transmissive member, from the standpoint of avoiding contention with the magnetic field application unit disposed on the side of the bottom surface of the light transmissive member.

That is, in the light directing structure, the traveling direction of the light applied from the side of the top surface of the light transmissive member is changed by the inclined surface, to allow the light to be directed to the sensing surface under the condition of total reflection.

The inclined surface may be formed as a side surface of the light transmissive member, or as a surface constituting a notch portion formed in at least one of the top surface and the bottom surface of the light transmissive member, as long as the inclined surface can function as described above.

The notch portion is formed as at least one of: a top surface side notch portion formed in the top surface of the light transmissive member and having the upwardly inclined surface; and a bottom surface side notch portion formed in the bottom surface of the light transmissive member and having the downwardly inclined surface. The notch portion may be formed by molding at the time of forming a plate-like member constituting the light transmissive member, or may be formed by cutting after the forming of the plate-like member.

Further, in the top surface side notch portion, although the notched portion may be left as a void, it will be difficult to wash off a sample liquid entering in the void, so the notched portion may be filled with a low refractive material having a refractive index lower than that of the main body portion. Filling the top surface side notch portion with the low refractive material can prevent the sample liquid from entering into the top surface side notch portion.

Further, the use of the low refractive material makes it possible to guide the light onto the sensing surface by utilizing the refraction at the interface between the upwardly inclined surface of the top surface side notch portion and the main body portion.

When filling the top surface side notch portion with the low refractive material, for example, a well-known plastic material having the refractive index of about 1.4 may be filled in the top surface side notch portion, and the main body portion may be formed with a well-known plastic material having the refractive index of about 1.6, to obtain the light transmissive member.

The bottom surface side notch portion is formed in the bottom surface of the light transmissive member, so there will be no chance for the sample liquid introduced on the top surface side to enter into that notched portion.

However, from the standpoint of preventing the downwardly inclined surface of the bottom surface side notch portion from being exposed to the outside and contaminated by adhesion of dust or the like in the air, the bottom surface side notch portion is preferably filled with the low refractive material similarly as the top surface side notch portion.

Meanwhile, when the distance between the light incident position on the inclined surface and the irradiated position on the sensing surface (position on the top surface side where the sensing surface is set) is long, the light traveling inside the main body portion will be weakened, and the light will also be weakened every time the light is reflected in the main body portion. On the other hand, if the distance between the light incident position and the irradiated position on the sensing surface is too close, noise due to scattering occurring at the time of incidence of light and the like will be mixed in the optical signals, causing degradation of detection accuracy.

Accordingly, there is a suitable range for the distance between the light incident position on the inclined surface and the irradiated position on the sensing surface, which is specifically preferably 1.0 mm to 50.0 mm at the shortest distance.

Setting the distance as described above can suppress the weakening of the light traveling in the main body portion, and also suppress noise. The number of times of reflection of the light in the main body portion can be reduced, which can be optimally set to once. Further, in the case where the downwardly inclined surface is formed as the inclined surface as well, it is preferable to decrease the number of times of reflection of the light in the main body portion. Thus, the distance is optimally set to allow the light to be reflected only once at the downwardly inclined surface before being directed to the sensing surface, with the number of times of reflection of the light in the main body portion being set to zero.

As used herein, the term "light transmissive" means that the visible light transmittance is 0.5% or more.

<Coating Layer>

The light transmissive member may have a coating layer formed on the sensing surface.

The material for forming the coating layer is not particularly limited as long as it has a light-transmissive property as with the light transmissive member. Examples of the material include well-known resin materials and glass materials.

The method of forming the coating layer is not particularly limited; it may be any of well-known methods including sputtering, vapor deposition, spin coating, application, pasting, and laminating.

The coating layer is formed to cover the sensing surface of the light transmissive member, and the top surface of the coating layer serves as the sensing surface.

When the light transmissive member is formed with a relatively soft resin, the coating layer can coat the member with a rigid resin or glass material that resists scratches, thereby preventing the sensing surface of the light transmissive member from being scratched.

Further, when the coating layer is formed with a fluororesin or the like, it can also produce an antifouling effect of preventing the sensing surface from getting soiled. In addition, the antifouling effect can prevent adsorption of the target substance and the magnetic particle to the top surface of the coating layer. Consequently, in the case of detecting a target substance by moving the target substance with the magnetic particle bound thereto by the magnetic field application unit (described later), it is possible to prevent the conjugate of the magnetic particle and the target substance from becoming immobilized as it is adsorbed to the surface of the coating layer.

Further, when the light transmissive member has the sensing surface suffering roughness due to poor machining accuracy, the coating layer can alleviate such roughness of the sensing surface to suppress scattering of light at the time of total reflection, and can reduce noise. In this case, although the coating layer is not particularly limited, from the standpoint of imparting excellent smoothness to the sensing surface, a thin glass film may be particularly preferably selected as the coating layer and is laminated on the sensing surface of the light transmissive member.

Further, when the coating layer of glass is formed on the sensing surface of the light transmissive member made of resin, a detection chip that has high chemical resistance and is resistant to organic solvents, strong acids, and strong alkalis can be obtained.

It should be noted that the light directing structure can be set by calculating the route of the light applied from the top surface side of the light transmissive member toward the sensing surface, using a well-known optical calculating method, by giving the conditions of: the angle of inclination of the inclined surface, the angle of irradiation of light onto the inclined surface, the quality (refractive index) of the material of the light transmissive member, the distance between the light incident position on the inclined surface and the irradiated position on the sensing surface, the thickness of the light transmissive member, and so on.

<Light Irradiation Unit>

The light irradiation unit is disposed on the side of the top surface of the light transmissive member, and is operable to irradiate the sensing surface with the light under the condition of total reflection via the light directing structure of the light transmissive member.

The light source of the light irradiation unit is not particularly limited, and can be selected as appropriate according to the purpose. Examples of the light source include a well-known lamp, LED, and laser. The detection performed by the target substance detection device is based on the principle that the light is directed to the sensing surface under the condition of total reflection to form the evanescent field in the vicinity of the front face of the sensing surface, thereby causing the conjugate comprising the target substance and the magnetic particle to generate an optical signal. The role required for the light irradiation unit to play to this end is simply to irradiate the sensing surface with the light under the condition of total reflection, and any light source can be selected as long as the unit can play such a role.

When a radiation light source such as a lamp or LED is used, a guide unit such as a collimator lens that restricts the irradiated directions of the light to a specific direction may be used to let the irradiated light incident on the light incident portion.

Further, the light to be incident on the light incident portion is preferably monochromatic light having a wavelength that can excite fluorescence with respect to the conjugate. Alternatively, light from a light source having a wide wavelength range, such as a lamp, LED, or the like, may be passed through an optical filter such as a band-pass filter or the like to obtain monochromatic light, for use as the light having only the wavelength that can excite fluorescence.

<Magnetic Field Application Unit>

The magnetic field application unit is disposed on the side of the bottom surface of the light transmissive member.

The magnetic field application unit, although its position is not particularly limited, is preferably disposed immediately beneath the bottom surface of the light transmissive member, in a position opposing the sensing surface of the detection chip in the thickness direction, from the standpoint of applying a powerful magnetic field to the sample liquid.

The member constituting the magnetic field application unit is not particularly limited as long as it can apply a magnetic field to an area where the sample liquid is introduced. Examples of the member include a well-known permanent magnet and electromagnet.

The sample liquid has well-known magnetic particles such as magnetic beads added thereto. In the presence of the target substance, a conjugate of the target substance and the magnetic particle is formed. If the target substance is less liable to generate fluorescence, a fluorescent labeling substance that is specifically adsorbed to or bound to the target substance to label the target substance may be used. For the fluorescent labeling substance, any of well-known fluorescent substances such as fluorescent dye, quantum dot, fluorescent dyeing agent and the like can be used.

Further, the method of detecting the target substance is not limited to the method of detecting fluorescence; it may be a method of detecting scattered light that is emitted from the conjugate being subject to evanescent light in the evanescent field.

In the case of detecting the scattered light, if the target substance is less liable to generate scattered light, a light scattering substance that is specifically adsorbed to or bound to the target substance to scatter light may be used. Examples of the light scattering substance include nanoparticles such as polystyrene beads and gold nanoparticles.

The method for binding the target substance, the magnetic particle, the fluorescent labeling substance, and the light scattering substance together is not particularly limited, and any of well-known methods such as physical adsorption, antigen-antibody reaction, DNA hybridization, biotin-avidin bond, chelate bond, amino bond, etc. can be used depending on the substances.

Light from the target substance and the like is generated in the evanescent field formed in the vicinity of the front face of the sensing surface. Thus, in order to detect the optical signals in a short time, the conjugates floating in the sample liquid need to be drawn to the vicinity of the front face of the sensing surface.

The magnetic field application unit applies the magnetic field to draw the conjugates floating in the sample liquid toward the front face of the sensing surface, thereby enabling the detection in a short time.

Meanwhile, in order to perform the detection by eliminating noise due to scratches on the sensing surface or the like, the states before and after movement of the conjugates in response to application of the magnetic field by the magnetic field application unit may be observed and compared, to perform the detection by eliminating the noise signals included in the optical signals obtained before the movement of the conjugates. According to such detection, while a target substance with the magnetic particle bound thereto moves by the magnetic field application unit, noise caused by scratches on the sensing surface or the like would not move by the magnetic field application unit, so the detection focusing on the moving optical signals can eliminate the noise signals.

In the case of performing such detection, the magnetic field application unit is made to be movable on the side of the bottom surface of the light transmissive member in the direction having a vector component parallel to the in-plane direction of the sensing surface while applying the magnetic field, so as to observe and compare the states of the conjugates before and after the movement. The magnetic field application unit may be configured with, for example, the permanent magnet or the like and a sliding member capable of sliding the permanent magnet or the like while supporting the same.

<Light Detection Unit>

The light detection unit is disposed above the sensing surface, and is capable of detecting an optical signal emitted from a conjugate comprising the target substance in response to the irradiation of light, by using an area in the vicinity of the front face of the sensing surface as a detection area.

The light detection unit is not particularly limited, and can be selected as appropriate according to the purpose. Examples include well-known photodetectors such as a well-known photodiode, photomultiplier, and the like, and well-known imaging devices such as a CCD image sensor, CMOS image sensor, and the like.

(Target Substance Detection Method)

A target substance detection method in the first invention detects a target substance by using the target substance detection device of the first invention, and includes at least a light irradiation step and a magnetic field application step, and further includes a light detection step as needed.

<Light Irradiation Step>

The light irradiation step is a step of irradiating the sensing surface with light under the condition of total reflection, from the side of the top surface of the light transmissive member via the light directing structure in the light transmissive member.

For performing the light irradiation step, the matters described in relation to the light irradiation unit in the target substance detection device in the first invention can be applied, so the description will not be repeated.

<Magnetic Field Application Step>

The magnetic field application step is a step of applying a magnetic field from the side of the bottom surface of the light transmissive member by the magnetic field application unit. In this step, suitably, the magnetic field application unit is moved, in the state of applying the magnetic field, in the direction having a vector component parallel to the in-plane direction of the sensing surface.

For performing the magnetic field application step, the matters described in relation to the magnetic field application unit in the target substance detection device in the first invention can be applied, so the description will not be repeated.

<Light Detection Step>

The light detection step is a step of detecting an optical signal emitted from the conjugate in response to the irradiation of light.

For performing the light detection step, the matters described in relation to the light detection unit in the target substance detection device in the first invention can be applied, so the description will not be repeated.

While the target substance detection device and the target substance detection method according to the first invention have been described on the basis of the positional relationship among the "top surface", "bottom surface", and "side surface" of the light transmissive member, the positional relationship indicates the relative positional relationship. Even when the target substance detection device is placed upside down or slanted during the use, the device falls within the technical scope of the first invention as long as there is no change in the relative positional relationship. For example, even in the case where the target substance detection device is slanted 90° during the use, with the "top surface" and the "bottom surface" located on respective sides and the "side surface" located on top or bottom, the device falls within the technical scope of the first invention as long as the relative positional relationship between the "top surface" and the "side surface", with the surface of the light transmissive member on the side where the magnetic field application unit is disposed being regarded as the "bottom surface", does not change (see, for example, a seventh embodiment described later and FIG. 12).

First Embodiment

Exemplary configurations of the target substance detection device in the first invention will be specifically described below with reference to the drawings.

Firstly, a target substance detection device according to a first embodiment will be described with reference to FIG. 1. FIG. 1 illustrates an overview of the target substance detection device according to the first embodiment.

As shown in FIG. 1, a detection chip 1 in the first embodiment has a light transmissive member 2. The light transmissive member 2 is of a plate shape, and has a top surface a part of which constitutes a sensing surface 2a, a side surface constituting an upwardly inclined surface 2b, and a body constituting a main body portion 2c which is capable of receiving light from the top surface and guiding the light through the interior. Here, the sensing surface 2a is set in a part of the top surface of the light transmissive member 2, where an evanescent field is formed in the vicinity of the front face (top surface side of the light transmissive member 2) when the rear face (bottom surface side of the light transmissive member 2) is irradiated with light under the condition of total reflection.

On the top surface of the light transmissive member 2, a sidewall portion 4 is erected around the sensing surface 2a to form a box-shaped body with the sensing surface 2a at its bottom. A sample liquid A is introduced into this box-shaped body.

Here, the upwardly inclined surface 2b formed as a side surface of the light transmissive member 2 is inclined away from the sensing surface 2a from the top surface toward the bottom surface side with respect to a thickness direction Y of the light transmissive member 2. Light applied from a light irradiation unit B, disposed opposite to the upwardly inclined surface 2b, is directed into the main body portion 2c obliquely with respect to a lengthwise direction X orthogonal to the thickness direction Y of the light transmissive member 2.

The light incident in the main body portion 2c is propagated through the interior of the main body portion 2c in the lengthwise direction X while being reflected a plurality of number of times at the top surface and the bottom surface of the main body portion 2c.

The light propagated through the interior of the main body portion 2c is totally reflected at the position of the sensing surface 2a, thereby forming an evanescent field in the vicinity of the front face of the sensing surface 2a (first light directing structure).

When configuring the target substance detection device with the detection chip 1, as shown in FIG. 1, the light irradiation unit B is disposed on the side of the top surface of the light transmissive member 2, in a position opposing the upwardly inclined surface 2b as a side surface of the light transmissive member 2. A magnetic field application unit C is disposed immediately beneath the bottom surface of the light transmissive member 2, in a position opposing the sensing surface 2a in the thickness direction Y. A light detection unit D is disposed on the side of the top surface of the light transmissive member 2.

The magnetic field application unit C applies a magnetic field to draw a conjugate comprising a target substance and a magnetic particle, floating in the sample liquid A, to the vicinity of the front face of the sensing surface 2a where the conjugate is capable of emitting an optical signal, thereby enabling the measurement in a short time. Further, when the magnetic field application unit C is caused to slide in the lengthwise direction X, for example, to detect optical signals before and after the sliding, then only the conjugates following the sliding of the magnetic field application unit C can be detected, thereby enabling the detection eliminating the noise signals caused by scratches on the sensing surface 2a and the like.

The light detection unit D is capable of detecting light from the conjugate in the vicinity of the front face of the sensing surface 2a.

In the target substance detection device according to the first embodiment configured as described above, the magnetic field application unit C can be placed in a position beneath the bottom surface of the light transmissive member 2 at a short distance from the sensing surface 2a, and the light applied from the light irradiation unit B can be directed to the sensing surface 2a under the condition of total reflection, without causing contention in placement positions between the light irradiation unit B and the magnetic field application unit C. This eliminates the need to use a powerful magnetic field application member capable of applying a magnetic field from a position far away from the sensing surface 2a, thereby enabling the device to be manufactured compactly and inexpensively, without being increased in scale.

Second Embodiment

Figure 2:
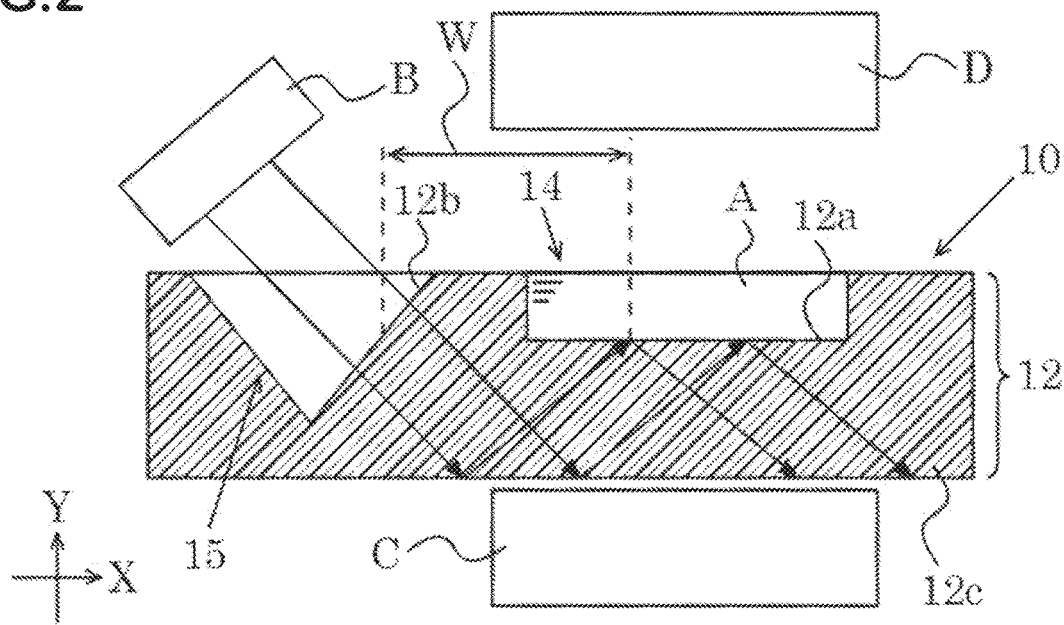
FIG. 2 illustrates an overview of a target substance detection device according to a second embodiment.

A target substance detection device according to a second embodiment will now be described with reference to FIG. 2. FIG. 2 illustrates an overview of the target substance detection device according to the second embodiment.

As shown in FIG. 2, a detection chip 10 according to the second embodiment has a light transmissive member 12. Unlike the light transmissive member 2 in the first embodiment, the light transmissive member 12 has a sample liquid storage groove 14 formed in the top surface for receiving a sample liquid A. The sample liquid storage groove 14 is of a recessed shape in cross section, with its bottom surface constituting a sensing surface 12a.

Further, unlike the light transmissive member 2 in the first embodiment, the light transmissive member 12 has a top surface side notch portion 15 formed in the top surface and having an upwardly inclined surface 12b. The top surface side notch portion 15 is of an approximately V shape in cross section.

Here, the upwardly inclined surface 12b is inclined away from the sensing surface 12a from the top surface toward the bottom surface side with respect to the thickness direction Y of the light transmissive member 12, and light applied from a light irradiation unit B, disposed opposite to the upwardly inclined surface 12b, is directed into the main body portion 12c obliquely with respect to the lengthwise direction X orthogonal to the thickness direction Y of the light transmissive member 12.

A distance W between the light incident position on the upwardly inclined surface 12b and the irradiated position on the sensing surface 12a is suitably 1.0 mm to 50.0 mm at the shortest distance.

The light incident in the main body portion 12c is reflected at the bottom surface of the main body portion 12c the smallest possible number of times, preferably only once, before being directed to the sensing surface 12a. The light is totally reflected at the rear face of the sensing surface 12a, and forms an evanescent field in the vicinity of the front face of the sensing surface 12a (first light directing structure).

When configuring the target substance detection device with the detection chip 10, as shown in FIG. 2, the light irradiation unit B is disposed on the side of the top surface of the light transmissive member 12, in a position opposing the upwardly inclined surface 12b.

In the detection chip 10 configured as described above, the distance W between the light incident position on the upwardly inclined surface 12b and the irradiated position on the sensing surface 12a becomes shorter than the distance between the light incident position on the upwardly inclined surface 2b (side surface of the light transmissive member 2) and the irradiated position on the sensing surface 2a in the detection chip 1 in the first embodiment. This reduces the attenuation of the light traveling through the main body portion 12c.

Other configurations and effects are similar to those of the target substance detection device according to the first embodiment, so the description thereof will be omitted.

Figure 3:
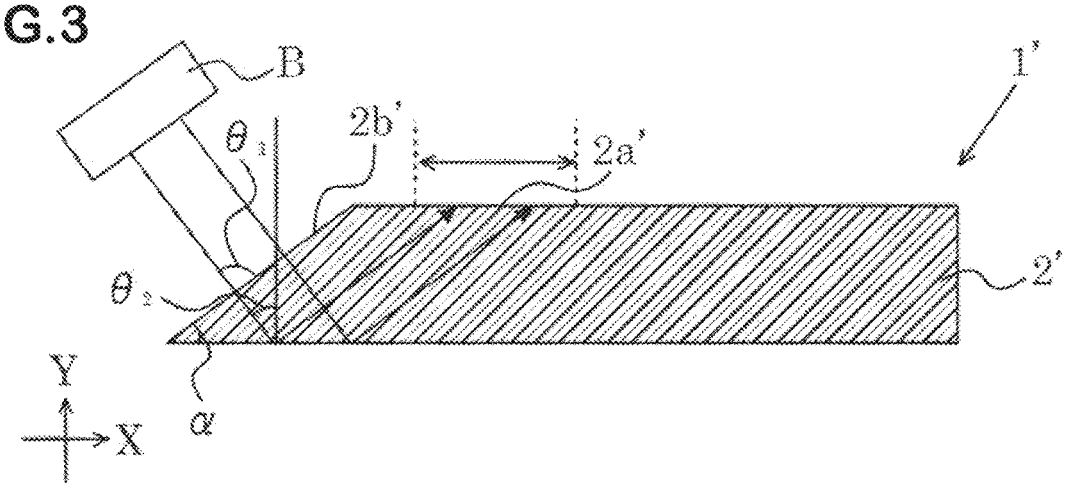
FIG. 3 is a diagram (1) illustrating an exemplary incident angle of light.
Figure 4:
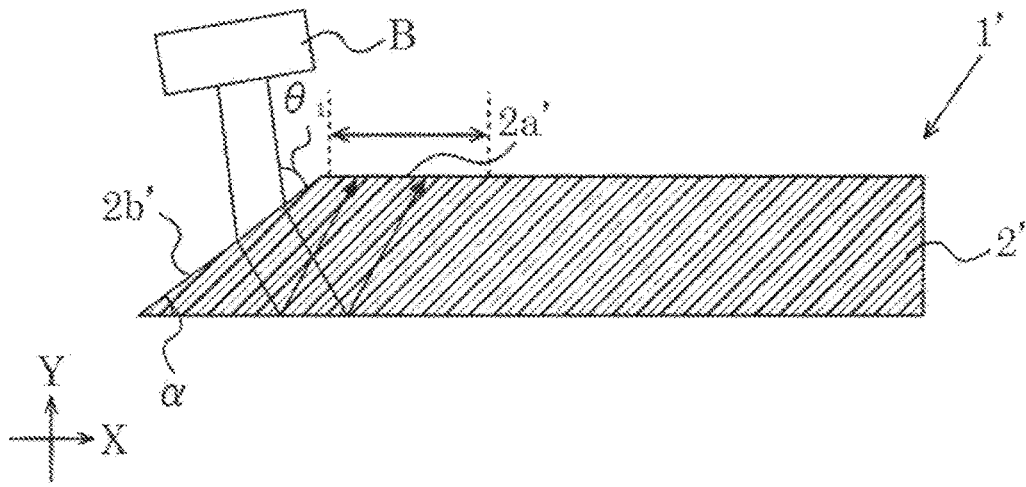
FIG. 4 is a diagram (2) illustrating an exemplary incident angle of light.
Figure 5:
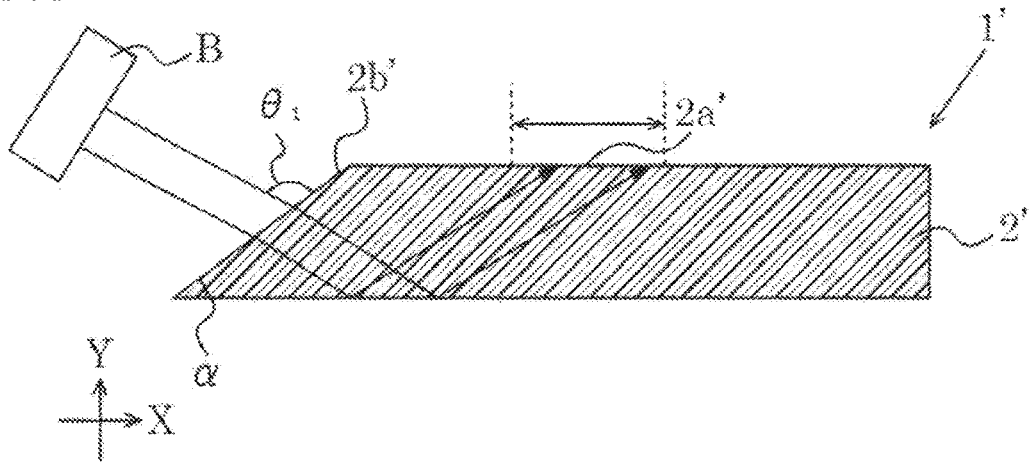
FIG. 5 is a diagram (3) illustrating an exemplary incident angle of light.

Referring now to FIGS. 3 to 5, a supplementary description will be given of the incident angle of light on the upwardly inclined surface 2b of the light transmissive member 2 of the detection chip 1 in the first embodiment. FIGS. 3 to 5 illustrate exemplary incident angles of light.

As shown in FIG. 3, a detection chip 1' has a sensing surface 2a' as a part of a top surface of a light transmissive member 2'.

In the example shown in FIG. 3, with a side surface of the light transmissive member 2' constituting an upwardly inclined surface 2b', a light irradiation direction of a light irradiation unit B is set such that the light enters the light transmissive member 2' in a normal direction, or, in the direction perpendicular to the upwardly inclined surface 2b'. An angle $\theta_1$ made between the light irradiation direction of the light irradiation unit B and the upwardly inclined surface 2b', as seen as a V-shaped groove angle open on the top surface side of the light transmissive member 2', is set to be 90°.

When the light is incident in the direction perpendicular to the upwardly inclined surface 2b' with $\theta_1$ being 90°, no refraction of light occurs at the upwardly inclined surface 2b'. Further, an angle $\theta_2$ made between the thickness direction Y of the light transmissive member 2' and the light incident direction on the bottom surface of the light transmissive member 2' becomes equal to an angle $\alpha$ made between the bottom surface and the side surface (upwardly inclined surface 2b') of the light transmissive member 2' ($\theta_2 = \alpha$). As these phenomena occur irrespective of the material of the light transmissive member 2', it is possible to uniquely specify the light reflected position in the main body portion of the light transmissive member 2' on the basis of the setting of the angle $\alpha$, to thereby simplify the positional setting of the sensing surface 2a' in the detection chip as well as the settings of the optical system in the target substance detection device. In the example shown in FIG. 3, if the angle $\alpha$ is too small, $\theta_2$ also becomes too small, in which case the incident light will not be totally reflected at the bottom surface of the light transmissive member 2', with some components transmitted through to the outside of the light transmissive member 2'. This state should be taken notice of, since the incident light would not be directed to the sensing surface 2a' under the condition of total reflection. On the other hand, if the angle $\alpha$ is too large, it is difficult for the light to enter from the top surface side. Therefore, the angle $\alpha$ is preferably from 50° to 80°.

In the example shown in FIG. 4, the angle $\theta_1$ made between the light irradiation direction of the light irradiation unit B and the upwardly inclined surface 2b', as seen as a V-shaped groove angle open on the top surface side of the light transmissive member 2', is set to be less than 90°.

When the light is incident in the upwardly inclined surface 2b' with $\theta_1$ being less than 90°, the light refracted at the upwardly inclined surface 2b' is reflected at the bottom surface of the light transmissive member 2' and guided to the top surface.

If the light incident angle $\theta_1$ is too small relative to 90°, the light refracted at the upwardly inclined surface 2b' will not be totally reflected at the bottom surface of the light transmissive member 2', with some components transmitted through to the outside of the light transmissive member 2'.

This state should be taken notice of, since the incident light would not be directed to the sensing surface 2a' under the condition of total reflection.

It should also be noted that if $\theta_1$ is too small relative to 90°, the position on the top surface to which the reflected light is directed becomes too close to the side surface (upwardly inclined surface 2b'), making it difficult to set this position on the top surface as the sensing surface 2a'.

Accordingly, when $\theta_1$ is set to be less than 90°, its lower limit is preferably an angle with which the angle made between the light irradiation direction of the light irradiation unit B and the lengthwise direction X of the light transmissive member 2' on the sensing surface 2a' side becomes 90° or more, although it depends on the angle α.

In the example shown in FIG. 5, the angle $\theta_1$ made between the light irradiation direction of the light irradiation unit B and the upwardly inclined surface 2b', as seen as a V-shaped groove angle open on the top surface side of the light transmissive member 2', is set to exceed 90°.

When the light is incident in the upwardly inclined surface 2b' with $\theta_1$ exceeding 90°, the light refracted at the upwardly inclined surface 2b' is reflected at the bottom surface of the light transmissive member 2' and guided to the top surface. This is preferable because, at the time of reflection, the light refracted at the upwardly inclined surface 2b' would likely be totally reflected at the bottom surface of the light transmissive member 2'.

However, it should be noted that if $\theta_1$ is too large relative to 90°, the position on the top surface to which the reflected light is guided will be farther from the upwardly inclined surface 2b', leading to an increase in size of the detection chip 1'.

Accordingly, when $\theta_1$ is set to be an angle exceeding 90°, its upper limit is an angle with which the light irradiation direction of the light irradiation unit B will not reach parallel to the lengthwise direction X of the detection chip 1', although it depends on the angle α.

While the supplementary description has been given of the incident angle of light on the upwardly inclined surface 2b of the light transmissive member 2 of the detection chip 1 in the first embodiment by referring to FIGS. 3 and 5, $\theta_1$ is also applicable to the upwardly inclined surface 12b of the light transmissive member 12 of the detection chip 10 in the second embodiment.

However, it should be noted that when setting $\theta_1$ to an angle exceeding 90°, if $\theta_1$ is too large relative to 90°, a portion of the light transmissive member 12 that constitutes a surface of the V-shaped top surface side notch portion 15 opposing the upwardly inclined surface 12b will become an obstacle to light irradiation, thereby imposing a constraint on the angle setting of $\theta_1$. In contrast, there would likely be no such constraint when setting $\theta_1$ to be equal to or less than 90°.

Third Embodiment

Figure 6:
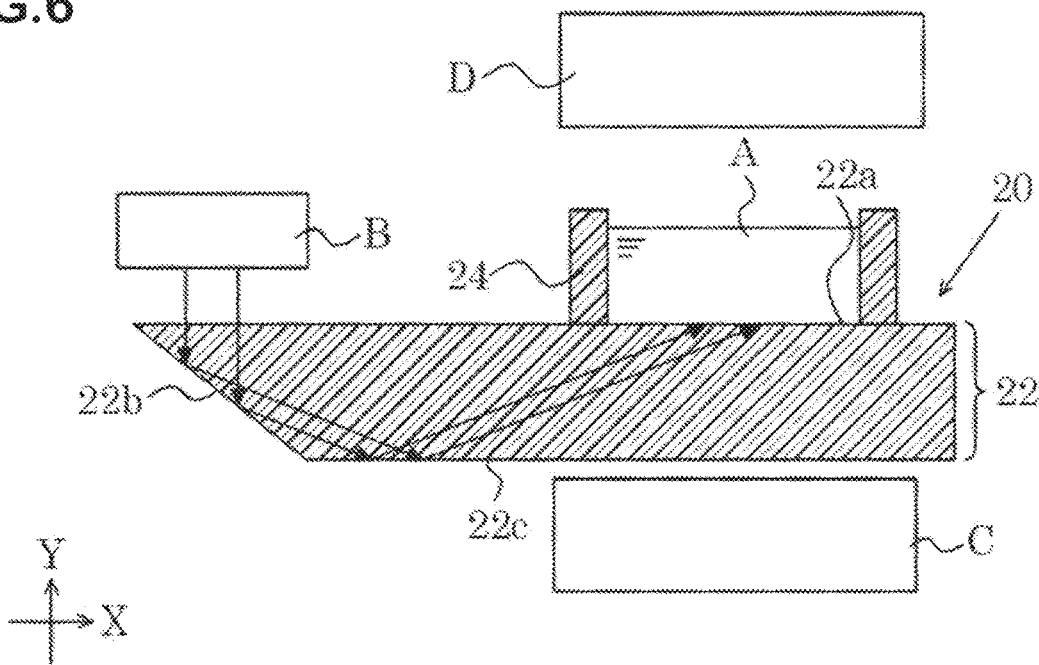
FIG. 6 illustrates an overview of a target substance detection device according to a third embodiment.

A target substance detection device according to a third embodiment will now be described with reference to FIG. 6. FIG. 6 illustrates an overview of the target substance detection device according to the third embodiment.

As shown in FIG. 6, a detection chip 20 in the third embodiment has a light transmissive member 22. The light transmissive member 22 is of a plate shape, and has a top surface a part of which constitutes a sensing surface 22a, and a body constituting a main body portion 22c capable of receiving light from the top surface and guiding the light through the interior. On the top surface of the light transmissive member 22, a sidewall portion 24 is erected around the sensing surface 22a to form a box-shaped body with the sensing surface 22a at its bottom, and a sample liquid A is introduced into this box-shaped body.

Unlike the light transmissive member 2 in the first embodiment, the light transmissive member 22 has a side surface constituting a downwardly inclined surface 22b that is inclined away from the sensing surface 22a from the bottom surface toward the top surface side with respect to the thickness direction Y, and the light is applied to the top surface of the light transmissive member 22 in a position opposite to the side surface in the thickness direction Y.

Here, the light applied from the light irradiation unit B onto the top surface is introduced into the main body portion 22c, and it is reflected at the downwardly inclined surface 22b and the bottom surface in this order, for example, as illustrated in the figure. The light is then totally reflected at the position of the sensing surface 22a, and forms an evanescent field in the vicinity of the front face of the sensing surface 22a (second light directing structure).

In this manner, the detection chip 20 in the third embodiment configured such that the side surface of the light transmissive member 22 faces the bottom surface side, different from the detection chip 1 in the first embodiment in which the side surface of the light transmissive member 22 faces the top surface side, is also capable of producing the evanescent field as with the detection chip 1 in the first embodiment.

Fourth Embodiment

Figure 7:
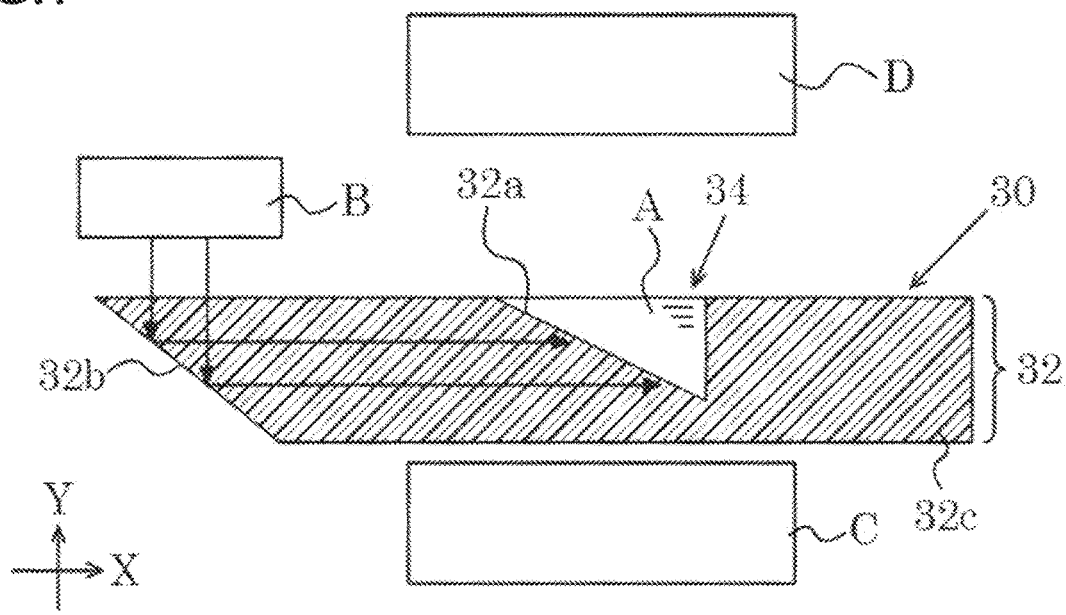
FIG. 7 illustrates an overview of a target substance detection device according to a fourth embodiment.

A target substance detection device according to a fourth embodiment will now be described with reference to FIG. 7. FIG. 7 illustrates an overview of the target substance detection device according to the fourth embodiment.

As shown in FIG. 7, a detection chip 30 in the fourth embodiment has a light transmissive member 32. Unlike the light transmissive member 2 in the first embodiment, the light transmissive member 32 has a sample liquid storage groove 34 formed in the top surface for receiving a sample liquid A. The sample liquid storage groove 34 is of an approximately V shape in cross section, and its surface forming a side of the groove with the approximately V-shaped cross section constitutes a sensing surface 32a.

Here, unlike the light transmissive member 2 in the first embodiment, the light transmissive member 32 has a side surface constituting a downwardly inclined surface 32b that is inclined away from the sensing surface 32a from the bottom surface toward the top surface side with respect to the thickness direction Y, and the light is applied to the top surface of the light transmissive member 32 in a position opposite to the side surface in the thickness direction Y.

A light irradiation unit B irradiates the top surface of the light transmissive member 32 with light in the thickness direction Y, i.e. in the direction perpendicular to the top surface. The light incident in the main body portion 32c is reflected only once at the downwardly inclined surface 32b, without being reflected at the top surface or the bottom surface of the main body portion 32c while being propagated through the interior of the main body portion 32c in the lengthwise direction X. The light is then totally reflected at the position of the sensing surface 32a, and forms an evanescent field in the vicinity of the front face of the sensing surface 32a (second light directing structure).

In the detection chip 30 configured as described above, the light incident in the main body portion 32c is guided toward the sensing surface 32a, without being reflected at the top or bottom surface of the main body portion 32c. This suppresses degradation of the light caused by reflection at the top and bottom surfaces.

Other configurations and effects are similar to those of the target substance detection device according to the first embodiment, so the description thereof will be omitted.

Fifth Embodiment

Figure 8:
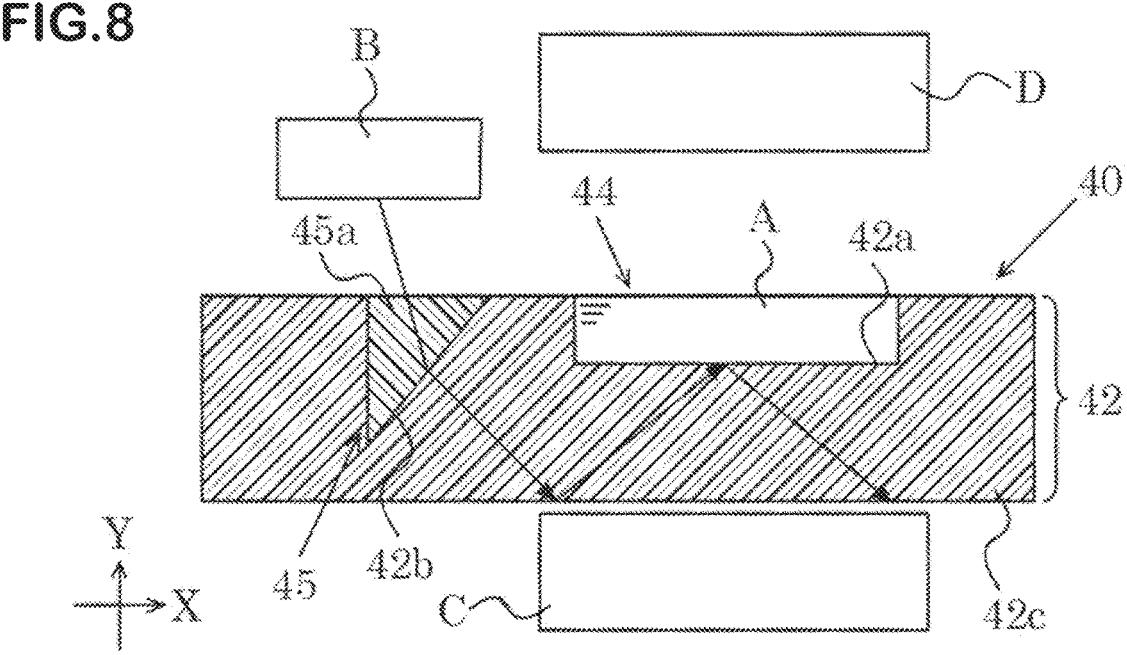
FIG. 8 illustrates an overview of a target substance detection device according to a fifth embodiment.

A target substance detection device according to a fifth embodiment will now be described with reference to FIG. 8. FIG. 8 illustrates an overview of the target substance detection device according to the fifth embodiment.

A detection chip 40 in the fifth embodiment is a modification to the detection chip 10 in the second embodiment. As with the detection chip 10 in the second embodiment, the detection chip 40 includes a light transmissive member 42 having a sensing surface 42a, an upwardly inclined surface 42b, a main body portion 42c, and a sample liquid storage groove 44.

The detection chip 40 in the fifth embodiment has a top surface side notch portion 45 that differs from that of the detection chip 10 according to the second embodiment. Specifically, the top surface side notch portion 45 is filled with a low refractive material 45a having a refractive index lower than the material forming the main body portion 42c.

In the detection chip 40 configured as described above, the top surface side notch portion 45 is filled with the low refractive material 45a, making the top surface of the light transmissive member 42 entirely flat. This prevents the interior of the top surface side notch portion 45 from being contaminated by the sample liquid A that might spill out of the sample liquid storage groove 44 while being introduced therein or discharged therefrom.

Further, even in the case of configuring the top surface side notch portion 45 as described above, the refraction of light at the upwardly inclined surface 42b constituting the interface between the low refractive material 45a and the main body portion 42c made of a high refractive material can be utilized to allow the light applied from the light irradiation unit B to be reflected only once within the main body portion 42c before being directed to the sensing surface 42a, as in the case of the detection chip 10 in the second embodiment.

Other configurations and effects are similar to those of the target substance detection device according to the second embodiment, so the description thereof will be omitted.

Figure 9:
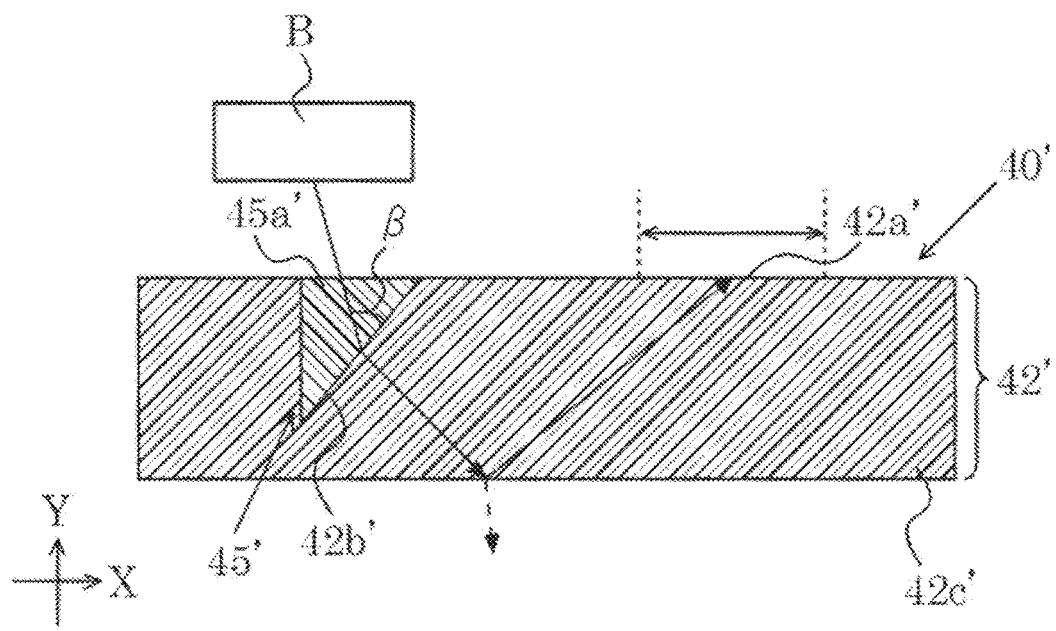
FIG. 9 is a diagram (1) illustrating a modified example.
Figure 10:
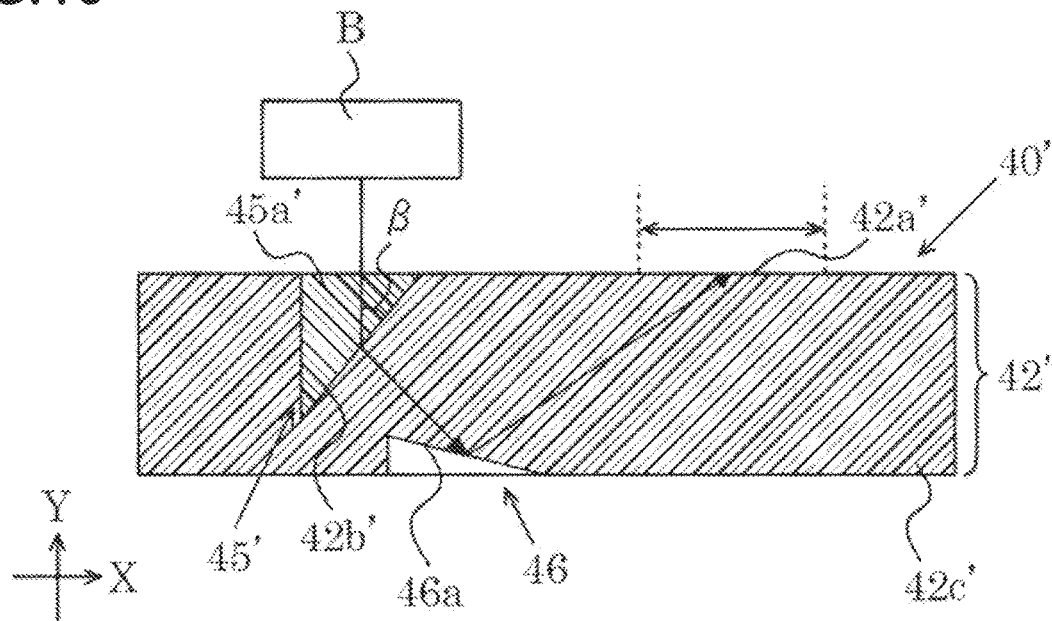
FIG. 10 is a diagram (2) illustrating a modified example.

A supplementary description will now be given of the detection chip 40 in the fifth embodiment in conjunction with modified examples shown in FIGS. 9 and 10. FIGS. 9 and 10 illustrate the modified examples.

As shown in FIG. 9, a detection chip 40' has a sensing surface 42a' as a part of a top surface of a light transmissive member 42', and is provided with a top surface side notch portion 45'.

Here, in the example shown in FIG. 9, as compared to the example shown in FIG. 8, with a light irradiation unit B being configured to apply light to an upwardly inclined surface 42b' of the top surface side notch portion 45' from the side of the top surface of the light transmissive member 42', an angle (angle $\beta$ in FIG. 9) made between the light irradiation direction of the light irradiation unit B and the upwardly inclined surface 42b', as seen as a V-shaped groove angle open on the top surface side of the light transmissive member 42', is set to be a relatively small angle.

With a small angle $\beta$, the light introduced from the upwardly inclined surface 42b' may not be totally reflected at the bottom surface of the light transmissive member 42', with some components transmitted through to the outside of a main body portion 42c' of the light transmissive member 42' (see the dotted arrow in FIG. 9). This state should be taken notice of, since the incident light would not be directed to the rear face under the condition of total reflection.

Thus, the angle $\beta$ should be not smaller than a minimum angle that enables the incident light to fulfill the condition of total reflection at the sensing surface 42a'.

It should be noted that, in the case where the top surface side notch portion 45' is not filled with a low refractive material 45a' as well, if the refractive index of the light transmissive member 42' is not high, the light refracted at the upwardly inclined surface 42b' would not be totally reflected at the bottom surface of the light transmissive member 42', causing some components to be transmitted through to the outside of the light transmissive member 42'.

Further, even in the case where the light incident angle $\beta$ is set to be a relatively small angle, a bottom surface side notch portion 46 may be formed in the bottom surface of the light transmissive member 42' as shown in FIG. 10, the notch portion being formed inclined with respect to the in-plane direction of the bottom surface of the light transmissive member 42' and having a downwardly inclined surface 46a, to thereby direct the reflected light to the sensing surface 42a' set in the top surface under the condition of total reflection. The bottom surface side notch portion 46 can be formed in a similar manner as the top surface side notch portion 45'. Further, the bottom surface side notch portion 46 may be filled with a low refractive material 45a' as with the top surface side notch portion 45'.

Sixth Embodiment

Figure 11:
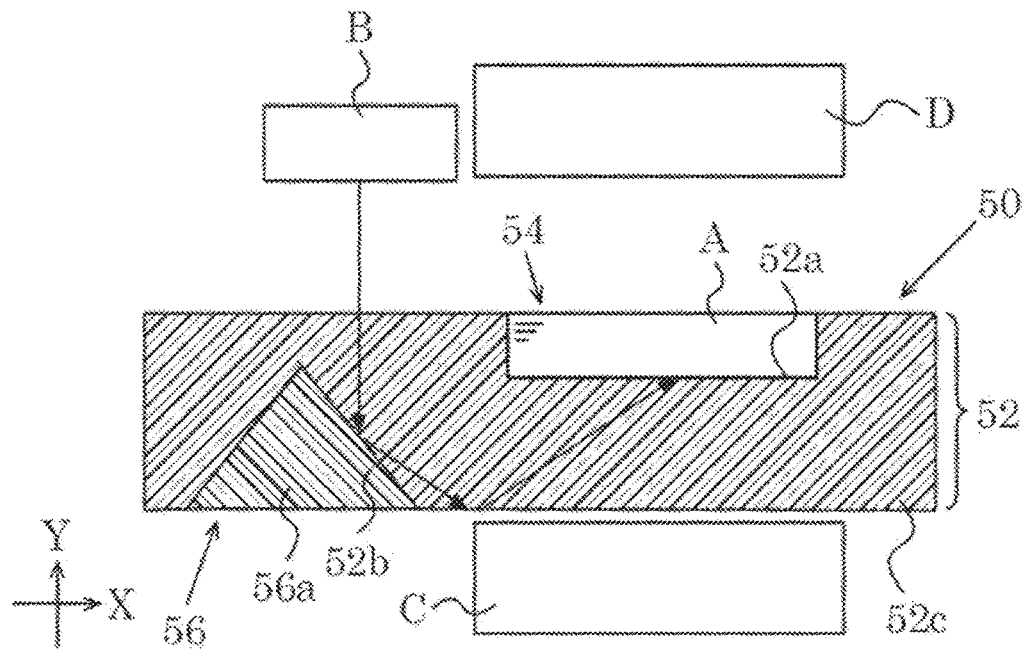
FIG. 11 illustrates an overview of a target substance detection device according to a sixth embodiment.

A target substance detection device according to a sixth embodiment will now be described with reference to FIG. 11. FIG. 11 illustrates an overview of the target substance detection device according to the sixth embodiment.

A detection chip 50 in the sixth embodiment is a modification to the detection chip 20 in the third embodiment.

As shown in FIG. 11, the detection chip 50 in the sixth embodiment has a light transmissive member 52. Unlike the light transmissive member 22 in the third embodiment, the light transmissive member 52 has a sample liquid storage groove 54 formed in the top surface, where a sample liquid A is introduced. The sample liquid storage groove 54 is of a recessed shape in cross section, with its bottom surface constituting a sensing surface 52a.

Further, unlike the light transmissive member 22 in the third embodiment, the light transmissive member 52 has a bottom surface side notch portion 56 formed in the bottom surface and having a downwardly inclined surface 52b. The bottom surface side notch portion 56 is filled, as needed, with a low refractive material 56a having a refractive index lower than the material forming the main body portion 52c.

In the detection chip 50 configured as described above, the bottom surface side notch portion 56 is formed in the bottom surface of the light transmissive member 52, so there is no chance that the interior of the bottom surface side notch portion 56 is contaminated by the sample liquid A that might spill out of the sample liquid storage groove 54 while being introduced therein or discharged therefrom.

When the bottom surface side notch portion 56 is filled with the low refractive material 56a, the downwardly inclined surface 52b is prevented from being exposed to the outside and contaminated by adhesion of dust or the like in the air.

Further, in the bottom surface side notch portion 56 as well, the reflection of light at the downwardly inclined surface 52b can be utilized to cause the light applied from a light irradiation unit B to be reflected one time each at the downwardly inclined surface 52b and the bottom surface before being directed to the sensing surface 52a (second light directing structure).

Other configurations and effects are similar to those of the target substance detection device according to the third embodiment, so the description thereof will be omitted.

Seventh Embodiment

Figure 12:
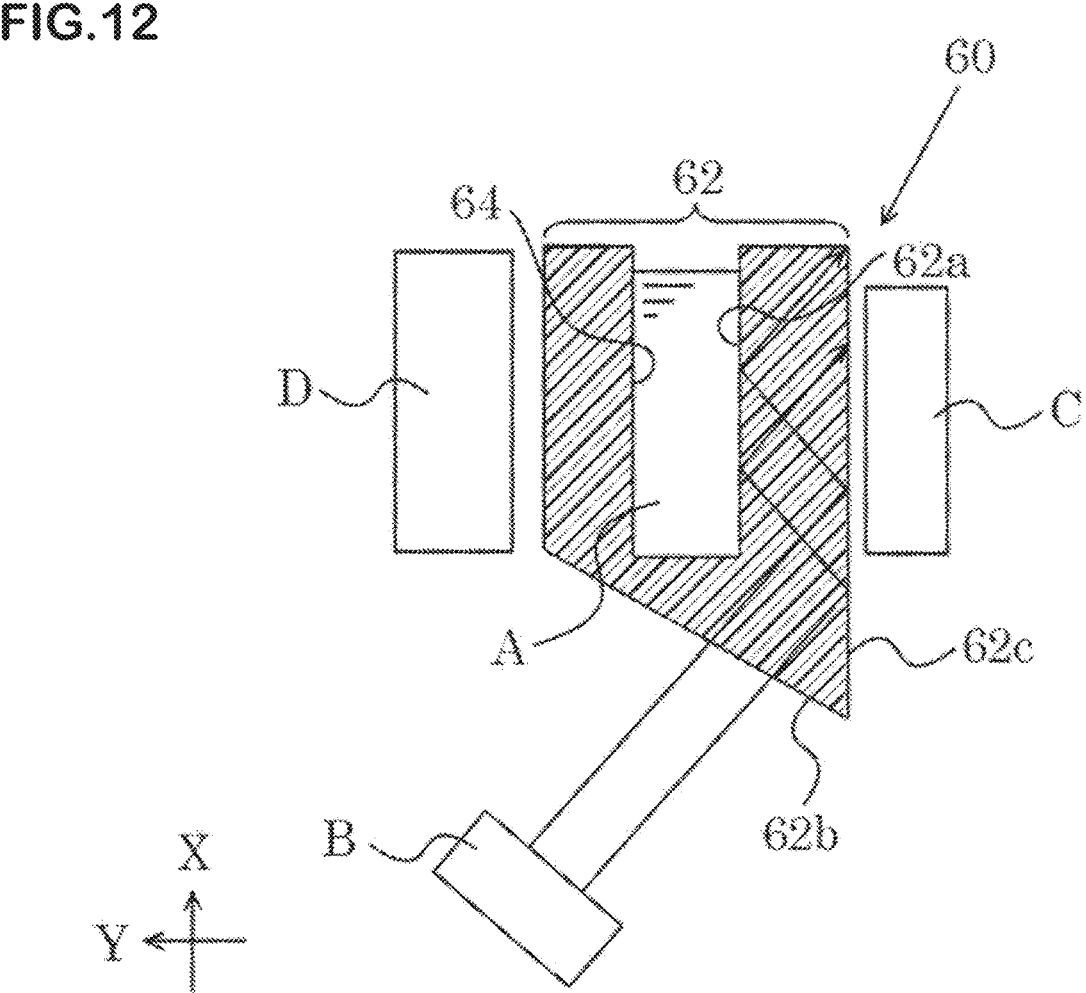
FIG. 12 illustrates an overview of a target substance detection device according to a seventh embodiment.
Figure 13:
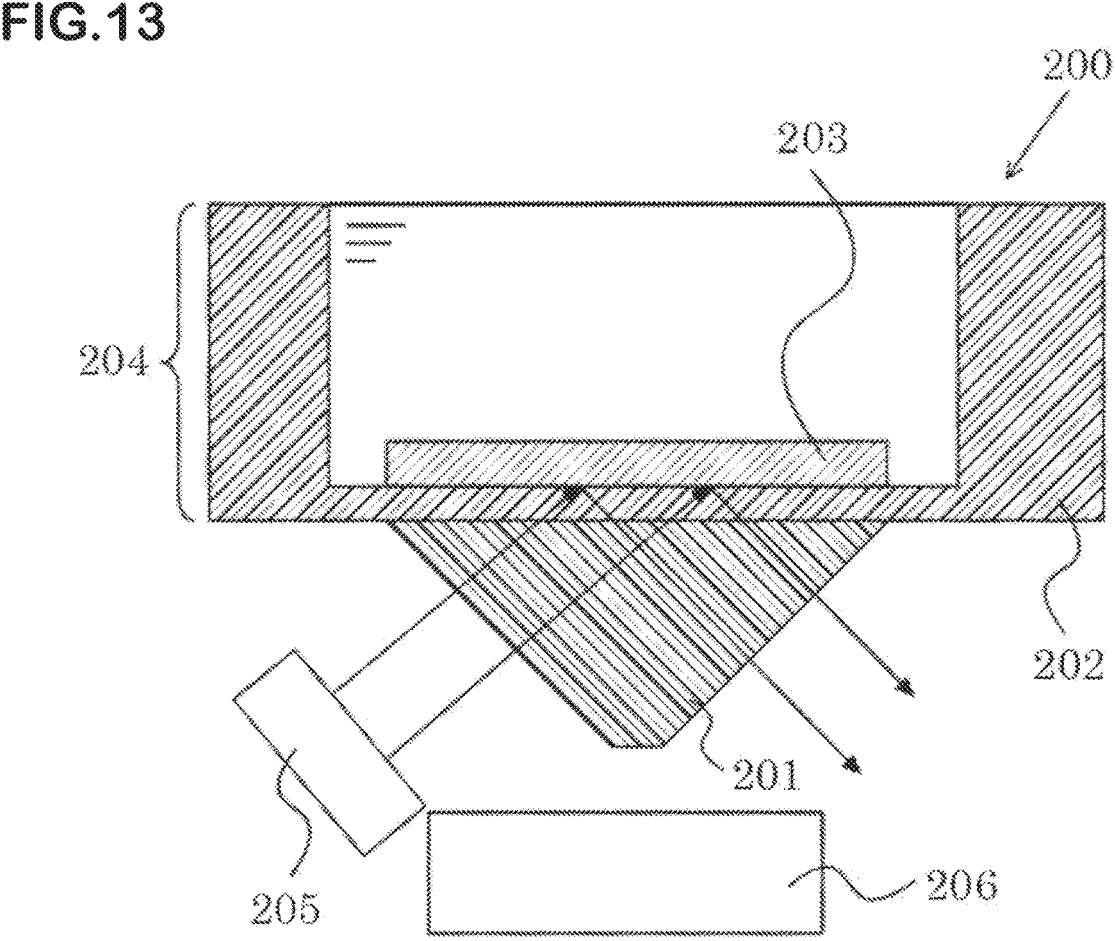
FIG. 13 is a cross-sectional view illustrating an overview of an optical device.
Figure 14:
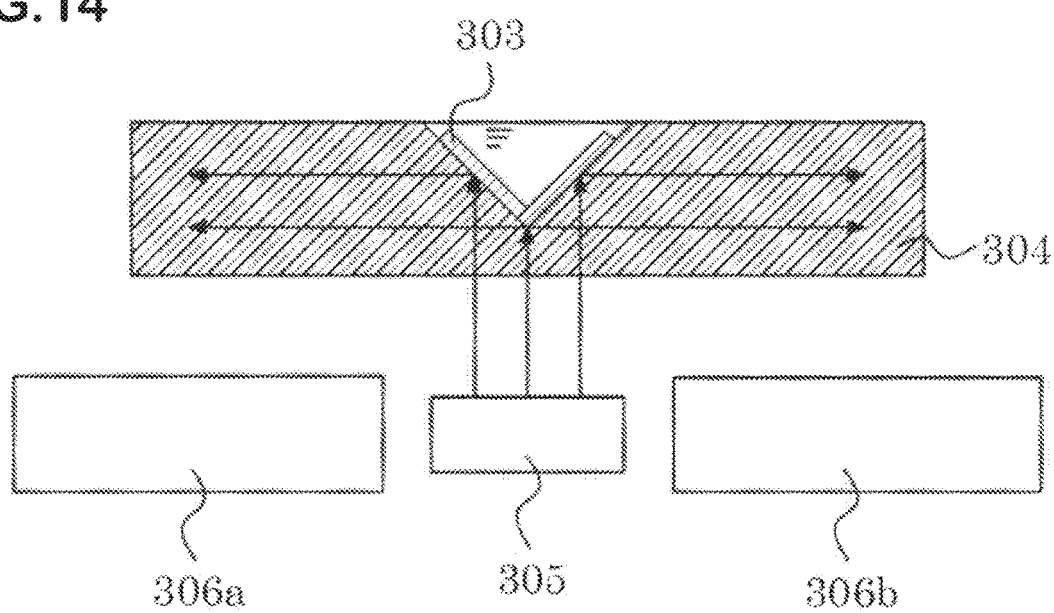
FIG. 14 illustrates how the distance between a front face side of a detection chip and a magnet or the like increases.

A target substance detection device according to a seventh embodiment will now be described with reference to FIG. 12. FIG. 12 illustrates an overview of the target substance detection device according to the seventh embodiment.

The target substance detection device according to the seventh embodiment is a modified example where the target substance detection device according to the first embodiment is slanted 90° during the use. Therefore, in the target substance detection device according to the seventh embodiment, the "top surface" and the "bottom surface" in the target substance detection device according to the first embodiment are located on respective sides and the "side surface" is located on the top. However, a description will be given below by maintaining the positional relationship among the "top surface", the "bottom surface", and the "side surface" in the target substance detection device according to the first embodiment, with a surface of a light transmissive member 62 on the side where a magnetic field application unit C is disposed being regarded as the "bottom surface".

A detection chip 60 in the seventh embodiment is a modification to the detection chip 1 in the first embodiment.

As shown in FIG. 12, the detection chip 60 in the seventh embodiment has a light transmissive member 62. Unlike the light transmissive member 2 in the first embodiment, the light transmissive member 62 has a sample liquid storage groove 64 formed in the side surface to receive a sample liquid A.

The sample liquid storage groove 64 is formed as a drilled groove having a recessed shape in cross section, and one of the surfaces forming the drilled groove that opposes the bottom surface in a closest position constitutes a sensing surface 62a.

In this manner, the target substance detection device and the target substance detection method according to the first invention can be used by changing the orientation of the target substance detection device as desired, as long as it maintains the relative positional relationship among the "top surface", the "bottom surface", and the "side surface".

Other configurations and effects are similar to those of the target substance detection device according to the first embodiment, so the description thereof will be omitted.

The second invention will be described in detail below.

(Target Substance Detection Chip)

A target substance detection chip of the second invention includes an electric field enhancement layer and a light transmissive member.

<Electric Field Enhancement Layer>

The electric field enhancement layer is a layer in which an enhanced electric field is formed on a side of a front face when a rear face is irradiated with light under the condition of total reflection.

The electric field enhancement layer is not particularly limited, and can be selected as appropriate according to the purpose. A well-known surface plasmon excitation layer or waveguide mode excitation layer can be used.

Examples of the surface plasmon excitation layer include a metallic layer containing at least one of gold, silver, platinum, and aluminum.

In the metallic layer, the light applied from the rear face side excites surface plasmon resonance at the front face, so the enhanced electric field is obtained in the vicinity of the front face.

The thickness of the metallic layer may be determined to an optimal value depending on the material constituting the layer and the wavelength of the irradiated light. It is known that this value can be calculated using the Fresnel formula. Generally, in the case of exciting the surface plasmon resonance in the near-ultraviolet to near-infrared region, the thickness of the metallic layer becomes several nanometers to several tens of nanometers.

The method of forming the metallic layer is not particularly limited; it may be any of well-known methods including vapor deposition, sputtering, CVD, PVD, and spin coating. However, when the light transmissive member is made of a plastic or glass material, the metallic layer formed directly on the light transmissive member may be easily peeled off due to poor adhesion.

It is thus preferable, from the standpoint of improving the adhesion, to form an adhesive layer of nickel or chromium on a surface of the light transmissive member and form the metallic layer on the adhesive layer.

In the case of detecting light from a target substance or from a fluorescent substance or the like labeling the target substance, when the target substance or the fluorescent substance or the like approaches the metallic layer, the energy that the target substance or the fluorescent substance or the like has obtained from excitation light may move to the metallic layer, thereby causing a phenomenon called quenching where the luminous efficiency decreases.

In such a case, a covering layer may be formed on the front face of the metallic layer for the purpose of separating the target substance or the fluorescent substance or the like from the front face of the metallic layer. This can suppress the quenching and the degradation of luminous efficiency.

The covering layer is not particularly limited, and can be formed by a transparent layer made of a glass material such as silica glass, an organic polymeric material or the like and having a thickness of several nanometers to several tens of nanometers.

The waveguide mode excitation layer is not particularly limited; it may be a layered structure of a thin film layer made of a metallic or semiconductor material and a dielectric layer made of a light-transmissive dielectric material.

In the waveguide mode excitation layer, the light applied from the rear face side excites the waveguide mode in the dielectric layer, and the enhanced electric field is obtained in the vicinity of the front face.

In the waveguide mode excitation layer, the thin film layer constitutes the layer on the rear face side, and the dielectric layer constitutes the layer on the front face side.

The metallic material is not particularly limited; examples include gold, silver, copper, platinum, and aluminum.

Further, the semiconductor material is not particularly limited; examples include semiconductor materials such as silicon and germanium, and known compound semiconductor materials. Among them, silicon is preferable which is inexpensive and easy to work.

The thickness of the thin film layer may be determined to an optimal value depending on the material constituting the layer and the wavelength of the irradiated light, as with the surface plasmon excitation layer. It is known that this value can be calculated using the Fresnel formula. Generally, when using light in the wavelength range from near ultraviolet to near infrared, the thickness of the thin film layer becomes several nanometers to several hundreds of nanometers.

The light-transmissive dielectric material is not particularly limited; examples include resin materials such as silicon oxide, silicon nitride, and acrylic resin, metallic oxides such as titanium oxide, and metallic nitrides such as aluminum nitride. Among them, silicon oxide is preferable which is easy to produce and chemically stable.

The method of forming the thin film layer and the dielectric layer can be selected as appropriate from well-known methods depending on the materials.

<Light Transmissive Member>

The light transmissive member is of an approximately plate shape as a whole, and has: a support surface capable of supporting the electric field enhancement layer from the rear face side; an inclined surface which is one of an upwardly inclined surface inclined away from the support surface from a top surface toward a bottom surface side with respect to a thickness direction, the top surface being the surface on which the support surface is formed, and a downwardly inclined surface inclined away from the support surface from the bottom surface toward the top surface side with respect to the thickness direction; and a main body portion capable of receiving the light and guiding the light through the interior.

Further, the light transmissive member is configured to have a light directing structure which is one of: a first light directing structure in which the light applied from the top surface side and passed through the upwardly inclined surface is directed, via the main body portion, to the rear face under the condition of total reflection, and a second light directing structure in which the light applied from the top surface side and reflected at the downwardly inclined surface is directed, via the main body portion, to the rear face under the condition of total reflection.

In the light transmissive member, the optically operating surfaces, i.e. the surface to which light is directed and the surface at which light is reflected, are preferably optically smooth.

The light transmissive member serves as an optical prism provided in the conventional detection chips, and also has a role of guiding the light applied from the top surface side of the light transmissive member to the rear face of the electric field enhancement layer, so as to allow the magnetic field application unit to be disposed beneath the position in the target substance detection chip where the electric field enhancement layer is formed.

In other words, the light transmissive member is characterized by having the light directing structure according to which the light applied from the top surface side is directed to the rear face of the electric field enhancement layer under the condition of total reflection.

The material for forming the light transmissive member is not particularly limited, and can be selected as appropriate according to the purpose. Preferable materials include: polystyrene, polycarbonate, cycloolefin, acrylic, and other plastic materials capable of high-volume production by injection molding, and silica glass and other glass materials capable of ensuring high transparency. Among them, polystyrene and cycloolefin are less in autofluorescence and can reduce noise. Polycarbonate realizes a high refractive index and can downsize the device. Acrylic has a high transparency and can suppress attenuation of light while guiding the light.

The thickness of the light transmissive member, although not particularly limited, is preferably from 0.1 mm to 10.0 mm from the standpoints of rigidity, light-guiding performance, and degree of attenuation of magnetism. If the thickness is less than 0.1 mm, cracking or deformation would likely occur, making the member difficult to handle. If the thickness is smaller than the beam diameter of incident light, light will be lost at the time of incidence, and noise light will also occur, so the thickness is preferably greater than the beam diameter. Further, as the magnetic field is applied from the rear face, if the thickness exceeds 10.0 mm, the magnetic field may be attenuated, making it difficult to apply a suitable magnetic field to the front face. The thickness of 5.0 mm or less can considerably suppress the attenuation of the magnetic field.

In the light transmissive member, a sample liquid for which the presence or absence of the target substance is to be verified is introduced into the area where the electric field enhancement layer (as well as the support surface) is formed. The configuration for holding the sample liquid introduced is not particularly limited, and the following configurations may be preferably applied.

Specifically, as one configuration, the light transmissive member may have a part of the top surface constituting the support surface, and a sidewall portion may be erected to surround the support surface so as to form a box-shaped body with the support surface at its bottom. In this configuration, the sample liquid is held in the box-shaped body. For example, the sidewall portion can be formed using a same material as and in a similar manner as the light transmissive member.

As another configuration, the light transmissive member may have a sample liquid storage groove formed in the top surface, the groove having at least a portion constituting the support surface. In this configuration, the sample liquid is held in the sample liquid storage groove. The sample liquid storage groove may be formed by molding at the time of forming a plate-like member constituting the light transmissive member, or may be formed by cutting after the forming of the plate-like member.

When the sample liquid storage groove is formed, the groove may have an arbitrary shape such as a recessed shape, a V shape, or a trapezoidal shape in cross sectional view, although semicircular and other shapes with no flat surface making it unable to form the support surface are excluded.

Further, although the configuration of the sample liquid storage groove is not particularly limited, the groove may have, as the support surface, an inclined support surface inclined away from the inclined surface from the top surface toward the bottom surface side with respect to the thickness direction of the light transmissive member. Having such an inclined support surface as the support surface is advantageous in that the angle of incidence of the light with respect to the inclined surface, which is set to allow the light propagated in the main body portion to be directed to the electric field enhancement layer on the support surface under the condition of total reflection, can be set in a wide range, thereby increasing the degree of freedom of setting.

The target substance detection chip is configured on the assumption that the light is applied from the light irradiation unit disposed on the side of the top surface of the light transmissive member, from the standpoint of avoiding contention with the magnetic field application unit disposed on the side of the bottom surface of the light transmissive member.

That is, in the light directing structure, the traveling direction of the light applied from the side of the top surface of the light transmissive member is changed by the inclined surface, to allow the light to be directed to the rear face of the electric field enhancement layer under the condition of total reflection.

The inclined surface may be formed as a side surface of the light transmissive member, or as a surface constituting a notch portion formed in at least one of the top surface and the bottom surface of the light transmissive member, as long as the inclined surface can function as described above.

The notch portion is formed as at least one of: a top surface side notch portion formed in the top surface of the light transmissive member and having the upwardly inclined surface; and a bottom surface side notch portion formed in the bottom surface of the light transmissive member and having the downwardly inclined surface. The notch portion may be formed by molding at the time of forming a plate-like member constituting the light transmissive member, or may be formed by cutting after the forming of the plate-like member.

Further, in the top surface side notch portion, although the notched portion may be left as a void, it will be difficult to wash off a sample liquid entering in the void, so the notched portion may be filled with a low refractive material having a refractive index lower than that of the main body portion. Filling the top surface side notch portion with the low refractive material can prevent the sample liquid from entering into the top surface side notch portion.

Further, the use of the low refractive material makes it possible to guide the light toward the electric field enhancement layer by utilizing the refraction at the interface between the upwardly inclined surface of the top surface side notch portion and the main body portion.

When filling the top surface side notch portion with the low refractive material, for example, a well-known plastic material having the refractive index of about 1.4 may be filled in the top surface side notch portion, and the main body portion may be formed with a well-known plastic material having the refractive index of about 1.6, to obtain the light transmissive member.

The bottom surface side notch portion is formed in the bottom surface of the light transmissive member, so there will be no chance for the sample liquid introduced on the top surface side to enter into the notched portion.

However, from the standpoint of preventing the downwardly inclined surface of the bottom surface side notch portion from being exposed to the outside and contaminated by adhesion of dust or the like in the air, the bottom surface side notch portion is preferably filled with the low refractive material similarly as the top surface side notch portion.

Meanwhile, when the distance between the light incident position on the inclined surface and the irradiated position on the electric field enhancement layer is long, the light traveling inside the main body portion will be weakened, and the light will also be weakened every time the light is reflected in the main body portion. On the other hand, if the distance between the light incident position and the irradiated position on the electric field enhancement layer is too close, noise due to scattering occurring at the time of incidence of light and the like will be mixed in the optical signals, causing degradation of detection accuracy.

Accordingly, there is a suitable range for the distance between the light incident position on the inclined surface and the irradiated position on the electric field enhancement layer, which is specifically preferably 1.0 mm to 50.0 mm at the shortest distance.

Setting the distance as described above can suppress the weakening of the light traveling in the main body portion, and also suppress noise. The number of times of reflection of the light in the main body portion can be reduced, which can be optimally set to once. In the case where the inclined surface is formed as the downwardly inclined surface as well, it is preferable to decrease the number of times of reflection of the light in the main body portion. The distance is optimally set to allow the light to be reflected only once at the downwardly inclined surface before being directed to the electric field enhancement layer, with the number of times of reflection of the light in the main body portion being set to zero.

As used herein, the term "light transmissive" means that the visible light transmittance is 0.5% or more.

It should be noted that the light directing structure can be set by calculating the route of the light applied from the top surface side of the light transmissive member toward the rear face of the electric field enhancement layer, using a well-known optical calculating method, by giving the conditions of: the angle of inclination of the inclined surface, the angle of irradiation of light to the inclined surface, the quality (refractive index) of the material of the light transmissive member, the distance between the light incident position on the inclined surface and the irradiated position on the electric field enhancement layer, the thickness of the light transmissive member, and so on.

(Target Substance Detection Device)

A target substance detection device in the second invention has the target substance detection chip in the second invention, a light irradiation unit, and a magnetic field application unit, and further includes a light detection unit as needed. For the target substance detection chip, the matters described in relation to the target substance detection chip in the second invention can be applied, so the description will not be repeated.

<Light Irradiation Unit>

The light irradiation unit is disposed on the side of the top surface of the light transmissive member, and is operable to irradiate the rear face of the electric field enhancement layer with light under the condition of total reflection via the light directing structure of the light transmissive member.

The light source of the light irradiation unit is not particularly limited, and can be selected as appropriate according to the purpose. Examples of the light source include a well-known lamp, LED, and laser. The detection performed by the target substance detection device is based on the principle that the light is directed to the rear face of the electric field enhancement layer under the condition of total reflection to form the enhanced electric field in the vicinity of the front face, thereby causing the conjugate comprising the target substance and the magnetic particle to generate an optical signal. The role required for the light irradiation unit to play to this end is simply to irradiate the rear face of the electric field enhancement layer with the light under the condition of total reflection, and any light source can be selected as long as the unit can play such a role.

When a radiation light source such as a lamp or LED is used, a guide unit such as a collimator lens that restricts the irradiated directions of the light to a specific direction may be used to let the irradiated light incident on the light incident portion.

Further, the light to be incident on the light incident portion is preferably monochromatic light having a wavelength that can excite fluorescence with respect to the conjugate. Alternatively, light from a light source having a wide wavelength range, such as a lamp, LED, or the like, may be passed through an optical filter such as a band-pass filter or the like to obtain monochromatic light, for use as the light having only the wavelength that can excite fluorescence.

<Magnetic Field Application Unit>

The magnetic field application unit is disposed on the side of the bottom surface of the light transmissive member.

The magnetic field application unit, although its position is not particularly limited, is preferably disposed immediately beneath the bottom surface of the light transmissive member, in a position opposing the electric field enhancement layer in the target substance detection chip in the thickness direction, from the standpoint of applying a powerful magnetic field to the sample liquid.

The member constituting the magnetic field application unit is not particularly limited as long as it can apply a magnetic field to an area where the sample liquid is introduced. Examples of the member include a well-known permanent magnet and electromagnet.

The sample liquid has well-known magnetic particles such as magnetic beads added thereto. In the presence of the target substance, a conjugate of the target substance and the magnetic particle is formed. If the target substance is less liable to generate fluorescence, a fluorescent labeling substance that is specifically adsorbed to or bound to the target substance to label the target substance may be used. For the fluorescent labeling substance, any of well-known fluorescent substances such as fluorescent dye, quantum dot, fluorescent dyeing agent and the like can be used.

Further, the method of detecting the target substance is not limited to the method of detecting fluorescence; it may be a method of detecting scattered light that is emitted from the conjugate being subject to light intensified in the enhanced electric field.

In the case of detecting the scattered light, if the target substance is less liable to generate scattered light, a light scattering substance that is specifically adsorbed to or bound to the target substance to scatter light may be used. Examples of the light scattering substance include nanoparticles such as polystyrene beads and gold nanoparticles.

The method for binding the target substance, the magnetic particle, the fluorescent labeling substance, and the light scattering substance together is not particularly limited, and any of well-known methods such as physical adsorption, antigen-antibody reaction, DNA hybridization, biotin-avidin bond, chelate bond, amino bond, etc. can be used depending on the substances.

The light from the target substance and the like is generated in the enhanced electric field formed in the vicinity of the front face of the electric field enhancement layer. Thus, in order to detect the optical signals in a short time, the conjugates floating in the sample liquid need to be drawn to the vicinity of the front face of the electric field enhancement layer.

The magnetic field application unit applies the magnetic field to draw the conjugates floating in the sample liquid toward the front face of the electric field enhancement layer, thereby enabling the detection in a short time.

Meanwhile, in order to perform the detection by eliminating noise due to scratches on the front face of the electric field enhancement layer or the like, the states before and after movement of the conjugates in response to application of the magnetic field by the magnetic field application unit may be observed and compared, to perform the detection by eliminating the noise signals included in the optical signals obtained before the movement of the conjugates. According to such detection, while a target substance with the magnetic particle bound thereto moves by the magnetic field application unit, noise caused by scratches on the surface of the detection chip or the like would not move by the magnetic field application unit, so the detection focusing on the moving optical signals can eliminate the noise signals.

In the case of performing such detection, the magnetic field application unit is made to be movable on the side of the bottom surface of the light transmissive member in the direction having a vector component parallel to the in-plane direction of the front face of the electric field enhancement layer while applying the magnetic field, so as to observe and compare the states of the conjugates before and after the movement. The magnetic field application unit may be configured with, for example, the permanent magnet or the like and a sliding member capable of sliding the permanent magnet or the like while supporting the same.

<Light Detection Unit>

The light detection unit is disposed above a surface of the target substance detection chip where the electric field enhancement layer is formed (front face of the electric field enhancement layer), and is capable of detecting an optical signal emitted from a conjugate comprising the target substance in response to the irradiation of light, by using an area in the vicinity of the front face of the electric field enhancement layer as a detection area.

The light detection unit is not particularly limited, and can be selected as appropriate according to the purpose. Examples include well-known photodetectors such as a well-known photodiode, photomultiplier, and the like, and well-known imaging devices such as a CCD image sensor, CMOS image sensor, and the like.

(Target Substance Detection Method)

A target substance detection method in the second invention includes at least a light irradiation step and a magnetic field application step, and further includes a light detection step as needed.

<Light Irradiation Step>

The light irradiation step, which is performed on the target substance detection chip in the second invention, is a step of irradiating the rear face of the electric field enhancement layer with light under the condition of total reflection, from the side of the top surface of the light transmissive member via the light directing structure in the light transmissive member.

For performing the light irradiation step, the matters described in relation to the light irradiation unit in the target substance detection device in the second invention can be applied, so the description will not be repeated.

<Magnetic Field Application Step>

The magnetic field application step is a step of applying a magnetic field from the side of the bottom surface of the light transmissive member by the magnetic field application unit. In this step, suitably, the magnetic field application unit, in the state of applying the magnetic field, is moved in the direction having a vector component parallel to the in-plane direction of the electric field enhancement layer.

For performing the magnetic field application step, the matters described in relation to the magnetic field application unit in the target substance detection device in the second invention can be applied, so the description will not be repeated.

<Light Detection Step>

The light detection step is a step of detecting an optical signal emitted from the conjugate in response to the irradiation of light.

For performing the light detection step, the matters described in relation to the light detection unit in the target substance detection device in the second invention can be applied, so the description will not be repeated.

First Embodiment

Exemplary configurations of the target substance detection chip in the second invention will be specifically described below with reference to the drawings.

Figure 15:
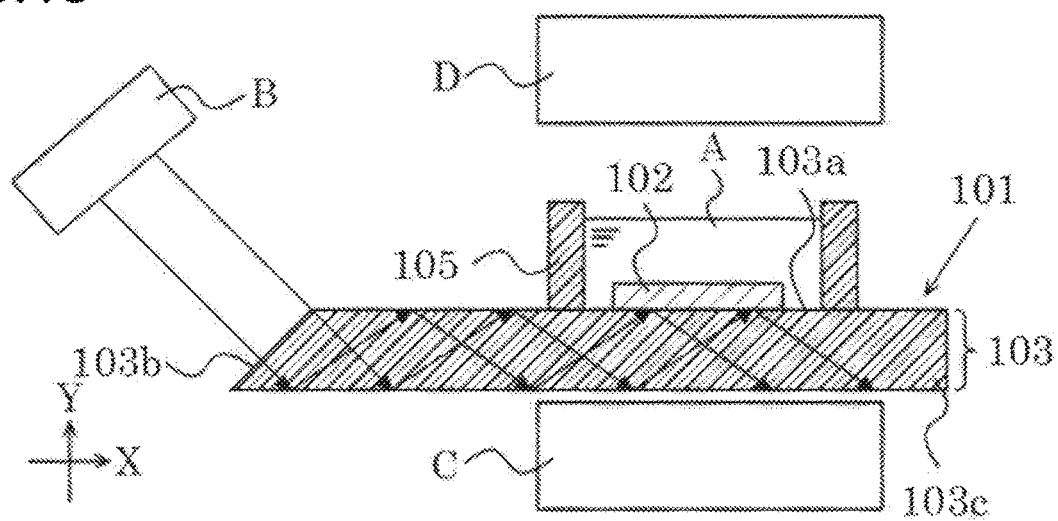
FIG. 15 illustrates an overview of a target substance detection chip according to a first embodiment.

Firstly, a target substance detection chip according to a first embodiment will be described with reference to FIG. 15. FIG. 15 illustrates an overview of the target substance detection chip according to the first embodiment.

As shown in FIG. 15, the target substance detection chip 101 according to the first embodiment has an electric field enhancement layer 102 and a light transmissive member 103.

The electric field enhancement layer 102 is formed as a layer in which an enhanced electric field is formed on a side of a front face when a rear face is irradiated with light under the condition of total reflection.

The light transmissive member 103 is of a plate shape, and has a top surface a part of which constitutes a support surface 103a capable of supporting the electric field enhancement layer 102 from the rear face side, a side surface constituting an upwardly inclined surface 103b, and a body constituting a main body portion 103c which is capable of receiving light from the top surface and guiding the light through the interior.

On the top surface of the light transmissive member 103, a sidewall portion 105 is erected around the support surface 103a to form a box-shaped body with the support surface 103a at its bottom, and a sample liquid A is introduced into this box-shaped body.

Here, the upwardly inclined surface 103b formed as a side surface of the light transmissive member 103 is inclined away from the support surface 103a from the top surface toward the bottom surface side with respect to a thickness direction Y of the light transmissive member 103. Light applied from a light irradiation unit B, disposed opposite to the upwardly inclined surface 103b, is directed into the main body portion 103c obliquely with respect to a lengthwise direction X orthogonal to the thickness direction Y of the light transmissive member 103.

The light incident in the main body portion 103c is propagated through the interior of the main body portion 103c in the lengthwise direction X while being reflected a plurality of number of times at the top surface and the bottom surface of the main body portion 103c.

The light propagated through the interior of the main body portion 103c is totally reflected at the position of the rear face of the electric field enhancement layer 102 on the support surface 103a, thereby forming an enhanced electric field in the vicinity of the front face of the electric field enhancement layer 102 (first light directing structure).

When configuring the target substance detection device with the target substance detection chip 101, as shown in FIG. 15, the light irradiation unit B is disposed on the side of the top surface of the light transmissive member 103, in a position opposing the upwardly inclined surface 103b as a side surface of the light transmissive member 103. A magnetic field application unit C is disposed immediately beneath the bottom surface of the light transmissive member 103 in a position opposing the electric field enhancement layer 102 in the thickness direction Y. A light detection unit D is disposed on the side of the top surface of the light transmissive member 103.

The magnetic field application unit C applies a magnetic field to draw a conjugate comprising a target substance and a magnetic particle, floating in the sample liquid A, to the vicinity of the front face of the electric field enhancement layer 102 where the conjugate is capable of emitting an optical signal, thereby enabling the measurement in a short time. Further, when the magnetic field application unit C is caused to slide in the lengthwise direction X, for example, to detect optical signals before and after the sliding, then only the conjugates following the sliding of the magnetic field application unit C can be detected, thereby enabling the detection eliminating the noise signals caused by scratches on the front face of the electric field enhancement layer 102 and the like.

The light detection unit D is capable of detecting light from the conjugate in the vicinity of the front face of the electric field enhancement layer 102.

In the target substance detection device configured using the target substance detection chip 101 as described above, the magnetic field application unit C can be placed in a position beneath the bottom surface of the light transmissive member 103 at a short distance from the electric field enhancement layer 102, and the light applied from the light irradiation unit B can be directed to the rear face of the electric field enhancement layer 102 under the condition of total reflection, without causing contention in placement positions between the light irradiation unit B and the magnetic field application unit C. This eliminates the need to use a powerful magnetic field application member capable of applying a magnetic field from a position far away from the electric field enhancement layer 102, thereby enabling the target substance detection device to be manufactured compactly and inexpensively, without being increased in scale.

Second Embodiment

Figure 16:
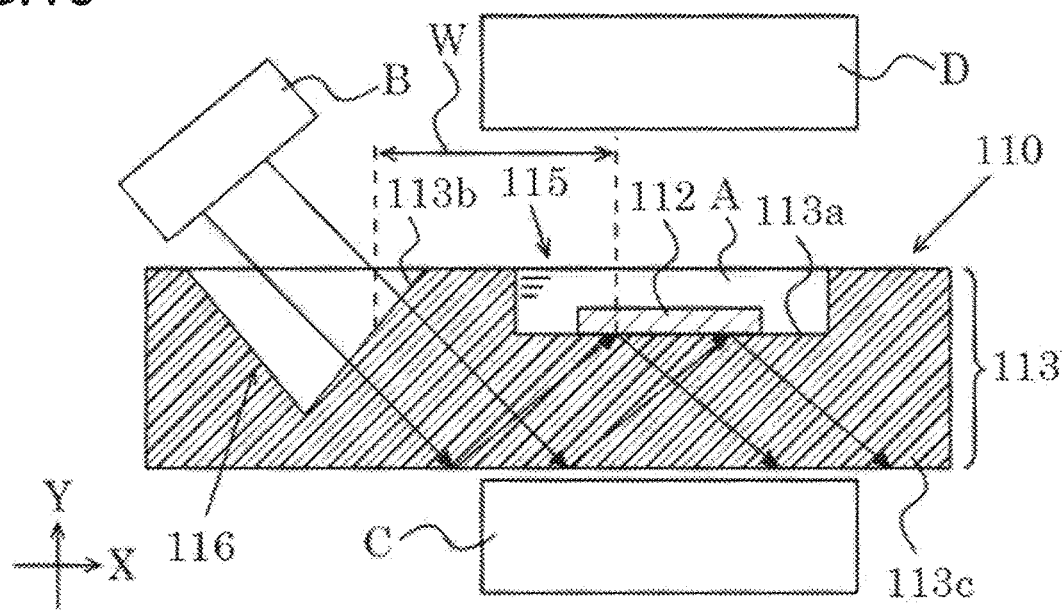
FIG. 16 illustrates an overview of a target substance detection chip according to a second embodiment.

A target substance detection chip according to a second embodiment will now be described with reference to FIG. 16. FIG. 16 illustrates an overview of the target substance detection chip according to the second embodiment.

As shown in FIG. 16, the target substance detection chip 110 according to the second embodiment has an electric field enhancement layer 112 and a light transmissive member 113.

Unlike the light transmissive member 103 in the first embodiment, the light transmissive member 113 has a sample liquid storage groove 115 formed in the top surface for receiving a sample liquid A. The sample liquid storage groove 115 is of a recessed shape in cross section, with its bottom surface constituting a support surface 113a for the electric field enhancement layer 112.

Further, unlike the light transmissive member 103 in the first embodiment, the light transmissive member 113 has a top surface side notch portion 116 formed in the top surface and having an upwardly inclined surface 113b. The top surface side notch portion 116 is of an approximately V shape in cross section.

Here, the upwardly inclined surface 113b is inclined away from the support surface 113a from the top surface toward the bottom surface side with respect to a thickness direction Y of the light transmissive member 113. Light applied from a light irradiation unit B, disposed opposite to the upwardly inclined surface 113b, is directed into the main body portion 113c obliquely with respect to a lengthwise direction X orthogonal to the thickness direction Y of the light transmissive member 113.

A distance W between the light incident position on the upwardly inclined surface 113b and the irradiated position on the electric field enhancement layer 112 is suitably 1.0 mm to 50.0 mm at the shortest distance.

The light incident in the main body portion 113c is reflected at the bottom surface of the main body portion 113c the smallest possible number of times, preferably only once, before being directed to the rear face of the electric field enhancement layer 112 on the support surface 113a. The light is totally reflected at the position of the rear face, and forms an enhanced electric field in the vicinity of the front face of the electric field enhancement layer 112 (first light directing structure).

When configuring the target substance detection device with the target substance detection chip 110, as shown in FIG. 16, the light irradiation unit B is disposed on the side of the top surface of the light transmissive member 113, in a position opposing the upwardly inclined surface 113b.

In the target substance detection chip 110 configured as described above, the distance W between the light incident position on the upwardly inclined surface 113b and the irradiated position on the electric field enhancement layer 112 becomes shorter than the distance between the light incident position on the upwardly inclined surface 103b (side surface of the light transmissive member 103) and the irradiated position on the electric field enhancement layer 102 in the target substance detection chip 101 in the first embodiment. This reduces the attenuation of the light traveling through the main body portion 113c.

Other configurations and effects are similar to those of the target substance detection chip 101 and the target substance detection device in the first embodiment, so the description thereof will be omitted.

Figure 17:
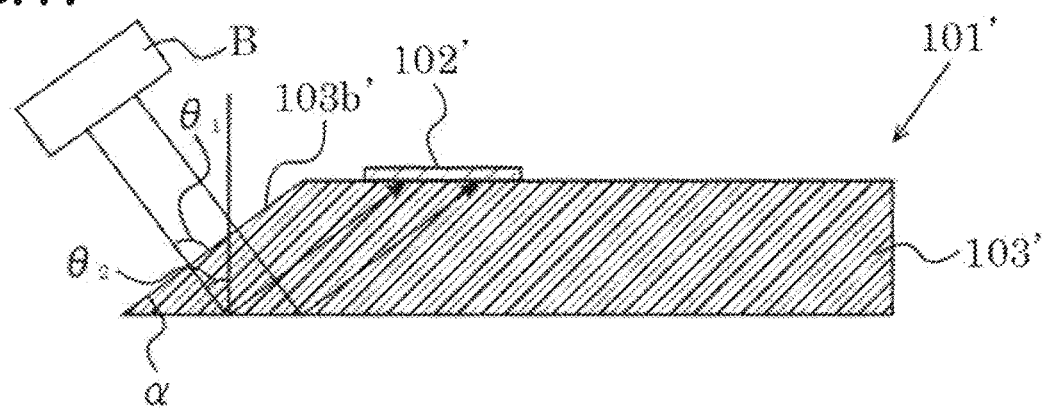
FIG. 17 is a diagram (1) illustrating an exemplary incident angle of light.
Figure 18:
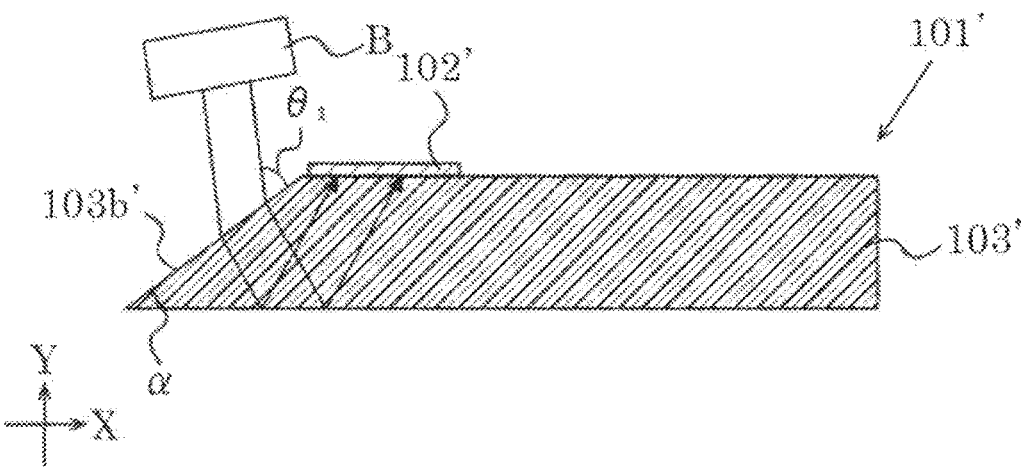
FIG. 18 is a diagram (2) illustrating an exemplary incident angle of light.
Figure 19:
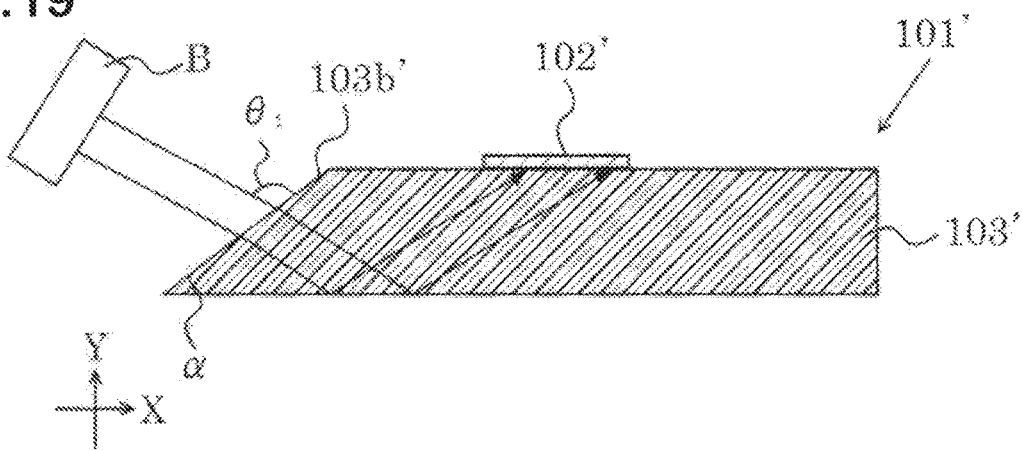
FIG. 19 is a diagram (3) illustrating an exemplary incident angle of light.

Referring now to FIGS. 17 to 19, a supplementary description will be given of the incident angle of light on the upwardly inclined surface 103b of the light transmissive member 103 in the target substance detection chip 101 according to the first embodiment. FIGS. 17 to 19 illustrate exemplary incident angles of light.

As shown in FIG. 17, a target substance detection chip 101' has an electric field enhancement layer 102' disposed on a top surface of a light transmissive member 103'.

In the example shown in FIG. 17, with a side surface of the light transmissive member 103' constituting an upwardly inclined surface 103b', a light irradiation direction of a light irradiation unit B is set such that the light enters the light transmissive member 103' in a normal direction, or, in the direction perpendicular to the upwardly inclined surface 103b'. An angle $\theta_1$ made between the light irradiation direction of the light irradiation unit B and the upwardly inclined surface 103b', as seen as a V-shaped groove angle open on the top surface side of the light transmissive member 103', is set to be 90°.

When the light is incident in the direction perpendicular to the upwardly inclined surface 103b' with $\theta_1$ being 90°, no refraction of light occurs at the upwardly inclined surface 103b'. Further, an angle $\theta_2$ made between the thickness direction Y of the light transmissive member 103' and the light incident direction on the bottom surface of the light transmissive member 103' becomes equal to an angle α made between the bottom surface and the side surface (upwardly inclined surface 103b') of the light transmissive member 103' ($\theta_2$=α). As these phenomena occur irrespective of the material of the light transmissive member 103', it is possible to uniquely specify the light reflected position in the main body portion of the light transmissive member 103' on the basis of the setting of the angle α, to thereby simplify the setting of the electric field enhancement layer in the target substance detection chip and the settings of the optical system in the target substance detection device. In the example shown in FIG. 17, if the angle α is too small, $\theta_2$ also becomes too small, in which case the incident light will not be totally reflected at the bottom surface of the light transmissive member 103', with some components transmitted through to the outside of the light transmissive member 103'. This state should be taken notice of, since the incident light would not be directed to the rear face under the condition of total reflection. On the other hand, if the angle α is too large, it is difficult for the light to enter from the top surface side. Therefore, the angle α is preferably from 50° to 80°.

In the example shown in FIG. 18, the angle $\theta_1$ made between the light irradiation direction of the light irradiation unit B and the upwardly inclined surface 103b', as seen as a V-shaped groove angle open on the top surface side of the light transmissive member 103', is set to be less than 90°.

When the light is incident in the upwardly inclined surface 103b' with $\theta_1$ being less than 90°, the light refracted at the upwardly inclined surface 103b' is reflected at the bottom surface of the light transmissive member 103' and guided to the top surface.

If the light incident angle $\theta_1$ is too small relative to 90°, the light refracted at the upwardly inclined surface 103b' will not be totally reflected at the bottom surface of the light transmissive member 103', with some components transmitted through to the outside of the light transmissive member 103'. This state should be taken notice of, since the incident light would not be directed to the rear face under the condition of total reflection.

It should also be noted that if $\theta_1$ is too small relative to 90°, the position on the top surface to which the reflected light is directed becomes too close to the side surface (upwardly inclined surface 103b'), making it difficult to form the electric field enhancement layer 102' in this position on the top surface.

Accordingly, when θ1 is set to be less than 90°, its lower limit is preferably an angle with which the angle made between the light irradiation direction of the light irradiation unit B and the lengthwise direction X of the light transmissive member 103' on the electric field enhancement layer 102' side becomes 90° or more, although it depends on the angle α.

In the example shown in FIG. 19, the angle $\theta_1$ made between the light irradiation direction of the light irradiation unit B and the upwardly inclined surface 103b', as seen as a V-shaped groove angle open on the top surface side of the light transmissive member 103', is set to exceed 90°.

When the light is incident in the upwardly inclined surface 103b' with $\theta_1$ exceeding 90°, the light refracted at the upwardly inclined surface 103b' is reflected at the bottom surface of the light transmissive member 103' and guided to the top surface. This is preferable because, at the time of reflection, the light refracted at the upwardly inclined surface 103b' would likely be totally reflected at the bottom surface of the light transmissive member 103'.

However, it should be noted that if $\theta_1$ is too large compared to 90°, the position on the top surface to which the reflected light is guided will be farther from the upwardly inclined surface 103b', leading to an increase in size of the target substance detection chip 101'.

When $\theta_1$ is set to be an angle exceeding 90°, its upper limit is an angle with which the light irradiation direction of the light irradiation unit B will not reach parallel to the lengthwise direction X of the target substance detection chip 101', although it depends on the angle α.

While the supplementary description has been given of the incident angle of light on the upwardly inclined surface 103b of the light transmissive member 103 in the target substance detection chip 101 according to the first embodiment by referring to FIGS. 17 to 19, $\theta_1$ is also applicable to the upwardly inclined surface 113b of the light transmissive member 113 in the target substance detection chip 110 according to the second embodiment.

However, it should be noted that when setting $\theta_1$ to an angle exceeding 90°, if $\theta_1$ is too large relative to 90°, a portion of the light transmissive member 113 that constitutes a surface of the V-shaped top surface side notch portion 116 opposing the upwardly inclined surface 113b will become an obstacle to light irradiation, thereby imposing a constraint on the angle setting of $\theta_1$. In contrast, there would likely be no such constraint when setting $\theta_1$ to be equal to or less than 90°.

Third Embodiment

Figure 20:
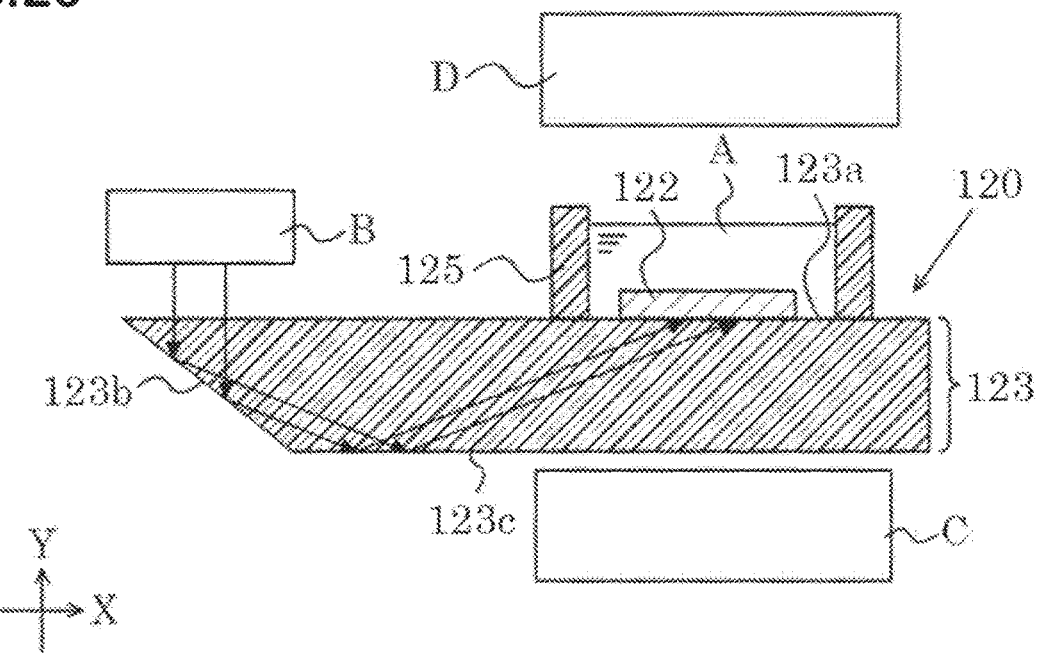
FIG. 20 illustrates an overview of a target substance detection chip according to a third embodiment.

A target substance detection chip according to a third embodiment will now be described with reference to FIG. 20. FIG. 20 illustrates an overview of the target substance detection chip according to the third embodiment.

As shown in FIG. 20, the target substance detection chip 120 according to the third embodiment has an electric field enhancement layer 122 and a light transmissive member 123.

The light transmissive member 123 is of a plate shape, and has a top surface a part of which constitutes a support surface 123a capable of supporting the electric field enhancement layer 122 from the rear face side, and a body constituting a main body portion 123c capable of receiving light from the top surface and guiding the light through the interior. On the top surface of the light transmissive member 123, a sidewall portion 125 is erected around the support surface 123a to form a box-shaped body with the support surface 123a at its bottom, and a sample liquid A is introduced into this box-shaped body.

Unlike the light transmissive member 103 in the first embodiment, the light transmissive member 123 has a side surface constituting a downwardly inclined surface 123b that is inclined away from the support surface 123a from the bottom surface toward the top surface side with respect to a thickness direction Y, and the light is applied to the top surface of the light transmissive member 123 in a position opposite to the side surface in the thickness direction Y.

Here, the light applied from the light irradiation unit B onto the top surface is introduced into the main body portion 123c, and it is reflected at the downwardly inclined surface 123b and the bottom surface in this order, for example, as illustrated in the figure. The light is then totally reflected at a position of the rear face of the electric field enhancement layer 122 on the support surface 123a, and forms an enhanced electric field in the vicinity of the front face of the electric field enhancement layer 122 (second light directing structure).

In this manner, the target substance detection chip 120 according to the third embodiment configured such that the side surface of the light transmissive member 123 faces the bottom surface side, different from the target substance detection chip 101 in the first embodiment in which the side surface of the light transmissive member 123 faces the top surface side, is also capable of producing the enhanced electric field as with the target substance detection chip 101 in the first embodiment.

Fourth Embodiment

Figure 21:
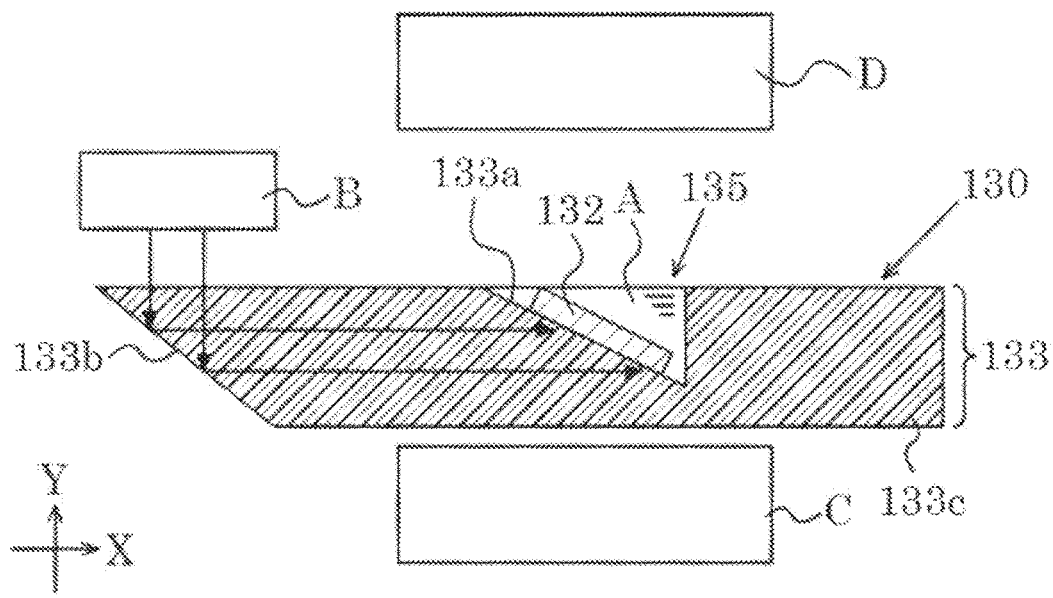
FIG. 21 illustrates an overview of a target substance detection chip according to a fourth embodiment.

A target substance detection chip according to a fourth embodiment will now be described with reference to FIG. 21. FIG. 21 illustrates an overview of the target substance detection chip according to the fourth embodiment.

As shown in FIG. 21, the target substance detection chip 130 according to the fourth embodiment has an electric field enhancement layer 132 and a light transmissive member 133.

Unlike the light transmissive member 103 in the first embodiment, the light transmissive member 133 has a sample liquid storage groove 135 formed in the top surface for receiving a sample liquid A. The sample liquid storage groove 135 is of an approximately V shape in cross section, and its surface forming a side of the groove with the approximately V-shaped cross section constitutes a support surface 133a for the electric field enhancement layer 132.

Here, unlike the light transmissive member 103 in the first embodiment, the light transmissive member 133 has a side surface constituting a downwardly inclined surface 133b that is inclined away from the support surface 133a from the bottom surface toward the top surface side with respect to a thickness direction Y, and the light is applied to the top surface of the light transmissive member 133 in a position opposite to the side surface in the thickness direction Y.

A light irradiation unit B irradiates the top surface of the light transmissive member 133 with light in the thickness direction Y, i.e. in the direction perpendicular to the top surface. The light incident in the main body portion 133c is reflected only once at the downwardly inclined surface 133b, without being reflected at the top surface or the bottom surface of the main body portion 133c while being propagated through the interior of the main body portion 133c in a lengthwise direction X. The light is then totally reflected at the position of the rear face of the electric field enhancement layer 132 on the support surface 133a, and forms an enhanced electric field in the vicinity of the front face of the electric field enhancement layer 132 (second light directing structure).

In the target substance detection chip 130 configured as described above, the light incident in the main body portion 133c is guided toward the rear face of the electric field enhancement layer 132 on the support surface 133a, without being reflected at the top or bottom surface of the main body portion 133c. This suppresses degradation of the light caused by reflection at the top and bottom surfaces.

Other configurations and effects are similar to those of the target substance detection chip 101 and the target substance detection device in the first embodiment, so the description thereof will be omitted.

Fifth Embodiment

Figure 22:
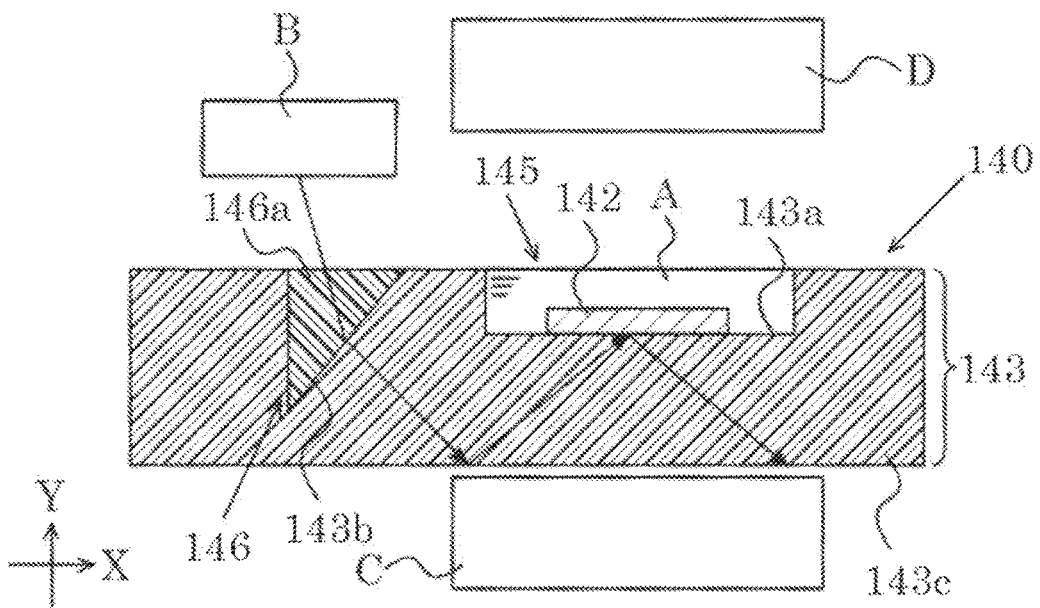
FIG. 22 illustrates an overview of a target substance detection chip according to a fifth embodiment.

A target substance detection chip according to a fifth embodiment will now be described with reference to FIG. 22. FIG. 22 illustrates an overview of the target substance detection chip according to the fifth embodiment.

The target substance detection chip 140 according to the fifth embodiment is a modification to the target substance detection chip 110 according to the second embodiment. As with the target substance detection chip 110 according to the second embodiment, the target substance detection chip 140 includes an electric field enhancement layer 142, and a light transmissive member 143 having a support surface 143a, an upwardly inclined surface 143b, a main body portion 143c, and a sample liquid storage groove 145.

The target substance detection chip 140 according to the fifth embodiment has a top surface side notch portion 146 that differs from that of the target substance detection chip 110 according to the second embodiment. Specifically, the top surface side notch portion 146 is filled with a low refractive material 146a having a refractive index lower than the material forming the main body portion 143c.

In the target substance detection chip 140 configured as described above, the top surface side notch portion 146 is filled with the low refractive material 146a, making the top surface of the light transmissive member 143 entirely flat. This prevents the interior of the top surface side notch portion 146 from being contaminated by the sample liquid A that might spill out of the sample liquid storage groove 145 while being introduced therein or discharged therefrom.

Further, even in the case of configuring the top surface side notch portion 146 as described above, the refraction of light at the upwardly inclined surface 143b constituting the interface between the low refractive material 146a and the main body portion 143c made of a high refractive material can be utilized to allow the light applied from the light irradiation unit B to be reflected only once within the main body portion 143c before being directed to the rear face of the electric field enhancement layer 142, as in the case of the target substance detection chip 110 according to the second embodiment.

Other configurations and effects are similar to those of the target substance detection chip 110 and the target substance detection device in the second embodiment, so the description thereof will be omitted.

Figure 23:
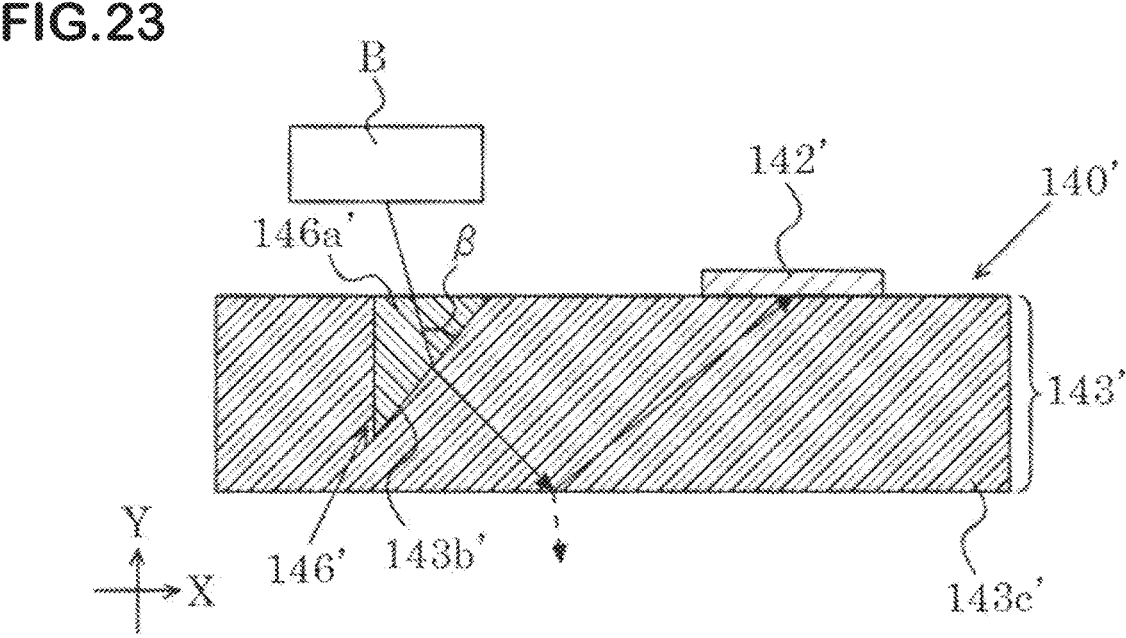
FIG. 23 is a diagram (1) illustrating a modified example.
Figure 24:
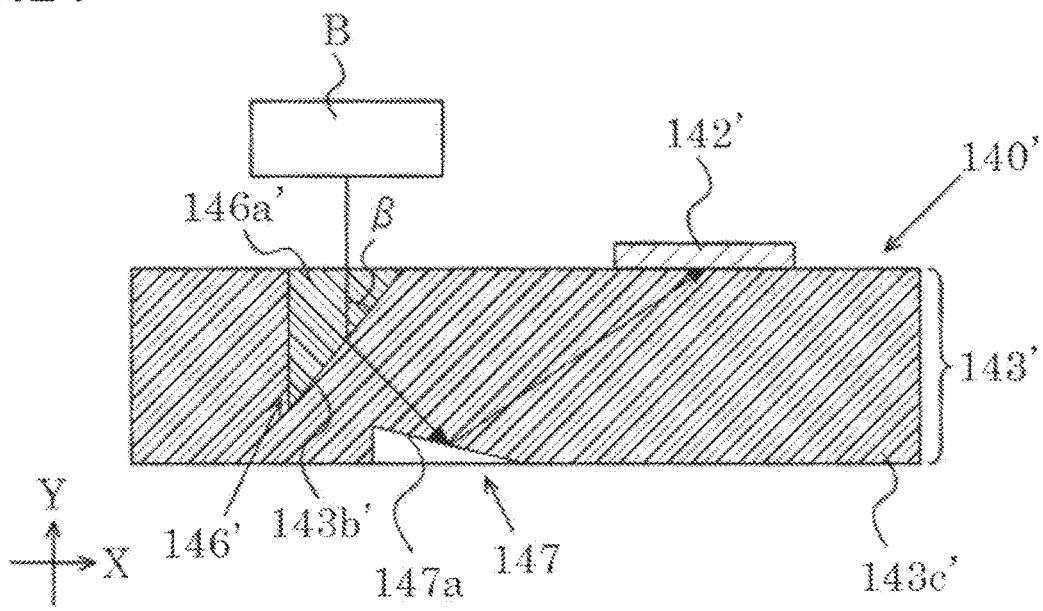
FIG. 24 is a diagram (2) illustrating a modified example.

A supplementary description will now be given of the target substance detection chip 140 according to the fifth embodiment in conjunction with modified examples shown in FIGS. 23 and 24. FIGS. 23 and 24 illustrate the modified examples.

As shown in FIG. 23, a target substance detection chip 140' has an electric field enhancement layer 142' disposed on a top surface of a light transmissive member 143', and also has a top surface side notch portion 146' in the top surface.

Here, in the example shown in FIG. 23, as compared to the example shown in FIG. 22, with a light irradiation unit B being configured to apply light to an upwardly inclined surface 143b' of the top surface side notch portion 146' from the side of the top surface of the light transmissive member 143', an angle (angle β in FIG. 23) made between the light irradiation direction of the light irradiation unit B and the upwardly inclined surface 143b', as seen as a V-shaped groove angle open on the top surface side of the light transmissive member 143', is set to be a relatively small angle.

With a small angle β, the light introduced from the upwardly inclined surface 143b' may not be totally reflected at the bottom surface of the light transmissive member 143', with some components transmitted through to the outside of a main body portion 143c' of the light transmissive member 143' (see the dotted arrow in FIG. 23). This state should be taken notice of, since the incident light would not be directed to the rear face under the condition of total reflection.

Thus, the angle β should be not smaller than a minimum angle that enables the incident light to fulfill the condition of total reflection at the rear face.

It should be noted that, in the case where the top surface side notch portion 146' is not filled with a low refractive material 146a' as well, if the refractive index of the light transmissive member 143' is not high, the light refracted at the upwardly inclined surface 143b' would not be totally reflected at the bottom surface of the light transmissive member 143', causing some components to be transmitted through to the outside of the light transmissive member 143'.

Further, even in the case where the light incident angle β is set to be a relatively small angle, a bottom surface side notch portion 147 may be formed in the bottom surface of the light transmissive member 143' as shown in FIG. 24, the notch portion being formed inclined with respect to the in-plane direction of the bottom surface of the light transmissive member and having a downwardly inclined surface 147a, to thereby direct the reflected light to the electric field enhancement layer 142' disposed on the top surface under the condition of total reflection. The bottom surface side notch portion 147 can be formed in a similar manner as the top surface side notch portion 146'. Further, the bottom surface side notch portion 147 may be filled with a low refractive material as with the top surface side notch portion 146'.

Sixth Embodiment

Figure 25:
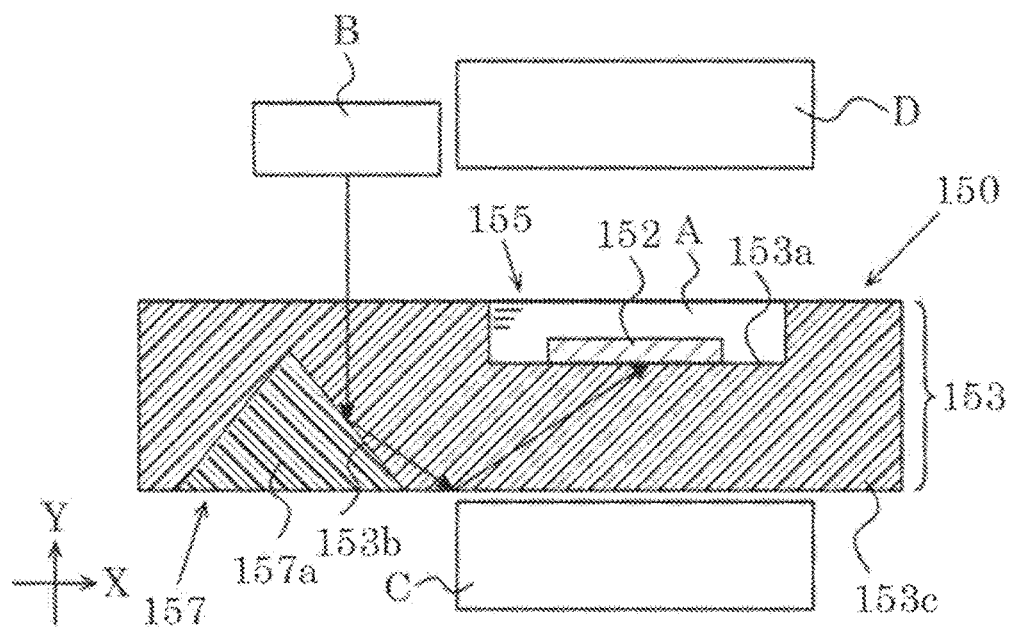
FIG. 25 illustrates an overview of a target substance detection chip according to a sixth embodiment.

A target substance detection chip according to a sixth embodiment will now be described with reference to FIG. 25. FIG. 25 illustrates an overview of the target substance detection chip according to the sixth embodiment.

The target substance detection chip 150 according to the sixth embodiment is a modification to the target substance detection chip 120 according to the third embodiment. As shown in FIG. 25, the target substance detection chip 150 according to the sixth embodiment has an electric field enhancement layer 152 and a light transmissive member 153.

Unlike the light transmissive member 123 in the third embodiment, the light transmissive member 153 has a sample liquid storage groove 155 formed in the top surface for receiving a sample liquid A. The sample liquid storage groove 155 is of a recessed shape in cross section, with its bottom surface constituting a support surface 153a for the electric field enhancement layer 152.

Further, unlike the light transmissive member 123 in the third embodiment, the light transmissive member 153 has a bottom surface side notch portion 157 formed in the bottom surface and having a downwardly inclined surface 153b. The bottom surface side notch portion 157 is filled, as needed, with a low refractive material 157a having a refractive index lower than the material forming a main body portion 153c.

In the target substance detection chip 150 configured as described above, the bottom surface side notch portion 157 is formed in the bottom surface of the light transmissive member 153, so there is no chance that the interior of the bottom surface side notch portion 157 is contaminated by the sample liquid A that might spill out of the sample liquid storage groove 155 while being introduced therein or discharged therefrom.

When the bottom surface side notch portion 157 is filled with the low refractive material 157a, the downwardly inclined surface 153b is prevented from being exposed to the outside and contaminated by adhesion of dust or the like in the air.

Further, in the bottom surface side notch portion 157 as well, the reflection of light at the downwardly inclined surface 153b can be utilized to cause the light applied from the light irradiation unit B to be reflected one time each at the downwardly inclined surface 153b and the bottom surface before being directed to the rear face of the electric field enhancement layer 152 (second light directing structure).

Other configurations and effects are similar to those of the target substance detection chip 120 and the target substance detection device in the third embodiment, so the description thereof will be omitted.

The third invention will be described in detail below.

(Target Substance Detection Chip)

A target substance detection chip in the third invention has a light transmissive substrate, and has an electric field enhancement layer and an uneven structure imparting layer as needed.

<Light Transmissive Substrate>

The light transmissive substrate is a member that transmits light.

The light transmissive substrate is not particularly limited, and can be selected as appropriate according to the purpose. For example, a well-known light transmissive substrate such as a glass substrate or a plastic substrate can be used.

In the case of forming an uneven surface on the light transmissive substrate, the method of forming the uneven surface is not particularly limited. Examples include well-known methods such as injection molding, nanoimprint, and etching.

As used herein, the term "light transmissive" means that the visible light transmittance is 0.5% or more.

<Electric Field Enhancement Layer>

The electric field enhancement layer is a layer in which, in response to one surface irradiated with light under the condition of total reflection, an enhanced electric field is formed on the other surface.

The electric field enhancement layer is not particularly limited, and can be selected as appropriate according to the purpose. A well-known surface plasmon excitation layer or waveguide mode excitation layer can be used.

Examples of the surface plasmon excitation layer include a metallic layer containing at least one of gold, silver, platinum, and aluminum.

In the metallic layer, the light applied to the one surface excites surface plasmon resonance on the other surface, so the enhanced electric field is obtained on the other surface.

The thickness of the metallic layer may be determined to an optimal value depending on the material constituting the layer and the wavelength of the irradiated light. It is known that this value can be calculated using the Fresnel formula. Generally, in the case of exciting the surface plasmon resonance in the near-ultraviolet to near-infrared region, the thickness of the metallic layer becomes several nanometers to several tens of nanometers.

The method of forming the metallic layer is not particularly limited; it may be any of well-known methods including vapor deposition, sputtering, CVD, PVD, and spin coating. However, when the light transmissive substrate is made of a plastic or glass material, the metallic layer formed directly on the light transmissive substrate may be easily peeled off due to poor adhesion.

It is thus preferable, from the standpoint of improving the adhesion, to form an adhesive layer of nickel or chromium on a surface of the light transmissive substrate and form the metallic layer on the adhesive layer.

In the case of detecting light emitted from a target substance or from a labeling substance labeling the target substance, when the target substance or the labeling substance approaches the metallic layer, the energy that the target substance or the fluorescent material or the like has obtained from excitation light may move to the metallic layer, thereby causing a phenomenon called quenching where the luminous efficiency decreases.

In such a case, for the purpose of separating the target substance or the labeling substance from the front face of the metallic layer, a covering layer may be formed on the front face of the metallic layer, which can suppress the quenching and the degradation of luminous efficiency.

The covering layer is not particularly limited, and can be formed by a transparent layer made of a glass material such as silica glass, an organic polymeric material or the like and having a thickness of several nanometers to several tens of nanometers.

The waveguide mode excitation layer is not particularly limited; it may be a layered structure of a thin film layer made of a metallic or semiconductor material and a dielectric layer made of a light-transmissive dielectric material.

In the waveguide mode excitation layer, the light applied to the one surface excites the waveguide mode in the dielectric layer, and the enhanced electric field is obtained on the other surface.

In the waveguide mode excitation layer, the thin film layer constitutes the layer on the one surface side, and the dielectric layer constitutes the other surface side.

The metallic material is not particularly limited; it may be, for example, gold, silver, copper, platinum, aluminum, or the like.

Further, the semiconductor material is not particularly limited. Examples of the material include semiconductor materials such as silicon and germanium, and known compound semiconductor materials. Among them, silicon is preferable which is inexpensive and easy to work.

The thickness of the thin film layer may be determined to an optimal value depending on the material constituting the layer and the wavelength of the irradiated light, as with the surface plasmon excitation layer. It is known that this value can be calculated using the Fresnel formula. Generally, when using light in the wavelength range from near ultraviolet to near infrared, the thickness of the thin film layer becomes several nanometers to several hundreds of nanometers.

The light-transmissive dielectric material is not particularly limited. Examples of the material include resin materials such as silicon oxide, silicon nitride, and acrylic resin, metallic oxides such as titanium oxide, and metallic nitrides such as aluminum nitride. Among them, silicon oxide is preferable which is easy to produce and chemically stable.

The method of forming the thin film layer and the dielectric layer can be selected as appropriate from well-known methods depending on the materials.

<Uneven Structure Imparting Layer>

The uneven structure imparting layer has the light transmissive property and has one surface constituting an uneven surface.

The material for forming the uneven structure imparting layer is not particularly limited, and can be selected as appropriate according to the purpose. Examples of the material include well-known light transmissive materials such as acrylic resin, polyester resin, polyolefin resin, general plastic, engineering plastic, super-engineering plastic, synthetic polymeric resin, natural resin, UV-curable resin, thermosetting resin, and thermoplastic resin.

The method of forming the uneven surface is not particularly limited, and can be selected as appropriate according to the purpose. Examples of the forming method include well-known methods such as etching, electron beam lithography, laser lithography, laser interferometry, cutting, and self-organizing methods. Another available method uses a mold or die shaped by the aforementioned forming method. To transfer the uneven pattern of the mold or die, molten materials are poured into the mold or die, cured, and then separated from the mold or die.

<Layer Configuration>

The target substance detection chip may be configured with: the light transmissive substrate by itself; the light transmissive substrate with the uneven structure imparting layer stacked thereon; the light transmissive substrate with the electric field enhancement layer stacked thereon; or the light transmissive substrate with the electric field enhancement layer and the uneven structure imparting layer stacked thereon.

In the case where the target substance detection chip is not provided with the electric field enhancement layer, the detection chip is configured such that, with its surface opposite to the surface on which the uneven structure is formed as a rear face, an evanescent field can be existent on a front face in response to light applied from the rear face side under the condition of total reflection.

In the case where the target substance detection chip has the electric field enhancement layer formed thereon, the detection chip is configured such that the enhanced electric field can be existent on the front face in response to the light applied from the rear face side under the condition of total reflection.

Specific examples of the layer configuration will be described later with reference to the drawings.

<Uneven Structure>

The target substance detection chip is formed to have an uneven structure configured with a plurality of projections arranged periodically on the front face, for the purposes of preventing adsorption of a conjugate comprising the target substance with at least a magnetic particle bound thereto.

The uneven structure is formed on the basis of an uneven surface that is formed either on the light transmissive substrate or on the uneven structure imparting layer.

The shape of the projection is not particularly limited; it may be, for example, a prismatic, trapezoidal, semicircular, or semi-elliptical shape in cross sectional view in the lateral axis direction.

Although the uneven structure is not particularly limited, it is preferably a periodic structure in which, when the conjugate is estimated to have a diameter of about 1 µm, for example, all or some of the projections have a height of 1 µm to 1.55 µm and the pitch interval between the adjacent projections is either a shorter interval of 0.45 µm to 0.55 µm or a longer interval of 1.45 µm to 1.55 µm.

Specific examples of the uneven structure will be described later with reference to the drawings.

First Embodiment

A first embodiment of the third invention will be described with reference to the drawings. The first embodiment is an embodiment of the target substance detection chip of the third invention.

Figure 26:
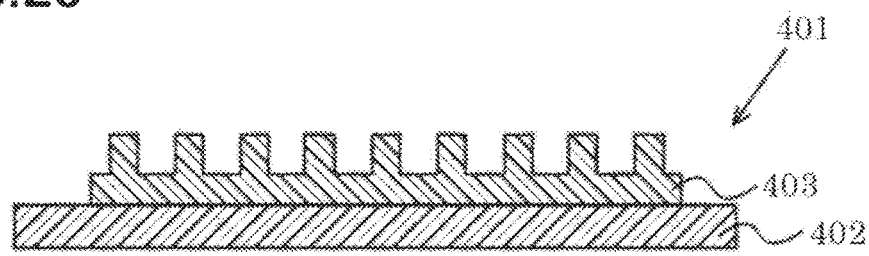
FIG. 26 illustrates a schematic configuration of a first embodiment.

As shown in FIG. 26, a target substance detection chip 401 has a light transmissive substrate 402 and an uneven structure imparting layer 403. FIG. 26 illustrates a schematic configuration of the first embodiment.

The light transmissive substrate 402 has a smooth surface, on which the uneven structure imparting layer 403 is stacked.

The light transmissive substrate 402 may have a sidewall portion formed to create a box-shaped body with the smooth surface at the bottom, and the box-shaped body may be used as a liquid storage portion to store therein a sample liquid for which the presence of a target substance is to be verified.

As used herein, the term "smooth" means optically smooth, and the "smooth" surface has a surface accuracy of $\lambda/2$ or less.

The uneven structure imparting layer 403 is stacked on the light transmissive substrate 402, and has an uneven surface as a surface opposite to the surface on the light transmissive substrate 402 side. The uneven structure imparting layer 403 is fixed onto the light transmissive substrate 402 in a manner not particularly limited, for example by adhesion, bonding, fusion, pasting, or the like.

The target substance detection chip 401 has an uneven structure formed on the front face by the uneven surface of the uneven structure imparting layer 403.

Further, the target substance detection chip 401 having the uneven structure imparting layer 403 stacked on the light transmissive substrate 402 is configured such that, with the surface opposite to the surface on which the uneven structure is formed as a rear face, when the light is applied to the uneven structure imparting layer 403 from the rear face side under the condition of total reflection, the evanescent field is generated in the vicinity of the front face.

Figure 27A:
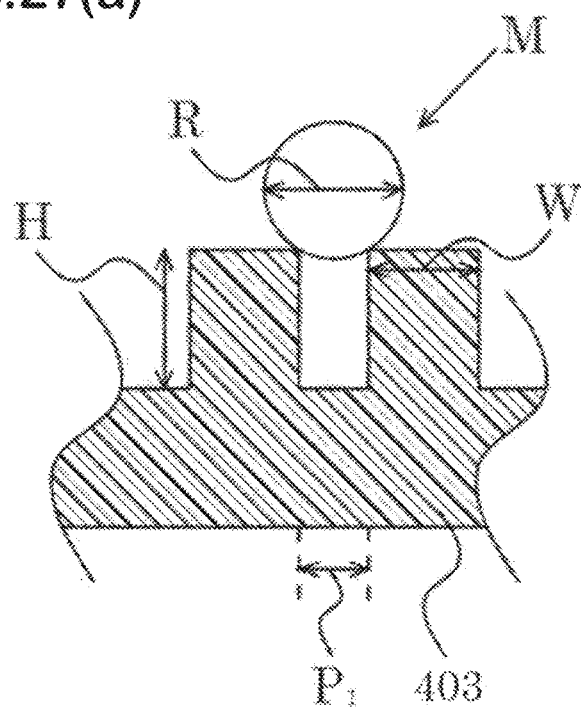
FIG. 27($a$) is a diagram (1) illustrating how an uneven structure suppresses adsorption of conjugates.
Figure 27B:
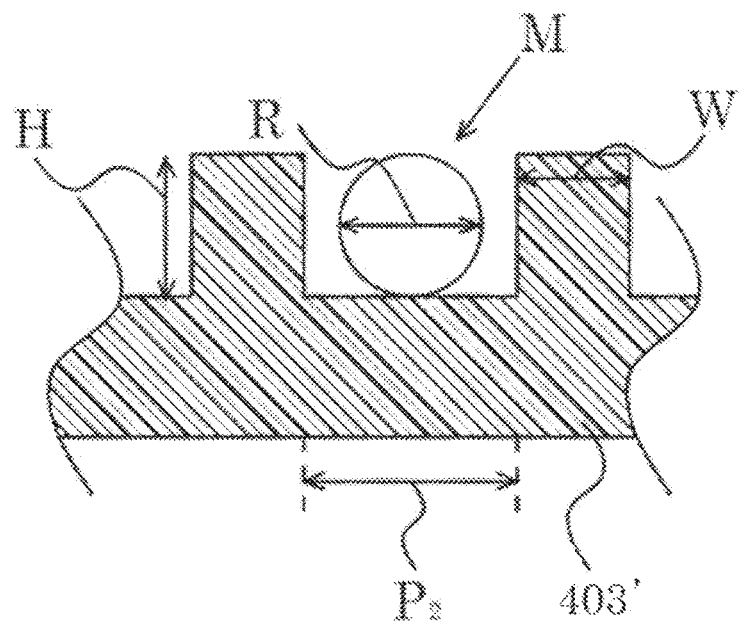

The uneven structure, formed by a plurality of projections arranged periodically, has a role of preventing the conjugates in the sample liquid introduced onto the front face from being adsorbed to the front face. A description will now be given of how the uneven structure prevents adsorption of the conjugates with reference to FIGS. 27(a) and 27(b). FIGS. 27(a) and 27(b) each illustrate how the uneven structure prevents the adsorption of the conjugates.

As shown in FIG. 27(a), in the uneven structure, a pitch interval $P_1$ between the adjacent projections is set to 9/20 R to 11/20 R with respect to the particle diameter R of a conjugate M, or, to be shorter than the particle diameter R of the conjugate M. Further, a height H of the projection is set to 1 R to 2 µm with respect to the particle diameter R of the conjugate M, and a width W of the projection is set to 9/20 R to 3/2 R with respect to the particle diameter R of the conjugate M.

Such an uneven structure reduces the contact area and decreases the work of adhesion, thereby suppressing adsorption of the conjugate M to the front face (the uneven surface of the uneven structure imparting layer 403) of the target substance detection chip 401.

Here, from the standpoint of observing the movement of the target substance in response to application of the magnetic field, the uneven structure can be suitably used in the case where a conjugate M is regarded as having a spherical shape with a diameter of about 1 µm, for example. A conceivable example is a case where the target substance is a protein having a size of several nanometers, a fluorescent dye having a size of several nanometers is used as the labeling substance, and a magnetic particle having a particle diameter of 1 µm is used as the magnetic particulate. In this example, the target substance and the labeling substance each have a size not larger than one hundredth of the magnetic particulate, so the conjugate M can be regarded as a sphere having a particle diameter of 1 µm. Forming the uneven structure can improve the convenience of the target substance detection chip 401.

In the case of such an example, the pitch interval $P_1$ is preferably 0.45 µm to 0.55 µm, the height H is preferably 1 µm to 1.55 µm, and the width W is preferably 0.45 µm to 1.5 µm.

Figure 29:
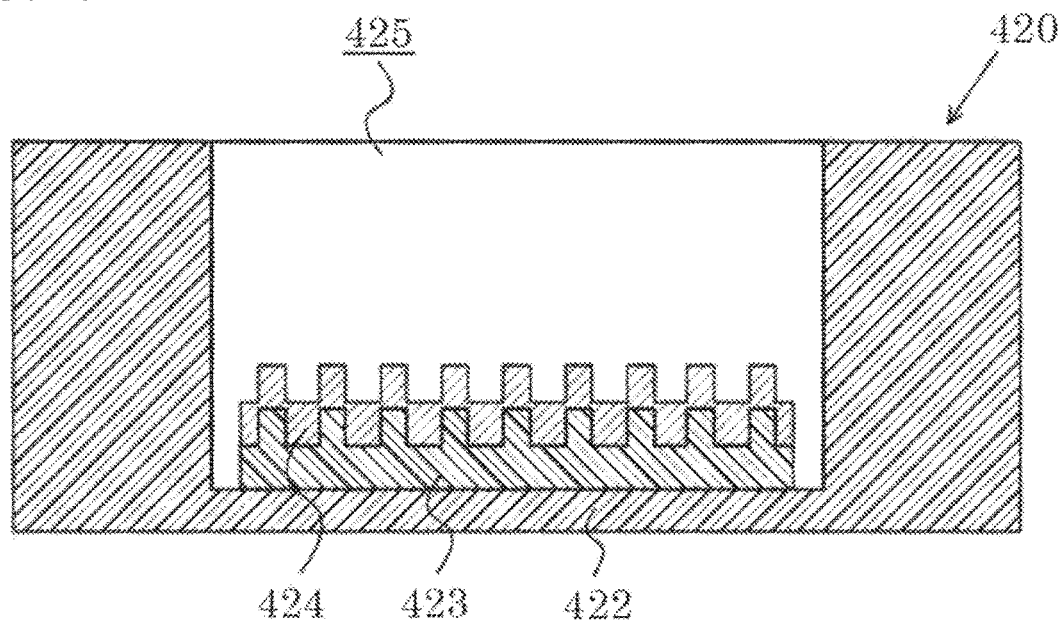
FIG. 29 illustrates a schematic configuration of a third embodiment.

While the pitch interval $P_1$ in the example shown in FIG. 27(a) was set to be shorter than the particle diameter R of the conjugate M, a pitch interval $P_2$ may be set, as shown in FIG. 27(b), to 29/20 R to 31/20 R with respect to the particle diameter R of the conjugate M, or, to be longer than the particle diameter R of the conjugate M. Assuming that a conjugate having a diameter of about 1 μm is to be detected, the pitch interval $P_2$ is preferably 1.45 μm to 1.55 μm.

With such an uneven structure, although a piece of conjugate may be adhered and immobilized, the work of adhesion for a plurality of pieces of conjugates to be adhered, immobilized, and aggregated can be reduced, thereby suppressing adsorption of the conjugates M to the front face (the uneven surface of the uneven structure imparting layer 403') of the target substance detection chip 401.

The height H and the width W are similar to those described in conjunction with FIG. 27(a).

While the projections in FIGS. 27(a) and 27(b) have a quadrangular prism shape in cross section, the projections may have a trapezoidal, semicircular, semi-elliptical, or other shape in cross section. For the pitch interval $P_1$, $P_2$, height H, and width W for the projections of these shapes, the above-described settings can be applied with respect to the maximum length in the projections.

As described above, in the target substance detection chip 401 according to the first embodiment, the uneven structure can suppress adsorption of the conjugates.

Further, in the target substance detection chip 401 according to the first embodiment, the conjugates can be moved, with no regulation against application of the magnetic field to the front face. Therefore, the chip can be used in detecting a target substance using the magnetic particles, and the target substance detection device using this chip can be manufactured compactly and inexpensively.

While the target substance detection chip 401 according to the first embodiment has the uneven structure imparting layer 403 stacked on the light transmissive substrate 402, an uneven surface similar to the uneven surface in the uneven structure imparting layer 403 may be formed on the light transmissive substrate 402, so that the light transmissive substrate by itself can constitute the target substance detection chip.

Second Embodiment

A second embodiment of the third invention will be described with reference to the drawing. The second embodiment is an embodiment of the target substance detection chip of the third invention.

Figure 28:
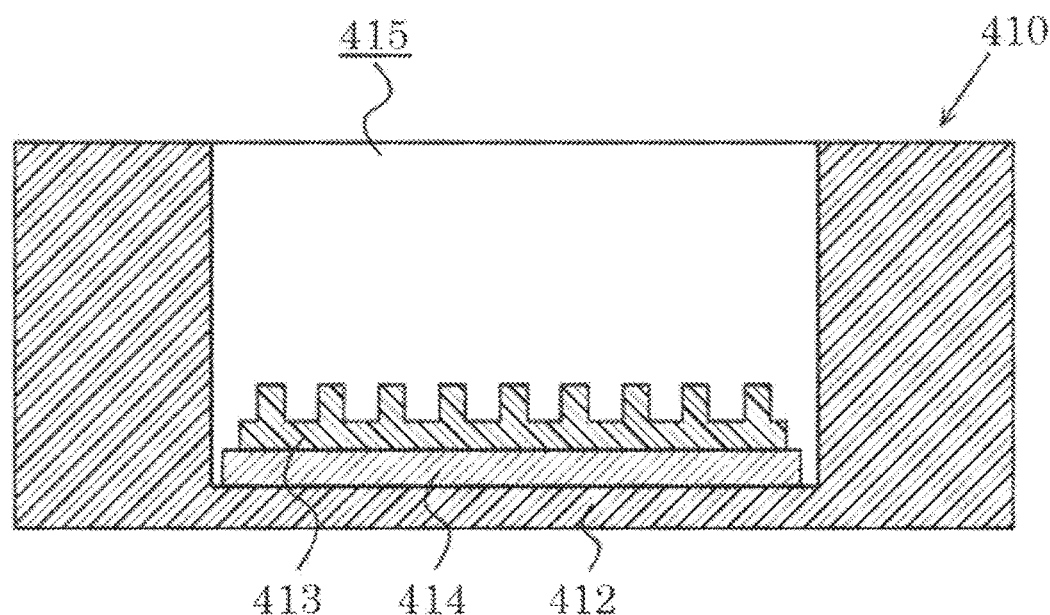
FIG. 28 illustrates a schematic configuration of a second embodiment.

As shown in FIG. 28, a target substance detection chip 410 has a light transmissive substrate 412, an uneven structure imparting layer 413, and an electric field enhancement layer 414. FIG. 28 illustrates a schematic configuration of the second embodiment.

The light transmissive substrate 412 has a smooth surface, on which the electric field enhancement layer 414 is stacked. The light transmissive substrate 412 also has a sidewall portion formed to create a box-shaped body with the smooth surface at the bottom, and the box-shaped body is used as a liquid storage portion 415 to store therein a sample liquid for which the presence of a target substance is to be verified.

The electric field enhancement layer 414 is a layer in which, when one surface is irradiated with light under the condition of total reflection, an enhanced electric field is formed on the other surface. It is a smooth layer stacked on the smooth surface of the light transmissive substrate 412. The electric field enhancement layer 414 is configured in accordance with a well-known surface plasmon excitation layer or waveguide mode excitation layer.

The uneven structure imparting layer 413 is stacked on the electric field enhancement layer 414, and has an uneven surface as a surface opposite to the surface on the electric field enhancement layer 414 side. The uneven structure imparting layer 413 is fixed onto the electric field enhancement layer 414 in a manner not particularly limited, for example by adhesion, bonding, fusion, pasting, or the like. In the case of using a well-known surface plasmon excitation layer as the electric field enhancement layer 414, in order for the enhanced electric field to exist in the vicinity of the front face of the target substance detection chip 410, the uneven structure imparting layer 413 needs to be thin enough to allow the enhanced electric field to reach the front face. Thus, in this case, the thinnest portion of the uneven structure imparting layer 413, i.e. the portion where no projection is formed, has a thickness of preferably 200 nm or less. A preferable way of forming such a thin uneven structure imparting layer 413 is to apply a resist on the electric field enhancement layer 414, and expose and develop the resist to impart the uneven structure. On the other hand, in the case of using a well-known waveguide mode excitation layer as the electric field enhancement layer 414, the uneven structure imparting layer 413 and the aforementioned dielectric layer in the electric field enhancement layer 414 together form a waveguide layer. Therefore, the enhanced electric field can be existent in the vicinity of the front face of the target substance detection chip 410 with no particular restriction on the thickness of the uneven structure imparting layer 413.

The target substance detection chip 410 has an uneven structure formed on the front face by the uneven surface of the uneven structure imparting layer 413 constituting the outermost layer.

Further, the target substance detection chip 410, having the electric field enhancement layer 414 and the uneven structure imparting layer 413 stacked in this order on the light transmissive substrate 412, is configured such that, with the surface opposite to the surface on which the uneven structure is formed as a rear face, when the light is applied to the one surface of the electric field enhancement layer from the rear face side under the condition of total reflection, the enhanced electric field is generated in the vicinity of the front face. As explained above, when using a well-known waveguide mode excitation layer as the electric field enhancement layer 414, the uneven structure imparting layer 413 and the dielectric layer in the electric field enhancement layer 414 together form a waveguide layer, so the surface at which the light is totally reflected is the front face of the uneven structure imparting layer 413.

As described above, in the target substance detection chip 410 according to the second embodiment, the uneven structure can suppress adsorption of the conjugates.

Further, in the target substance detection chip 410 according to the second embodiment, the conjugates can be moved, with no regulation against application of the magnetic field to the front face. Therefore, the chip can be used in observing fluorescence of a target substance using the magnetic particles, and the target substance detection device using this chip can be manufactured compactly and inexpensively.

The target substance detection chip of the present embodiment is otherwise similar to the target substance detection chip 401, so the description will not be repeated.

Third Embodiment

A third embodiment of the third invention will be described with reference to the drawing. The third embodiment is an embodiment of the target substance detection chip of the third invention.

As shown in FIG. 29, a target substance detection chip 420 has a light transmissive substrate 422, an uneven structure imparting layer 423, and an electric field enhancement layer 424, and a liquid storage portion 425 is formed as an optional configuration in the light transmissive substrate 422. FIG. 29 illustrates a schematic configuration of the third embodiment.

The target substance detection chip 420 differs from the target substance detection chip 410 in that the uneven structure imparting layer 423 is formed on the light transmissive substrate 422 and the electric field enhancement layer 424 is formed on the uneven structure imparting layer 423.

Specifically, the target substance detection chip 420 includes: the light transmissive substrate 422 having a smooth surface; the uneven structure imparting layer 423 stacked on the smooth surface of the light transmissive substrate 422 and having a surface opposite to the surface on the light transmissive substrate 422 side constituting a first uneven surface; and the electric field enhancement layer 424 stacked on the first uneven surface of the uneven structure imparting layer 423 and having a surface opposite to the surface on the uneven structure imparting layer 423 side constituting a second uneven surface on which the uneven pattern of the first uneven surface has been transferred; wherein the second uneven surface forms the uneven structure.

The uneven structure imparting layer 423 is fixed onto the light transmissive substrate 422 in a manner not particularly limited, for example by adhesion, bonding, fusion, pasting, or the like.

The first uneven surface in the uneven structure imparting layer 423 is formed similarly as the uneven surface in the uneven structure imparting layer 403 (and 403').

When the electric field enhancement layer 424 is formed with a uniform thickness on the first uneven surface of the uneven structure imparting layer 423, the second uneven surface having the uneven pattern transferred from the first uneven surface can be formed in the electric field enhancement layer 424. This second uneven surface of the electric field enhancement layer 424 constituting the outermost layer forms an uneven structure on the front face.

In the target substance detection chip 420 configured as described above, the electric field enhancement layer 424 becomes the outermost layer. Therefore, as compared to the enhanced electric field in the case of the target substance detection chip 410 which is formed on the front face from the electric field enhancement layer 414 via the uneven structure imparting layer 413, the enhanced electric field can exist in a wider range on the front face, thereby facilitating the observation of the optical signals from the target substance and the like in the enhanced electric field.

Specifically, in each of the electric field enhancement layer 414 and the electric field enhancement layer 424, the enhanced electric field reaches up to 400 nm to 1,200 nm, and the electric field abruptly attenuates beyond that distance. Therefore, in the target substance detection chip 420 having the electric field enhancement layer 424 as the outermost layer and thus having the enhanced electric field existent in a wide range over the front face, the detection range of the target substance and the like by the enhanced electric field can be set wider than in the target substance detection chip 410.

The target substance detection chip of the present embodiment is otherwise similar to the target substance detection chip 410, so the description will not be repeated.

Fourth Embodiment

A fourth embodiment of the third invention will be described with reference to the drawing. The fourth embodiment is an embodiment of the target substance detection chip of the third invention.

Figure 30:
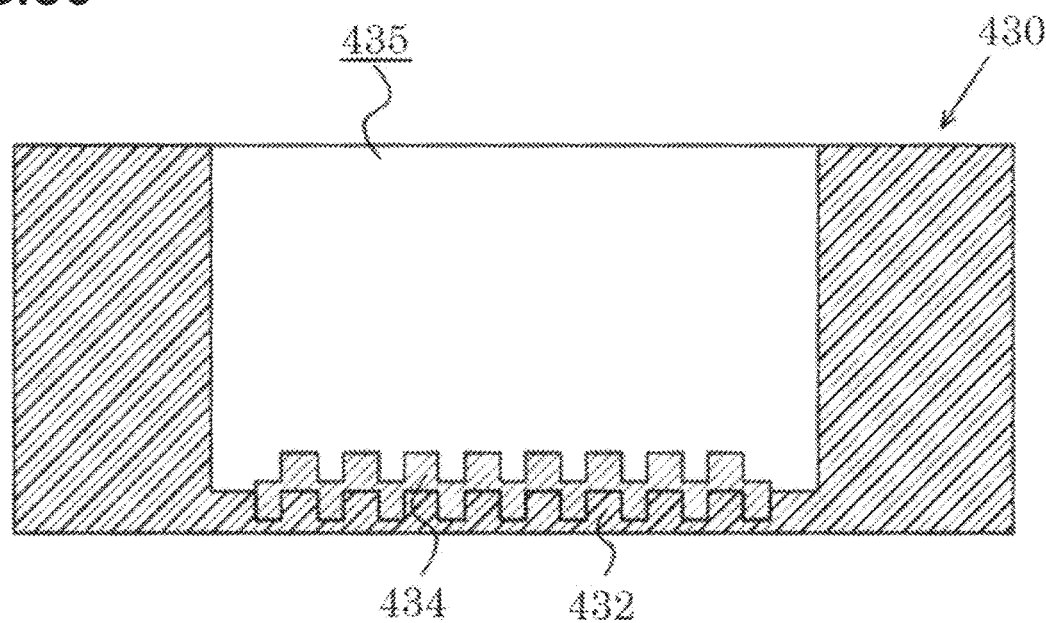
FIG. 30 illustrates a schematic configuration of a fourth embodiment.

As shown in FIG. 30, a target substance detection chip 430 has a light transmissive substrate 432 and an electric field enhancement layer 434, and a liquid storage portion 435 is formed in the light transmissive substrate 432. FIG. 30 illustrates a schematic configuration of the fourth embodiment.

The target substance detection chip 430 is similar to the target substance detection chip 420 in that the electric field enhancement layer 434 is an outermost layer, but it differs from the target substance detection chip 420 in that the electric field enhancement layer 434 is stacked on the light transmissive substrate 432.

Specifically, in the target substance detection chip 430, the light transmissive substrate 432 by itself has a first uneven surface formed thereon, which is similar to the uneven surface in the uneven structure imparting layer 403 (and 403'), and the electric field enhancement layer 434 is formed on this first uneven surface with a uniform thickness, to thereby form the second uneven surface having the uneven pattern transferred from the first uneven surface on the electric field enhancement layer 434. This second uneven surface of the electric field enhancement layer 434 constituting the outermost layer forms an uneven structure on the front face.

The light transmissive substrate 432 having the first uneven surface can be formed in a similar manner as the uneven structure imparting layer 403 (and 403').

In the target substance detection chip 430 configured as described above, the enhanced electric field can exist in a wide range on the front face, facilitating the observation of the optical signals from the target substance and the like in the enhanced electric field. In addition, with no uneven structure imparting layer disposed, the detection chip can be manufactured at a lower cost with the reduced number of components.

[Exemplary Formation of Uneven Structure]

For the uneven structures in the first through fourth embodiments, a further suitable formation will be described by way of example with reference to the drawings.

Figure 31A:
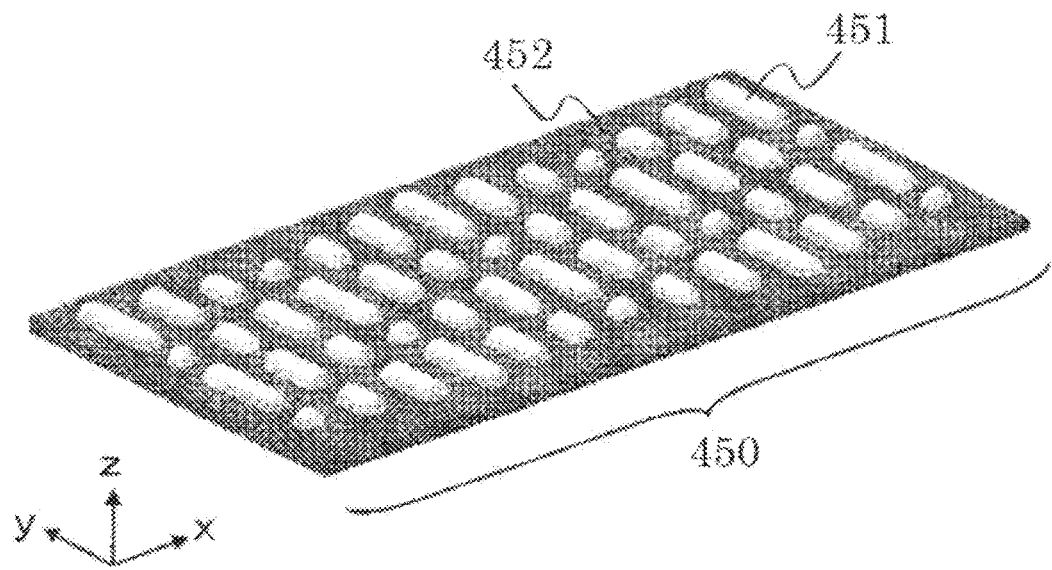
FIG. 31($a$) is a perspective view showing an exemplary formation of uneven structure.
Figure 31B:
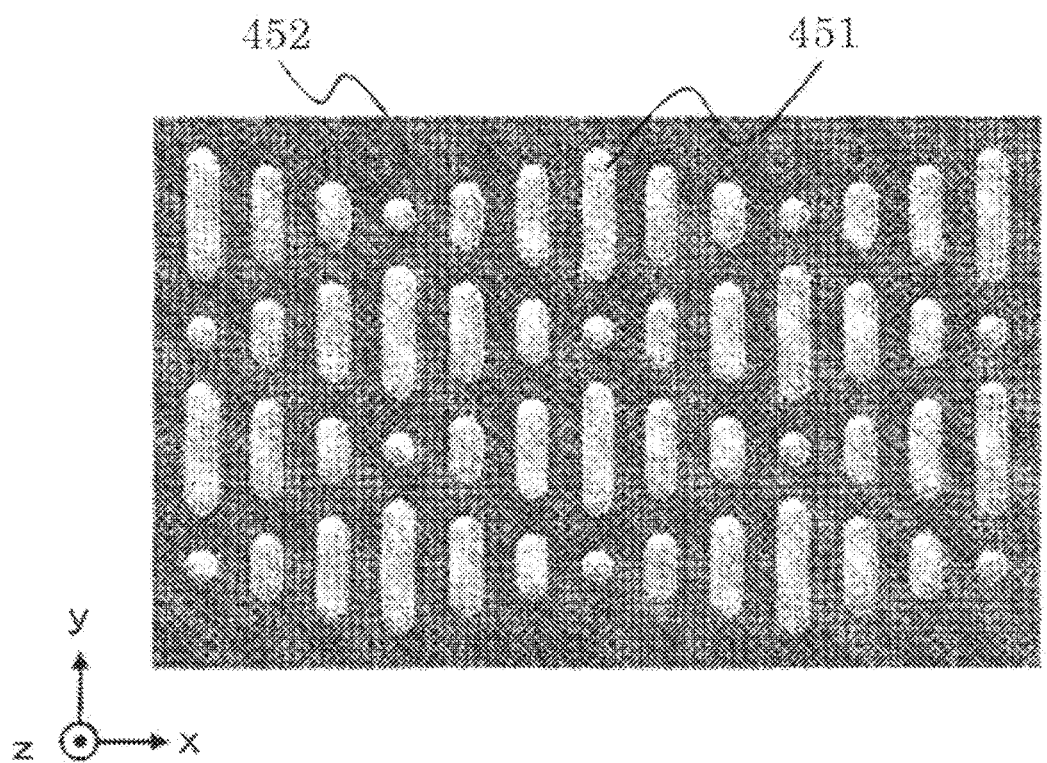

As shown in FIGS. 31(a) and 31(b), an exemplary uneven structure 450 has a plurality of projections 451 formed on a smooth portion 452. FIG. 31(a) is a perspective view and FIG. 31(b) is a top plan view of the exemplary formation of the uneven structure.

In the exemplary uneven structure 450, the projections 451 are formed in at least two shapes. That is, in the exemplary formation of the uneven structure, the projections 451 are formed in a plurality of shapes having different lengths in the longitudinal direction ("Y" direction in the figure).

Figure 32A:
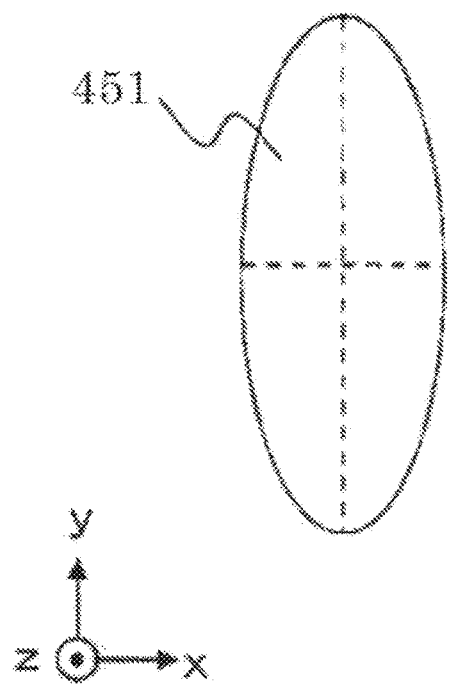
FIG. 32($a$) is an enlarged top plan view of one projection.
Figure 32B:
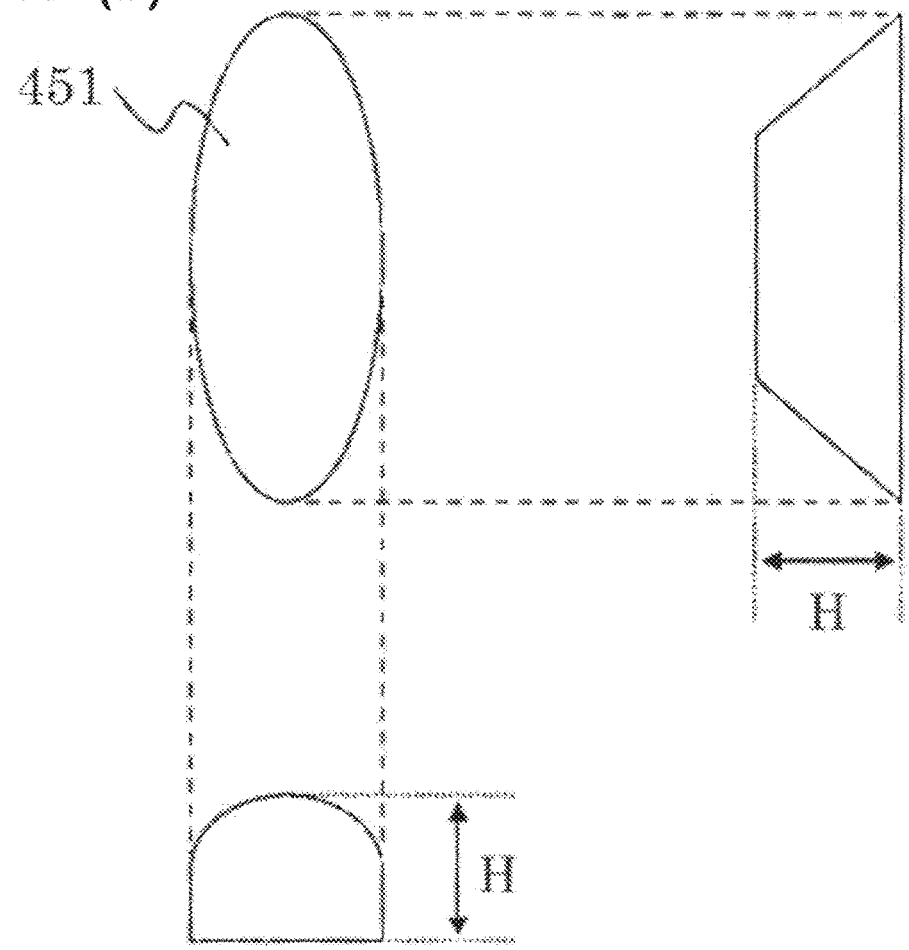

As shown by way of example in FIGS. 32(a) and 32(b) in enlarged view, the projections 451 each have a shape of two-fold rotational symmetry or linear symmetry. FIG. 32(a) is an enlarged top plan view of one projection, and FIG. 32(b) is the top plan view as well as side views in the longitudinal and lateral directions.

The projections 451 have a unit periodic structure of a rhombic shape as seen from above, in which a longitudinally longest projection is placed at the center to form an axis of symmetry, and three projections are arranged on each side of the symmetry axis such that the projections adjacent to each other in the lateral direction ("X" direction in the figure) have their longitudinal lengths gradually decreased with increasing distance from the projection placed at the center.

The projections 451 are arranged such that a longitudinally shortest projection, located at a longitudinal end of one unit periodic structure, is shared with another unit periodic structure that is adjacent in the lateral direction. Further, a longitudinally longest projection in the one unit periodic structure is arranged to face a longitudinally shortest projection in another unit periodic structure that is adjacent in the longitudinal direction. The projections thus have a periodic structure as a whole with the plurality of unit periodic structures arranged periodically.

In the exemplary uneven structure 450 configured as described above, the individual unit periodic structures resemble a fish scale existent in nature, and form a scaly surface as a whole. This suppresses adsorption of foreign matters including the conjugates to the front face having the projections 451 formed thereon.

While the unit periodic structure has a shape of rhombus in this example, it may have a shape of isosceles triangle or parallelogram.

Further, in the case of using the exemplary uneven structure 450 to form the uneven structure in the target substance detection chip, the uneven pattern of the exemplary uneven structure 450 may be applied to the above-described uneven surface or to the above-described first uneven surface as the underlayer of the second uneven surface.

It should be noted that the lateral length in the exemplary uneven structure 450 corresponds to the "width W" described in conjunction with FIGS. 27(*a*) and 27(*b*).

Further, the exemplary uneven structure 450 can be formed by applying the matters described in Japanese Patent Application Laid-Open No. 2015-160342.

(Target Substance Detection Device)

A target substance detection device in the third invention includes the target substance detection chip of the third invention, a light irradiation unit, and a magnetic field application unit, and also has a light detection unit as needed.

The target substance detection device detects the target substance using the magnetic particle that is bound to the target substance. In the case where the target substance is less liable to generate fluorescence or scattered light by the evanescent field or the enhanced electric field, a labeling material is used to label the target substance.

The labeling substance is not particularly limited, and a fluorescent labeling substance or a light scattering substance that is specifically adsorbed to or bound to the target substance to label the target substance may be used.

For the fluorescent labeling substance, any of well-known fluorescent substances such as fluorescent dye, quantum dot, fluorescent dyeing agent and the like can be used.

For the light scattering substance, any of well-known light scattering substances such as nanoparticles, for example polystyrene beads or gold nanoparticles, can be used.

The method for binding the target substance and the labeling substance together is not particularly limited, and any of well-known methods such as physical adsorption, antigen-antibody reaction, DNA hybridization, biotin-avidin bond, chelate bond, amino bond, etc. can be used.

<Light Irradiation Unit>

The light irradiation unit is operable, with a surface of the target substance detection chip opposite to the surface on which the uneven structure is formed as a rear face, to apply light from the rear face side under the condition of total reflection.

The light source of the light irradiation unit is not particularly limited, and can be selected as appropriate according to the purpose. Examples of the light source include a well-known lamp, LED, and laser. In the third invention, light is applied from the rear face side of the target substance detection chip under the condition of total reflection to form an evanescent field or an enhanced electric field on the front face, to thereby cause a conjugate comprising the target substance and the magnetic particle to emit an optical signal with the evanescent field or the enhanced electric field as excitation light. The role required for the light irradiation unit to play to this end is simply to apply light from the rear face side of the target substance detection chip under the condition of total reflection, and any light source can be selected as long as the unit can play such a role.

In the case of using a radiation light source such as a lamp or LED, any rays among the emitted light that are irradiated in the directions toward the rear face side of the target substance detection chip need to satisfy the condition of total reflection in order to avoid leakage of the irradiated light from the front face side of the target substance detection chip. To this end, when a radiation light source is used, a guide unit such as a collimator lens that restricts the irradiated directions of the light to a specific direction may be used.

Further, in the case of using fluorescence as an optical signal, a light source of monochromatic light having a wavelength that can excite fluorescence is used preferably. Alternatively, light from a light source having a wide wavelength range, such as a lamp, LED, or the like, may be passed through an optical filter such as a band-pass filter to obtain monochromatic light having only the wavelength that can excite fluorescence, and the resultant light may be applied from the rear face side of the target substance detection chip.

Here, in the case where the target substance detection chip is of a plate shape having the front face and the rear face parallel to each other, light applied from the rear face side will not be totally reflected if there is a liquid on the front face. In such a case, the target substance detection chip may be configured as follows. A diffraction grating may be formed in a portion of the rear face of the target substance detection chip. This allows light applied to the diffraction grating at a specific angle to be diffracted by the diffraction grating and introduced into the target substance detection chip. The light thus introduced into the target substance detection chip can be directed to the front face under the condition of total reflection, so that the evanescent field or the enhanced electric field is formed on the front face. Alternatively, the target substance detection chip may be formed such that the front face and the rear face are not parallel to each other. Still alternatively, it may be configured such that light applied from the light source is directed to the rear face of the target substance detection chip via a well-known prism. Such a prism can be optically attached to the rear face of the target substance detection chip by using refractive index matching oil, an optical adhesive, or the like. When the material for forming the prism is chosen to be the same material as the light transmissive substrate, the light transmissive substrate and the prism may be formed by integral molding.

<Magnetic Field Application Unit>

The magnetic field application unit is formed by at least one of a first magnetic field application unit and a second magnetic field application unit.

<First Magnetic Field Application Unit>

The first magnetic field application unit is operable to apply a first magnetic field that moves the magnetic particles included in the sample liquid introduced onto the front face of the target substance detection chip in a direction parallel to or away from the front face. The unit can apply a move-away magnetic field that moves the magnetic particles away from the front face of the target substance detection chip, or a parallel-move magnetic field that makes a magnetic force act in a direction moving the magnetic particles parallel to the front face above the front face of the target substance detection chip.

The target substance and labeling substance constituting the conjugate together with the magnetic particle emit an optical signal only in the evanescent field or the enhanced electric field. The evanescent field and the enhanced electric field have their intensity attenuated with increasing distance from the front face of the target substance detection chip. Accordingly, the optical signal will attenuate as the conjugate is moved away from the front face with application of the move-away magnetic field, and further, the optical signal from the conjugate will disappear as the conjugate is moved away from the front face beyond the distance where the intensity of the evanescent field or the enhanced electric field is considered to be zero. Still further, in the case where two-dimensional image information can be obtained using an imaging device as the light detection unit, the optical signal emitted from the conjugate that has moved above the front face by the first magnetic field applied can be measured over time as the movement of the optical signal. The target substance detection device detects such attenuation (including disappearance) or movement (that may accompany attenuation or disappearance) of the optical signals to thereby detect the target substance.

The first magnetic field application unit is not particularly limited as long as it can apply a magnetic field to move the conjugate, and can be selected as appropriate according to the purpose. At least one of well-known electromagnet and permanent magnet can be used.

<Second Magnetic Field Application Unit>

The second magnetic field application unit is disposed on the side of the rear face of the target substance detection chip and is operable to apply a second magnetic field to draw the magnetic particles within the sample liquid introduced onto the front face toward the front face.

The second magnetic field application unit is not particularly limited, and can be selected as appropriate according to the purpose. For example, a well-known electromagnet and permanent magnet can be used.

With such a second magnetic field application unit, the conjugate floating in the sample liquid can be drawn toward the front face of the target substance detection chip, enabling detection of the target substance in a short time.

Further, the second magnetic field application unit is preferably capable of moving the magnetic particles in a direction having a vector component parallel to the in-plane direction of the front surface in the state of applying the second magnetic field.

Such a second magnetic field application unit can be configured for example as follows. With the electromagnet or the permanent magnet held on a sliding member, movement control is performed between an initial state where the electromagnet or the permanent magnet is positioned in the vicinity of the area (detection area) on the rear face side of the target substance detection chip where the light is applied from the light irradiation unit, and a state where the electromagnet or the permanent magnet is moved in the direction having a vector component parallel to the in-plane direction of the front face of the target substance detection chip. When the electromagnet is used, it is energized continuously or intermittently during the movement control. The intensity of energization may be changed during the movement control.

Alternatively, a plurality of such electromagnets or permanent magnets may be disposed, and control may be performed on the magnetic field application states in the respective members. This configuration produces the similar effects as those produced by the above-described configuration of holding the electromagnet or the permanent magnet on the sliding member and performing the movement control.

The configuration of the second magnetic field application unit is not particularly limited, and the unit may have a through hole formed therein, or it may have an incomplete annular shape such as a U shape. Alternatively, the unit may have a plurality of members arranged in an annular or incomplete annular shape.

The second magnetic field application unit that is capable of moving the magnetic particles in the direction having a vector component parallel to the in-plane direction of the front face in the state of applying the second magnetic field can eliminate noise signals.

Specifically, while the target substance with the magnetic particle bound thereto will move with the movement of the second magnetic field application unit, noise caused by scratches on the surface of the target substance detection chip or the like will not move following the movement of the second magnetic field application unit. Thus, the detection focusing on the moving optical signals can eliminate the noise signals.

<Light Detection Unit>

The light detection unit is disposed on the side of the front face of the target substance detection chip and is capable of detecting an optical signal emitted from the conjugate.

The light detection unit is not particularly limited, and can be selected as appropriate according to the purpose. Examples include photodetectors such as a well-known photodiode, photomultiplier, and the like.

When information on optical signals can be obtained as two-dimensional image information, observations can be performed chronologically on positional information of the optical signals in the two-dimensional image information appearing as light spots, size information observed in two dimensions, or information on an increase or decrease in intensity of the optical signals at the light spots. This enables determination as to whether a certain light spot results from a target substance, whether it indicates information concerning a target substance, or whether it indicates information not related to a target substance, such as a contaminant, fluctuation in the output from the light source, a scratch on the surface of the detection plate, or the like. To enable acquisition of such two-dimensional image information, an imaging device may be selected as the light detection unit. The imaging device is not particularly limited, and can be selected as appropriate according to the purpose. Examples of the imaging device include image sensors such as a well-known CCD image sensor, CMOS image sensor, and the like.

(Target Substance Detection Method)

The target substance detection method in the third invention includes at least a light irradiation step and a conjugate moving step.

<Light Irradiation Step>

The light irradiation step is a step of, with a surface of the target substance detection chip of the third invention opposite to the surface on which the uneven structure is formed as a rear face, applying light from the rear face side under the condition of total reflection.

The light irradiation step can be performed by the light irradiation unit in the target substance detection device of the third invention.

<Conjugate Moving Step>

The conjugate moving step is performed as either one of: a first conjugate moving step of moving a conjugate of a target substance and a magnetic particle included in a sample liquid introduced on the front face of the target substance detection chip in a direction parallel to or away from the front face by application of a first magnetic field; and a second conjugate moving step of drawing the conjugate in the sample liquid toward the front face by application of a second magnetic field from a magnetic field application unit disposed on the side of the rear face.

Preferably, the second conjugate moving step is further a step of moving the magnetic field application unit, in the state of applying the second magnetic field, in the direction having a vector component parallel to the in-plane direction of the front face, to move the conjugate following the movement of the magnetic field application unit.

The conjugate moving step can be performed by the magnetic field application unit in the target substance detection device of the third invention.

Fifth Embodiment

A fifth embodiment of the third invention will now be described with reference to the drawings. The fifth embodiment is an embodiment of the target substance detection device of the third invention.

Figure 33:
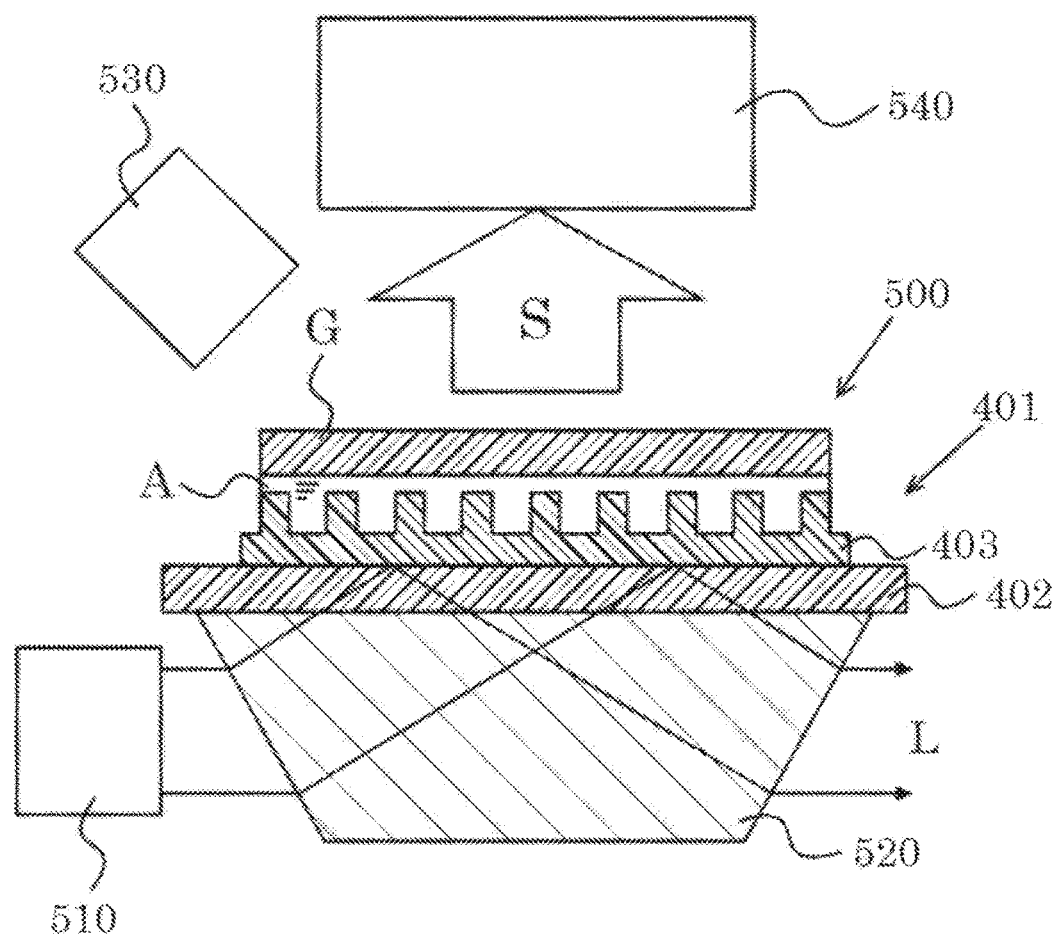
FIG. 33 illustrates a schematic configuration of a fifth embodiment.

As shown in FIG. 33, a target substance detection device 500 has an optical system configured in accordance with a well-known total reflection fluorescence microscope, and includes a target substance detection chip 401, a light irradiation unit made up of a light source 510 and an optical prism 520, a first magnetic field application unit 530, and a light detection unit 540 (imaging device). The imaging device is configured with a well-known CCD image sensor or the like, for example, and is capable of acquiring two-dimensional images. FIG. 33 illustrates a schematic configuration of the fifth embodiment.

The target substance detection chip 401 receives light L from the rear face side, and enables the evanescent field to be existent on the front face (on the side where an uneven structure imparting layer 403 is formed). The target substance detection chip 401 holds a sample liquid A introduced onto the front face with a cover glass G.

The light irradiation unit is configured such that light L emitted from the light source 510 enters a light transmissive substrate 402 via the optical prism 520, and is transmitted through the light transmissive substrate 402 and applied under the condition of being totally reflected at the front face of the uneven structure imparting layer 403.

The first magnetic field application unit 530 is disposed diagonally above a detection area on the front face of the target substance detection chip 401 (where the light L is received from the light irradiation unit and the evanescent field is formed on the front face). The first magnetic field application unit 530 is configured to apply a magnetic field to draw conjugates in a sample liquid A introduced on the front face toward the first magnetic field application unit 530 and move the conjugates in the direction away from the front face of the target substance detection chip 401. The first magnetic field application unit 530 in this example is made up of an electromagnet.

In the target substance detection device 500 configured as described above, firstly, the sample liquid A is introduced on the front face of the target substance detection chip 401.

Next, after the conjugates floating in the solution of the sample liquid A have settled out on the front face of the target substance detection chip 401 by gravitational sedimentation, light L is applied from the light source 510 via the optical prism 520 under the condition of being totally reflected at the front face of the uneven structure imparting layer 403. The light detection unit 540 obtains optical signals S based on the evanescent field formed on the front face of the target substance detection chip 401.

Subsequently, the electromagnet as the first magnetic field application unit 530 is energized to apply a magnetic field to draw the conjugates within the sample liquid A toward the first magnetic field application unit 530 and move the conjugates in the direction away from the front face of the target substance detection chip 401.

Here, in the target substance detection device 500, the uneven structure formed on the front face of the target substance detection chip 401 suppresses adsorption of the conjugates to the front face of the target substance detection chip 401, facilitating the movement of the conjugates before and after the application of the magnetic field.

Subsequently, the light detection unit 540 obtains optical signals on the front face of the target substance detection chip 401 after the movement of the conjugates, while maintaining the observation field of view.

Figure 34A:
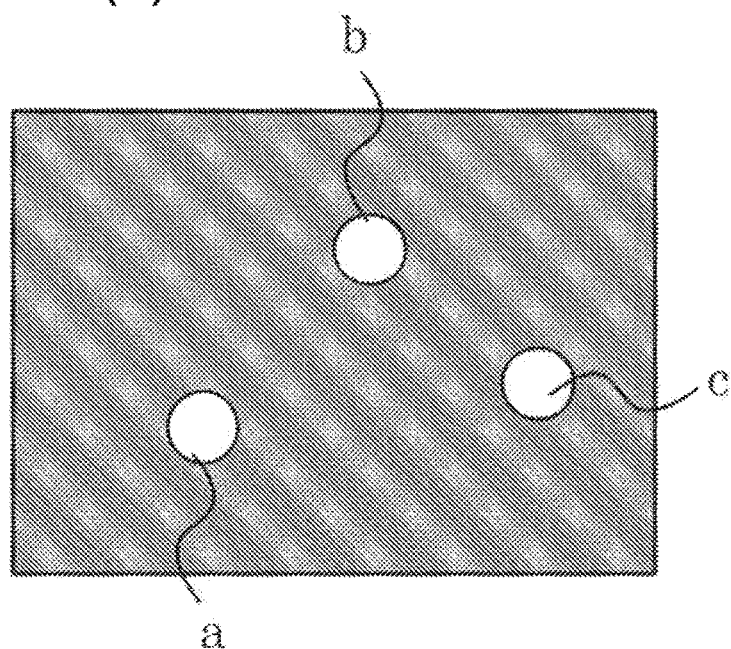
FIG. 34($a$) shows the state on the front face before application of a magnetic field.
Figure 34B:
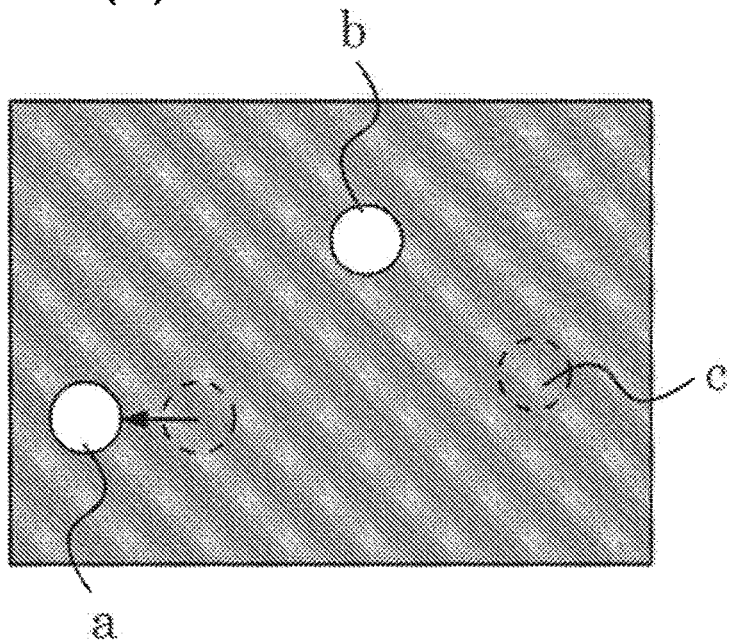

In the target substance detection device 500 configured as described above, optical signals before and after the application of the magnetic field (before and after the movement of the conjugates) are obtained as shown in FIGS. 34(a) and 34(b). The optical signals a, c based on the target substance are detected clearly distinguishably from the noise signal b due to a scratch on the front face of the target substance detection chip 401, a contaminant adsorbed to or present on the front face, a fluctuation of the output from the light source, or the like. FIG. 34(a) shows the state on the front face before application of the magnetic field, and FIG. 34(b) shows the state on the front face after the application of the magnetic field. Although not shown in the figure, appearance of an optical signal based on the movement from outside the observation field of view can be detected as well.

As described above, according to the target substance detection device 500, the uneven structure on the target substance detection chip 401 facilitates movement of the conjugate, and enables accurate detection of the target substance constituting the conjugate. Even in the case where the contaminants are adsorbed to the front face of the target substance detection chip 401, the detection can be performed by ignoring the presence of such contaminants. The washing treatment of the front face is not necessarily required every time the detection is made, ensuring efficient detection.

Sixth Embodiment

A sixth embodiment of the third invention will now be described with reference to the drawings. The sixth embodiment is an embodiment of the target substance detection device of the third invention.

Figure 35:
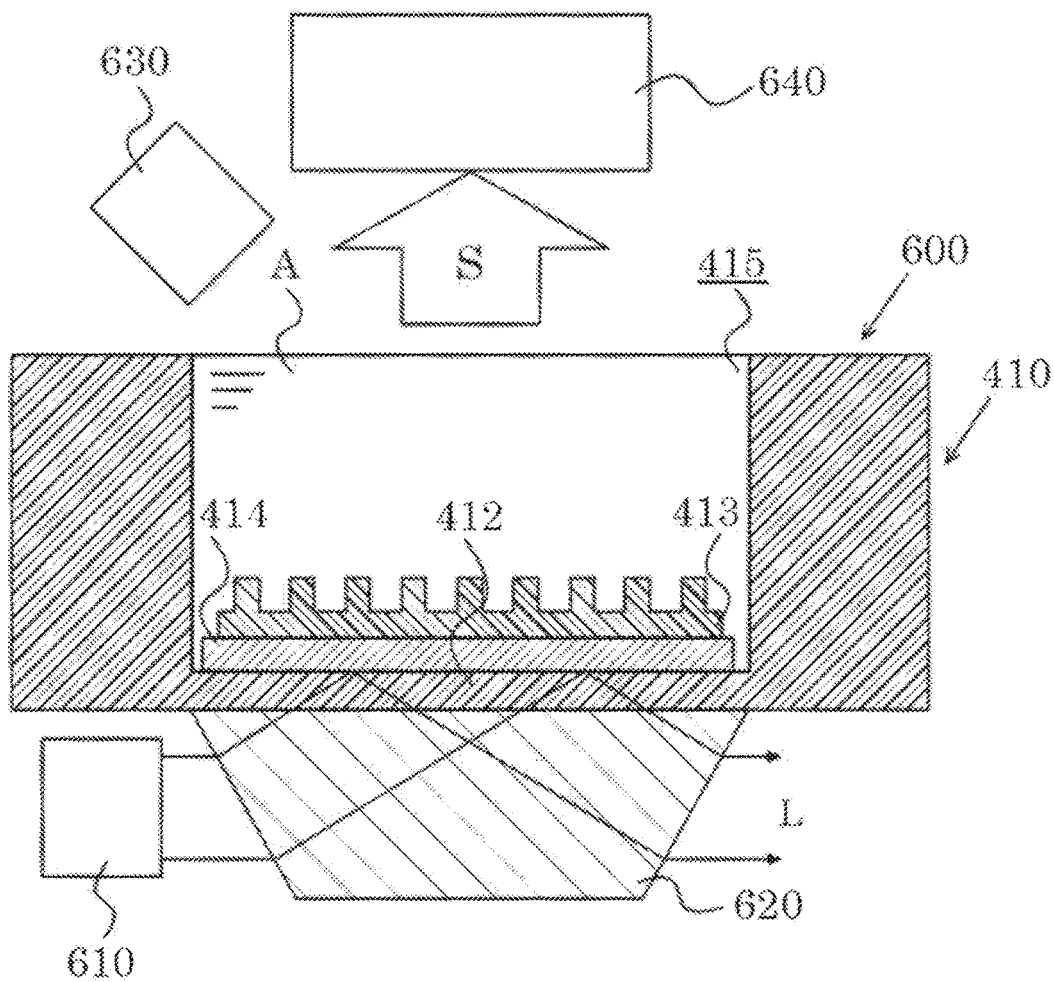
FIG. 35 illustrates a schematic configuration of a sixth embodiment.

As shown in FIG. 35, a target substance detection device 600 has an optical system configured in accordance with a well-known surface plasmon resonance sensor and waveguide mode sensor, and includes a target substance detection chip 410, a light irradiation unit made up of a light source 610 and an optical prism 620, a first magnetic field application unit 630, and a light detection unit 640 (the imaging device). FIG. 35 illustrates a schematic configuration of the sixth embodiment.

The target substance detection chip 410 receives light L from the rear face side, and enables the enhanced electric field to be existent on the front face (on the side where an uneven structure imparting layer 413 is formed). The target substance detection chip 410 has a liquid storage portion 415 in which a sample liquid A is introduced.

The light irradiation unit is capable of directing light L emitted from the light source 610, via the optical prism 620 and a light transmissive substrate 412, to an electric field enhancement layer 414 under the condition of total reflection.

The first magnetic field application unit 630 is disposed diagonally above a detection area on the front face of the target substance detection chip 410 (where the light L is received from the light irradiation unit and the enhanced electric field is formed on the front face). The first magnetic field application unit 630 is configured to apply a magnetic field to draw conjugates in the sample liquid A introduced in the liquid storage portion 415 toward the first magnetic field application unit 630 and move the conjugates in the direction away from the front face of the target substance detection chip 410. The first magnetic field application unit 630 in this example is made up of an electromagnet.

In the target substance detection device 600 configured as described above, firstly, the sample liquid A is introduced into the liquid storage portion 415.

Next, after the conjugates floating in the solution of the sample liquid A have settled out on the front face of the target substance detection chip 410 by gravitational sedimentation, light L emitted from the light source 610 is directed via the optical prism 620 and the light transmissive substrate 412 to one surface of the electric field enhancement layer 414 under the condition of total reflection, and the light detection unit 640 obtains optical signals S based on the enhanced electric field formed on the front face of the target substance detection chip 410.

Subsequently, the electromagnet as the first magnetic field application unit 630 is energized to apply a magnetic field to draw the conjugates within the sample liquid A in the liquid storage portion 415 toward the first magnetic field application unit and move the conjugates in the direction away from the front face of the target substance detection chip 410.

Here, in the target substance detection device 600, the uneven structure formed on the front face of the target substance detection chip 410 suppresses adsorption of the conjugates to the front face of the target substance detection chip 410, facilitating the movement of the conjugates before and after the application of the magnetic field.

Subsequently, the light detection unit 640 obtains the optical signals on the front face of the target substance detection chip 410 after the movement of the conjugates, while maintaining the observation field of view.

Figure 36A:
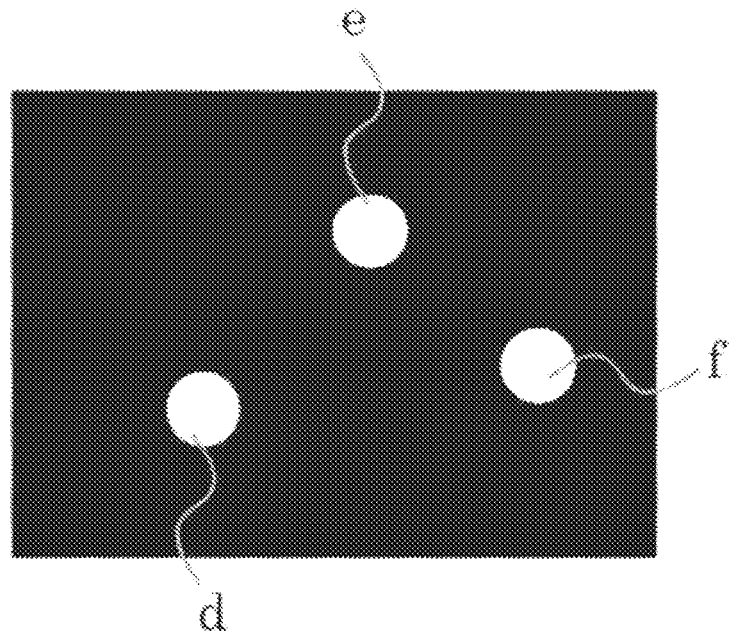
FIG. 36($a$) shows the state on the front face before application of a magnetic field.
Figure 36B:
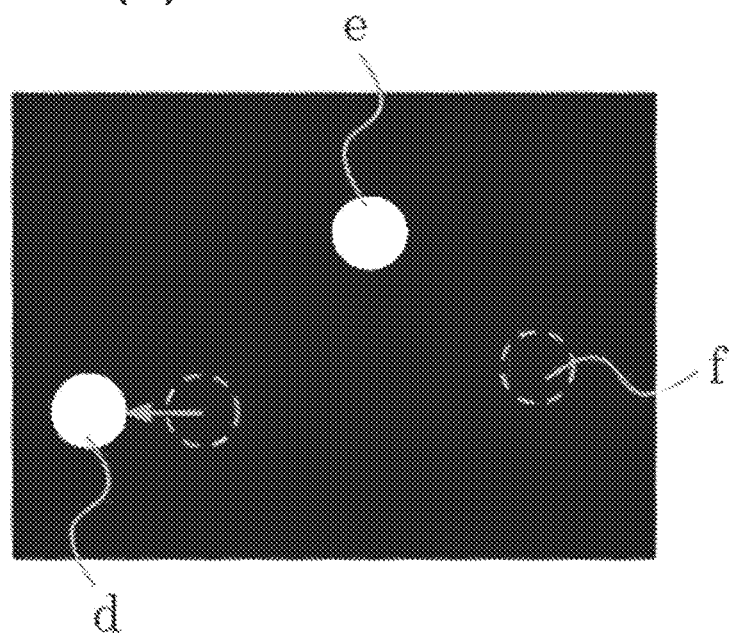

In the target substance detection device 600 configured as described above, optical signals before and after the application of the magnetic field (before and after the movement of the conjugates) are obtained as shown in FIGS. 36(a) and 36(b). The optical signals d, f based on the target substance are detected clearly distinguishably from the noise signal e due to a scratch on the front face of the target substance detection chip 410, a contaminant adsorbed to or present on the front face, a fluctuation of the output from the light source, or the like. FIG. 36(a) shows the state on the front face before application of the magnetic field, and FIG. 36(b) shows the state on the front face after the application of the magnetic field.

As shown in FIGS. 36(a) and 36(b), the optical signals have a dark-field background due to the attenuation of the enhanced electric field. The target substance detection device 600 detects the target substance on the basis of the optical signals of light spots. Although not shown in the figure, appearance of an optical signal based on the movement from outside the observation field of view can be detected as well.

According to the target substance detection device 600, the uneven structure on the target substance detection chip 410 facilitates movement of the conjugate, and enables accurate detection of the target substance constituting the conjugate. Even in the case where the contaminants are adsorbed to the front face of the target substance detection chip 410, the detection can be performed by ignoring the presence of such contaminants. The washing treatment of the liquid storage portion 415 is not necessarily required every time the detection is made, ensuring efficient detection.

Seventh Embodiment

A seventh embodiment of the third invention will now be described with reference to the drawings. The seventh embodiment is an embodiment of the target substance detection device of the third invention.

Figure 37:
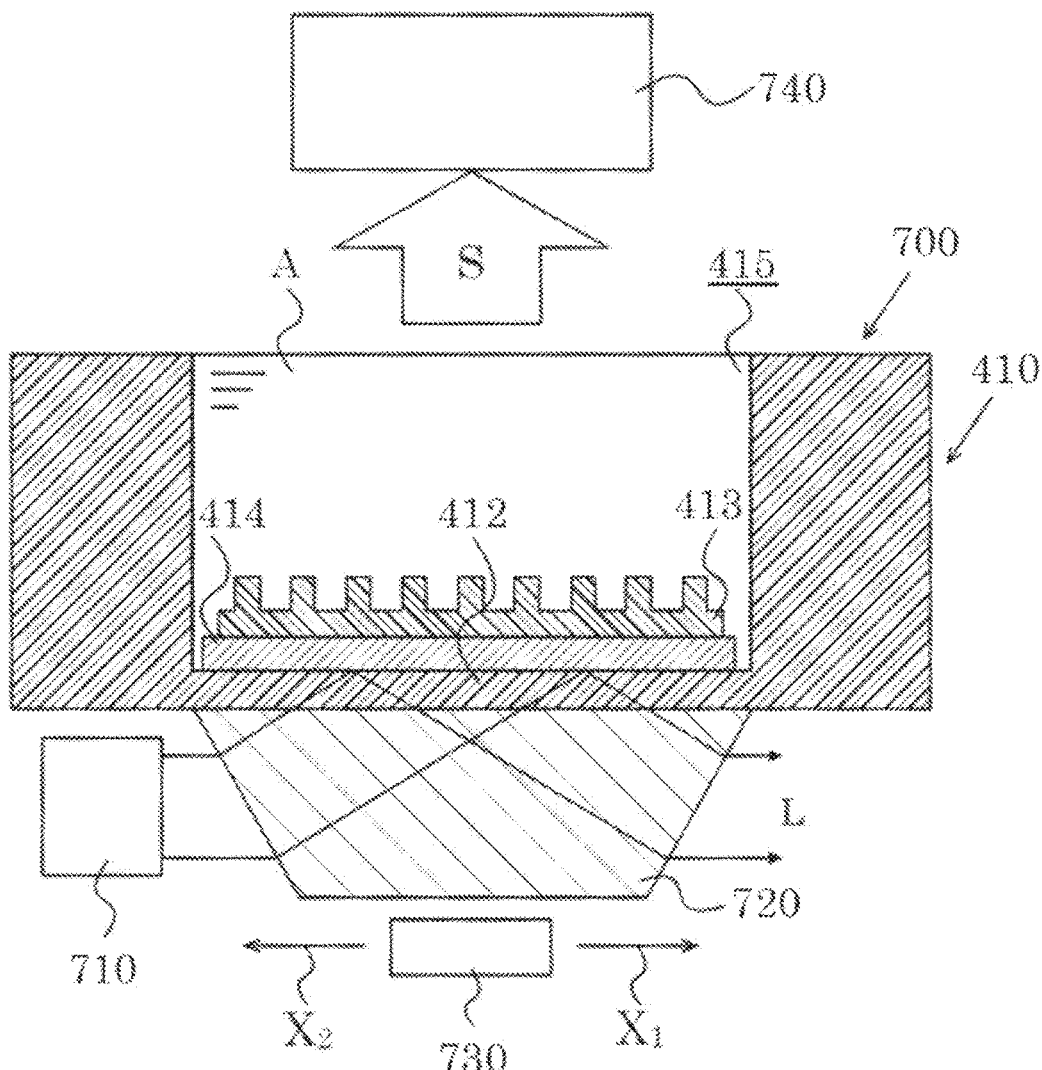
FIG. 37 illustrates a schematic configuration of a seventh embodiment.

As shown in FIG. 37, a target substance detection device 700 according to the seventh embodiment has an optical system configured in accordance with a well-known surface plasmon resonance sensor and waveguide mode sensor, and includes a target substance detection chip 410, a light irradiation unit made up of a light source 710 and an optical prism 720, a second magnetic field application unit 730, and a light detection unit 740 (the imaging device). FIG. 37 illustrates a schematic configuration of the seventh embodiment.

The light irradiation unit and the light detection unit 740 can be configured similarly as the light irradiation unit and the light detection unit 640 in the target substance detection device 600 according to the sixth embodiment. The target substance detection device 700 according to the seventh embodiment differs from the target substance detection device 600 according to the sixth embodiment in that the second magnetic field application unit 730 is provided instead of the first magnetic field application unit 630. The differences will be described below.

The second magnetic field application unit 730 is disposed on the side of the rear face of the target substance detection chip 410, and is operable to apply a magnetic field to draw the conjugates in the sample liquid A introduced in the liquid storage portion 415 toward the front face of the target substance detection chip 410. The unit is also movable in a direction having a vector component parallel to the in-plane direction of the front face of the target substance detection chip 410 while applying the magnetic field. Here, the second magnetic field application unit 730 is configured with a permanent magnet and a sliding member (not shown) that slides the permanent magnet in an $X_1$ or $X_2$ direction.

For moving the conjugates, the magnetic field is firstly applied from the second magnetic field application unit 730 to draw the conjugates in the sample liquid A in the target substance detection chip 410 toward the front face of the target substance detection chip 410. Then, the second magnetic field application unit 730, in the state of applying the magnetic field, is moved in the direction ($X_1$ or $X_2$ direction) having a vector component parallel to the in-plane direction of the front face of the target substance detection chip 410, to thereby move the conjugates following the movement of the second magnetic field application unit 730.

In the case of using this second magnetic field application unit 730, the conjugates in the sample liquid A are drawn toward the front face of the target substance detection chip 410 by the magnetic field applied. This eliminates the need to wait for the conjugates floating in the solution of the sample liquid A to settle out on the front face of the target substance detection chip 410 by gravitational sedimentation.

Figure 38A:
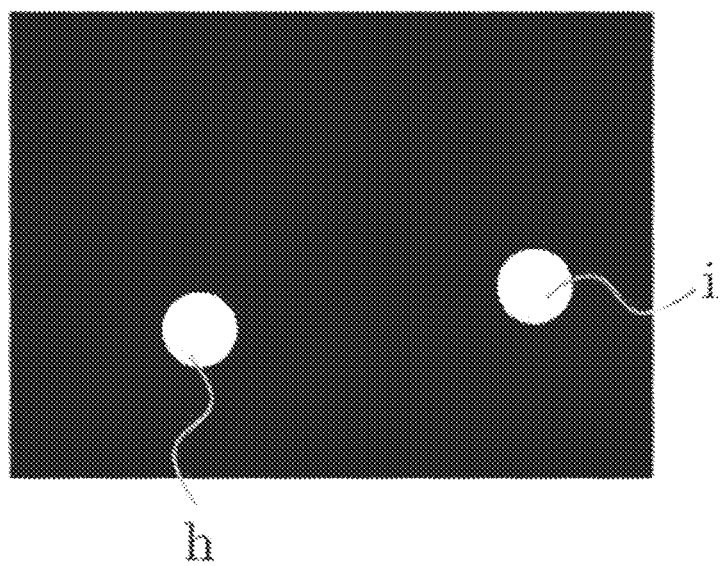
FIG. 38($a$) shows the state on the front face before movement of a second magnetic field application unit.
Figure 38B:
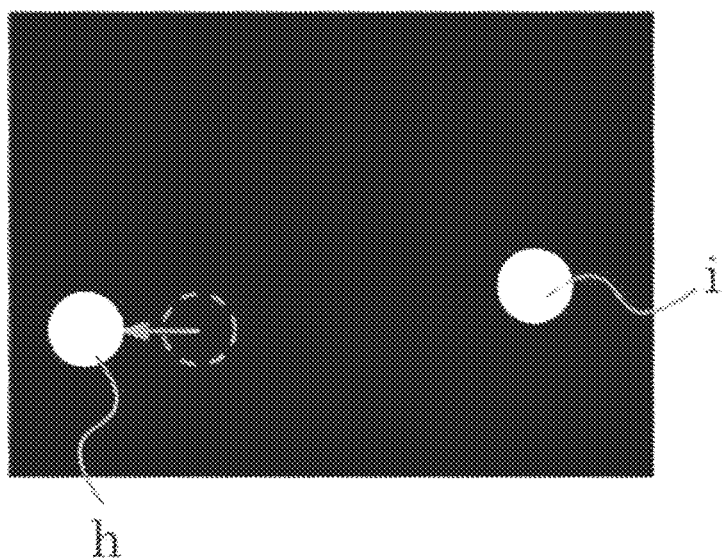

Further, in the target substance detection device 700 configured as described above, optical signals before and after the movement of the second magnetic field application unit are obtained as shown in FIGS. 38(*a*) and 38(*b*). The optical signal h based on the target substance can be detected clearly distinguishably from the noise signal i due to a scratch on the front face of the target substance detection chip 410, a contaminant adsorbed to or present on the front face, a fluctuation of the output from the light source, or the like. FIG. 38(*a*) shows the state on the front face before the movement of the second magnetic field application unit, and FIG. 38(*b*) shows the state on the front face after the movement of the second magnetic field application unit.

A fourth invention will be described below. The fourth invention relates to modified examples of the first through third inventions.

A target substance detection chip according to the fourth invention includes: an entirely approximately plate-shaped light transmissive member having a support surface arranged on a surface constituting a top surface relative to a bottom surface, an inclined surface which is one of an upwardly inclined surface inclined away from the support surface from the top surface toward the bottom surface side with respect to a thickness direction and a downwardly inclined surface inclined away from the support surface from the bottom surface toward the top surface side with respect to the thickness direction, and a main body portion capable of receiving light and guiding the light through an interior thereof; and an uneven structure constituted by a plurality of projections arranged periodically on the support surface; wherein the light transmissive member has a light directing structure which is one of a first light directing structure in which the light applied from the side of the top surface and passed through the upwardly inclined surface is directed via the main body portion to the support surface under a condition of total reflection and a second light directing structure in which the light applied from the top surface side and reflected at the downwardly inclined surface is directed via the main body portion to the support surface under the condition of total reflection, the light transmissive member has a sensing surface on a portion thereof, and the sensing surface partially or entirely has the uneven structure.

The target substance detection chip is not particularly limited, and it may be one in which the support surface has disposed thereon an electric field enhancement layer in which, in response to the support surface irradiated with light under the condition of total reflection, an enhanced electric field is formed on a surface opposite to the surface on the support surface side, or it may be one in which the support surface has a region thereon in which, in response to the support surface irradiated with light under the condition of total reflection, an evanescent field is generated on a surface opposite to the surface on the support surface side.

A target substance detection device according to the fourth invention includes: the target substance detection chip of the fourth invention; a light irradiation unit disposed on the side of the top surface of the light transmissive member and operable to irradiate the support surface with the light under the condition of total reflection via the light directing structure; and a magnetic field application unit disposed on the side of the bottom surface of the light transmissive member.

Here, the light transmissive member and the light directing structure in the fourth invention can be configured similarly as described in relation to the light transmissive member and the light directing structure in the first and second inventions.

Further, the uneven structure in the fourth invention can be configured similarly as described in relation to the uneven structure in the third invention.

The electric field enhancement layer in the fourth invention can be configured similarly as described in relation to the electric field enhancement layer in the second and third inventions.

The light irradiation unit and the magnetic field application unit in the fourth invention can be configured similarly as described in relation to the light irradiation unit and the magnetic field application unit in the first and second inventions.

Further, the fourth invention can be configured by appropriately adopting the matters described in relation to the first through third inventions, including the light detection unit.

The fourth invention is configured in accordance with the matters described in the seventh embodiment in the first invention (see FIG. 12) and the matters described in relation to the uneven structure in the third invention, by applying the sensing surface 62*a* of the detection chip 60 shown in FIG. 12 as the support surface, and forming the uneven structure in the third invention on this support surface. The uneven structure may or may not have the electric field enhancement layer, as in the examples illustrated in FIGS. 26, and 28 to 30. The electric field enhancement layer, when applied, is disposed on the support surface in such a manner that, in response to the support surface irradiated with light under the condition of total reflection, an enhanced electric field is formed on a surface opposite to the surface on the support surface side.

Figure 39:
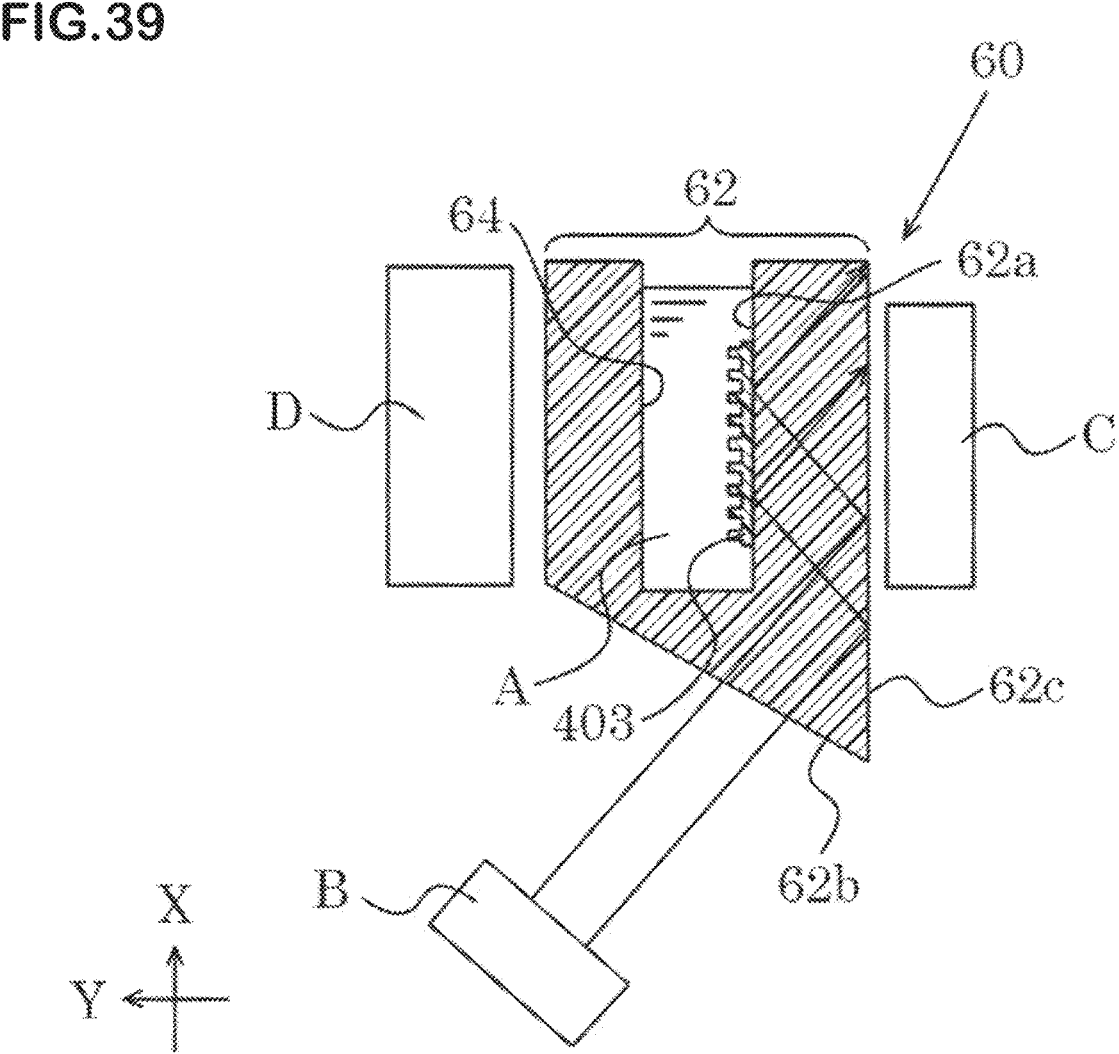
FIG. 39 illustrates an embodiment of a fourth invention.

Specifically, as shown in FIG. 39, an uneven structure 403 (see FIG. 26 etc.) is formed on a sensing surface 62*a* (see FIG. 12). FIG. 39 illustrates an embodiment of the fourth invention. In FIG. 39, the reference numeral 403 (uneven structure) is the one used for the third invention, and the remaining reference numerals are those used for the first invention.

In this embodiment, the light transmissive member 62 has a sample liquid storage groove 64 formed as a drilled groove having an approximately rectangular shape in cross section, which is drilled in a direction parallel to the in-plane direction of the bottom surface (in the figure, the surface on the right side of the detection chip 60) from the side surface toward the inclined surface 62*b* side. Of the opposing surfaces of the sample liquid storage groove 64, the surface on the side closer to the bottom surface (in the figure, the sensing surface 62*a*) constitutes the support surface.

REFERENCE SIGNS LIST

Reference Numerals Used in the Description of the First Invention

1, 1', 10, 20, 30, 40, 40', 50, 60: detection chip
2, 2', 12, 22, 32, 42, 42', 52, 62: light transmissive member 2a, 2a', 12a, 22a, 32a, 42a, 42a', 52a, 62a: sensing surface
2b, 2b', 12b, 42b, 42b', 62b: upwardly inclined surface
2c, 12c, 22c, 32c, 42c, 42c', 52c, 62c: main body portion
4, 24: sidewall portion
14, 34, 44, 54, 64: sample liquid storage groove
15, 45, 45': top surface side notch portion
45a, 45a', 56a: low refractive material
46, 56: bottom surface side notch portion
22b, 32b, 46a, 52b: downwardly inclined surface
A: sample liquid
B: light irradiation unit
C: magnetic field application unit
D: light detection unit
W: distance
X: lengthwise direction
Y: thickness direction
$\theta_1, \theta_2, \alpha, \beta$: angle Reference Numerals Used in the Description of the Second Invention 101, 101', 110: target substance detection chip
120, 130, 140, 140', 150: target substance detection chip
102, 102', 112, 122, 132, 142, 142', 152: electric field enhancement layer
103, 103', 113, 123, 133, 143, 143', 153: light transmissive member
103a, 113a, 123a, 133a, 143a, 153a: support surface
103b, 103b', 113b, 143b, 143b': upwardly inclined surface
103c, 113c, 123c, 133c, 143c, 143c', 153c: main body portion
105, 125: sidewall portion
115, 135, 145, 155: sample liquid storage groove
116, 146, 146': top surface side notch portion
146a, 146a', 157a: low refractive material
147, 157: bottom surface side notch portion
123b, 133b, 147a, 153b: downwardly inclined surface
200: optical device
201: optical prism
202: glass substrate
203, 303: metallic film
204, 304: detection chip
206, 306a, 306b: magnet
A: sample liquid
B, 205, 305: light irradiation unit
C: magnetic field application unit
D: light detection unit
W: distance
X: lengthwise direction
Y: thickness direction
$\theta_1, \theta_2, \alpha, \beta$: angle Reference Numerals Used in the Description of the Third Invention 401, 410, 420, 430: target substance detection chip
402, 412, 422, 432: light transmissive substrate
403, 403', 413, 423: uneven structure imparting layer
414, 424, 434: electric field enhancement layer
415, 425, 435: liquid storage portion
450: exemplary uneven structure
451: projection
452: smooth surface
500, 600, 700: target substance detection device
510, 610, 710: light source
520, 620, 720: optical prism
530, 630: first magnetic field application unit
540, 640, 740: light detection unit
730: second magnetic field application unit

The invention claimed is:
1. A target substance detection device comprising:
a detection chip including an entirely approximately plate-shaped light transmissive member, the light transmissive member comprising:
a sensing surface arranged on a surface constituting a top surface relative to a bottom surface,
an inclined surface which is one of
an upwardly inclined surface inclined away from the sensing surface from the top surface toward the bottom surface side with respect to a thickness direction and
a downwardly inclined surface inclined away from the sensing surface from the bottom surface toward the top surface side with respect to the thickness direction, and
a main body portion capable of receiving light and guiding the light through an interior thereof,
the light transmissive member having a light directing structure which is one of
a first light directing structure in which the light applied from the top surface side and passed through the upwardly inclined surface is directed via the main body portion to the sensing surface under a condition of total reflection and
a second light directing structure in which the light applied from the top surface side and reflected at the downwardly inclined surface is directed via the main body portion to the sensing surface under the condition of total reflection;
a light irradiation unit disposed on the side of the top surface of the light transmissive member and operable to irradiate the sensing surface with the light under the condition of total reflection via the light directing structure; and
a magnetic field application unit disposed on the side of the bottom surface of the light transmissive member;
wherein the light transmissive member comprises at least one notch portion out of a top surface side notch portion formed in the top surface and having the upwardly inclined surface and a bottom surface side notch portion formed in the bottom surface and having the downwardly inclined surface.

2. The target substance detection device according to claim 1, wherein the notch portion is filled with a low refractive material that is lower in refractive index than the main body portion.

3. The target substance detection device according to claim 1, wherein the light directing structure is operable to cause at least one of the light passed through the upwardly inclined surface in the first light directing structure and the light reflected at the downwardly inclined surface in the second light directing structure to be reflected at the bottom surface before being directed to the sensing surface under the condition of total reflection.

4. The target substance detection device according to claim 1, wherein a shortest distance between a light incident position on the inclined surface and an irradiated position on the sensing surface is 1.0 mm to 50.0 mm.

5. The target substance detection device according to claim 1, wherein the light transmissive member has a thickness of 0.1 mm to 10.0 mm.

6. The target substance detection device according to claim 1, wherein the light transmissive member comprises a sample liquid storage groove formed in the top surface, the groove having at least a portion constituting the sensing surface.

7. The target substance detection device according to claim 6, wherein the sample liquid storage groove comprises, as the sensing surface, an inclined sensing surface inclined away from the inclined surface from the top surface toward the bottom surface side with respect to the thickness direction of the light transmissive member.

8. The target substance detection device according to claim 1, wherein the light transmissive member comprises a portion of the top surface constituting the sensing surface, and comprises a sidewall portion erected around the sensing surface to form a box-shaped body with the sensing surface as a bottom thereof.

9. A target substance detection method using the target substance detection device according to claim 1, comprising:
- a light irradiation step of irradiating the sensing surface with light under a condition of total reflection from the side of the top surface of the light transmissive member via the light directing structure; and
- a magnetic field application step of applying a magnetic field from the side of the bottom surface of the light transmissive member.

* * * * *